United States Patent [19]
Hansen, Jr. et al.

[11] Patent Number: 6,046,211

[45] Date of Patent: Apr. 4, 2000

[54] AMIDINO DERIVATIVES USEFUL AS NITRIC OXIDE SYNTHASE INHIBITORS

[75] Inventors: Donald W. Hansen, Jr., Skokie, Ill.; Mark G. Currie, St. Charles, Mo.; E. Ann Hallinan, Evanston, Ill.; Kam F. Fok, St. Louis; Timothy J. Hagen, Manchester, both of Mo.; Arija A. Bergmanis; Steven W. Kramer, both of Des Plaines, Ill.; Len F. Lee, St. Charles, Mo.; Suzanne Metz, Chesterfield, Mo.; William M. Moore, St. Charles, Mo.; Karen B. Peterson, Vernon Hills, Ill.; Barnett S. Pitzele, Skokie, Ill.; Dale P. Spangler, Deerfield, Ill.; R. Keith Webber, St. Peters; Mihaly V. Toth, St. Louis, both of Mo.; Mahima Trivedi, Glenview, Ill.; Foe S. Tjoeng, Manchester, Mo.

[73] Assignee: G.D. Searle & Co., Chicago, Ill.

[21] Appl. No.: 09/073,929

[22] Filed: May 6, 1998

Related U.S. Application Data

[60] Division of application No. 08/448,473, filed as application No. PCT/US94/11832, Oct. 20, 1994, which is a continuation-in-part of application No. 08/141,168, Oct. 21, 1993, abandoned.

[51] Int. Cl.$^7$ .................. A61K 31/47; C07D 217/22; C07D 215/38

[52] U.S. Cl. .................. 514/310; 514/224.2; 514/230.5; 514/258; 514/309; 514/312; 514/313; 544/47; 544/48; 544/50; 544/90; 544/91; 544/92; 544/253; 546/113; 546/141; 546/143; 546/153; 546/159

[58] Field of Search .................. 514/224.2, 230.5, 514/258, 309, 310, 312, 313; 544/47, 48, 50, 90, 91, 92, 253; 546/113, 141, 143, 153, 159

[56] References Cited

U.S. PATENT DOCUMENTS

| | | | |
|---|---|---|---|
| 2,049,582 | 8/1936 | Ziegler | 260/127 |
| 3,109,848 | 11/1963 | Bortnick et al. | 260/313 |
| 3,121,093 | 2/1964 | Bortnick et al. | 260/313 |
| 3,132,151 | 5/1964 | Bortnick et al. | 260/313 |
| 3,501,487 | 3/1970 | Poos | 260/296 |
| 3,563,994 | 2/1971 | Wollweber et al. | 260/293 |
| 3,694,432 | 9/1972 | Hershenson | 260/239 |
| 3,725,435 | 4/1973 | Poos | 260/326.5 |
| 3,816,457 | 6/1974 | Grisar et al. | 260/329 |
| 4,046,909 | 9/1977 | Rasmussen et al. | 424/274 |
| 4,061,746 | 12/1977 | Blohm et al. | 424/244 |
| 4,126,613 | 11/1978 | Grisar et al. | 260/239 |
| 4,126,621 | 11/1978 | Grisar et al. | 260/329 |
| 4,153,235 | 5/1979 | Grisar et al. | 260/239 |
| 4,443,468 | 4/1984 | Maillard et al. | 424/274 |
| 4,523,020 | 6/1985 | Moormann et al. | 548/353 |
| 4,525,476 | 6/1985 | Butler et al. | 514/326 |
| 4,533,739 | 8/1985 | Pitzele et al. | 548/559 |
| 4,556,674 | 12/1985 | Maillard et al. | 514/426 |
| 4,579,951 | 4/1986 | Pitzele et al. | 546/223 |
| 4,699,918 | 10/1987 | Maillard et al. | 514/426 |
| 4,855,444 | 8/1989 | Wambach | 548/408 |
| 4,962,204 | 10/1990 | Wambach | 548/408 |
| 5,028,627 | 7/1991 | Kilbourn et al. | 514/565 |
| 5,051,444 | 9/1991 | Tamoto et al. | 514/397 |
| 5,059,712 | 10/1991 | Griffith | 562/560 |
| 5,081,148 | 1/1992 | Braquet et al. | 514/162 |
| 5,132,453 | 7/1992 | Griffith | 562/560 |
| 5,196,439 | 3/1993 | Sugimoto et al. | 514/318 |
| 5,216,025 | 6/1993 | Gross et al. | 514/565 |
| 5,246,971 | 9/1993 | Williamson et al. | 514/634 |
| 5,266,594 | 11/1993 | Dawson et al. | 514/560 |
| 5,273,875 | 12/1993 | Griffith | 435/1 |
| 5,621,004 | 4/1997 | Dunn et al. | 514/551 |
| 5,629,322 | 5/1997 | Guthikonda et al. | 514/313 |

FOREIGN PATENT DOCUMENTS

| | | |
|---|---|---|
| 191584 | 12/1981 | Czech Rep. . |
| 0370320 | 5/1990 | European Pat. Off. . |
| 0446699 | 9/1991 | European Pat. Off. . |
| 0462948 | 12/1991 | European Pat. Off. . |
| 0676196 | 10/1995 | European Pat. Off. . |
| 0713704 | 5/1996 | European Pat. Off. . |
| 0713876 | 5/1996 | European Pat. Off. . |
| 0717040 | 6/1996 | European Pat. Off. . |
| 1367598 | 9/1974 | United Kingdom . |
| 2240041 | 7/1991 | United Kingdom . |
| 91/04023 | 4/1991 | WIPO . |
| 91/04024 | 4/1991 | WIPO . |
| 93/13055 | 7/1993 | WIPO . |
| 93/16721 | 9/1993 | WIPO . |
| 93/24126 | 12/1993 | WIPO . |
| 94/12163 | 6/1994 | WIPO . |
| 94/12165 | 6/1994 | WIPO . |
| 94/14780 | 7/1994 | WIPO . |
| 94/16729 | 8/1994 | WIPO . |
| 95/05363 | 2/1995 | WIPO . |

(List continued on next page.)

OTHER PUBLICATIONS

Armarego et al., Purine Studies. Part XX. Methylation and Reduction of 2,8–Dioxo–, 2,8–Diamino–, and 2–Amino–8–oxo–purines, and the Sterochemistry of their 1,4,5,6–Tetrahydro–derivatives, Journal of the Chemical Society, Perkin Transactions I, vol. 13, 1976.

Armarego et al., Quinazolines. Part XXI. Synthesis of cis–2–Amino–8a–carboxymethyl–3,4,4a,5,6,7,8,8a–octahydroquinazoline and Related Compounds. Conversion of Perhydroaquinazolin–2–ones into 2–Amino–3,4,4a,5,6,7,8,8a–octahydroquinazolines, Journal of th, 1975.

Armarego et al., Quinazolines. Part XV. Hexahydro– and Octahydro–quinazolines, Journal of the Chemical Society (C), vol. 2, pp. 238–245, 1971.

(List continued on next page.)

Primary Examiner—Mukund J. Shah
Assistant Examiner—Brenda Coleman
Attorney, Agent, or Firm—Alan L. Scrivner; Dennis A. Bennett

[57] ABSTRACT

The current invention discloses useful pharmaceutical compositions containing amidino derivative useful as nitric oxide synthase inhibitors.

9 Claims, 1 Drawing Sheet

FOREIGN PATENT DOCUMENTS

| | | |
|---|---|---|
| 95/11231 | 4/1995 | WIPO . |
| 95/31987 | 11/1995 | WIPO . |
| 95/32203 | 11/1995 | WIPO . |
| 96/14842 | 5/1996 | WIPO . |
| 96/14844 | 5/1996 | WIPO . |
| 96/18616 | 6/1996 | WIPO . |
| 97/16430 | 5/1997 | WIPO . |

OTHER PUBLICATIONS

Armarego et al., Quinazolines. Part XIV. The Absolute Configurations of cis– and trans–(+)– and (–)–Decahydroquinazolines and 2–Amino–octahydroquinazolines, Journal of the Chemical Society (C), vol. 11, pp. 1597–1600, 1970.

Culvenor, C.C.J. et al, *Aust. J. Chem.*, 24 (1971) 371–375 (Beilstein Registry ID Only).

Caujolle, R. et al, *Eur. J. Med. Chem. Chim. Ther.*, 28(1) (1993) 29–35 (Beilstein Registry ID Only).

Kato et al, *Chem. Pharm. Bull.*, 20 (1972) 901 (Beilstein Registry ID Only).

Anderson, Wayne K. et al, *Synth. Commun.*, 19(13–14) (1989) 2237–2242 (Beilstein Registry ID Only).

Olomucki et al, *Biochim. Biophys. Acta*, 263 (1972) 213, 215, 216 (Beilstein Registry ID Only).

Otake, N. et al, *Tetrahedron Lett.*, 19 (1965) 1411–1419 (Beilstein Registry ID Only).

Patent: Kerin Seiyaku Kabushiki Kaisya, JP, A, 17189, 1968; *Referati vnyi Zhurnal. Kimiya.*, 1 (1970) N469P (Beilstein Registry ID Only).

Umezawa et al, *J. Antibiot.*, 26 (1973) 625, 637 (Beilstein Registry ID Only).

Marconi et al, *J. Antibiot.*, 23 (1970) 120, 121, 122, 123 (Beilstein Registry ID Only).

Kretow et al, *J. Gen. Chem. USSR*, 32 (1962) 464 (Beilstein Registry ID Only).

Dorn et al, *Chem. Ber.*, 103 (1970) 2505, 2506, 2508, 2511 (Beilstein Registry ID Only).

Andrewes et al, *Proc. R. Soc. London B*, 133 (1946) 20, 53 (Beilstein Registry ID Only).

Schubert, H. W. et al, *Arch. Pharm. Ber. Dtsch. Pharm. Ges.*, 301(10) (1968) 750–762 (Beilstein Registry ID Only).

Stefanye et al, *J. Amer. Chem. Soc.*, 77 (1955) 761 (Beilstein Registry ID Only).

Goodman et al, *J. Org. Chem.*, 23 (1958) 1954, 1956, (Beilstein Registry ID Only).

Goodman et al, *J. Org. Chem.*, 23 (1958) 1251, 1252, 1255, 1954, 1956 (Beilstein Registry ID Only).

Bertolini et al., "Nitric Oxide Synthase Inhibitors: Recent Advances", *Cardiovascular & Renal Patent Update*, Ashley Publications Ltd., pp. 1339–1345, 1994.

Perrin et al., "Absence of Stereoelectronic Control in Hydrolysis of Cyclic Amidines", *J. Am. Chem. Soc.*, vol. 108, No. 19, pp. 5997–6003, 1986.

Huber et al., "Saturated Heterocycles, Part 88. Synthesis of a New Ring System: Dipyrido–[1.2–a:4,3–d] pyrimidin–11–one Derivatives", *J. Chem. Soc. Perkin Trans. 1*, pp. 909–912, 1987.

Kökösi et al., "Nitrogen Bridgehead Compounds. Part 19(1). Synthesis of Polymethylenepyrimidin–4–ones", *J. Heterocyclic Chem.*, vol. 19, pp. 909–912, 1982.

Brown et al., Hydropyrimidines, Part II, pp. 4041–4045, 1962.

Adcock et al., 2–Amino–2–imidazolines 2–Amino–2–oxazolines, Part II, pp. 474–479, 1965.

Stefanye et al., "Cyclic Guanidines from Nitrimino Compounds", *J. Am. Chem. Soc.*, vol. 77, No. 3, pp. 761–762, 1955.

Klayman et al., "2–Amino–2–thiazoline. VII. Unequivocal Structure Assignment of the Products of the Reaction of 2–Amino–2–thiazoline and Its Analogs with Carbethoxy Isothiocyanate", *J. Org. Chem.*, vol. 39, No. 13, pp. 1819–1823, 1974.

Moriconi et al., "Synthesis and Reactions of Cyclic Amidines", *J. Org. Chem.*, vol. 33, No. 5, pp. 2109–2111, 1968.

Wagenaar et al., "Methodology for the Preparation of N–Guanidino–Modified Arginines and Related Derivatives", *J. Org. Chem.*, vol. 58, No. 1, pp. 4331–4338, 1993.

Gutteridge, "Acylation of 2–Amino–5, 5–dimethyl–Δ–pyrroline 1–Oxide", *J. Chem. Soc.*, (C), pp. 3121–3125, 1971.

Langlois et al., "Derivatives of Imidazole, 1,3,4–triazole and tetrazole", *J. Heterocycl. Chem.*, vol. 19, No. 1, pp. 193–200, 1982 (English Summary, p. 200).

Langlois et al., "Synthesis and Antidepressant Properties of 2–Amino–phenyl–1–pyrroline Derivatives", *Eur. J. Med. Chem.*, vol. 13, No. 2, pp. 161–169, 1978 (English Summary, p. 169).

Klötzer et al. "Acylderivatives of 2–Amino–1–pyrrolines", *Monatshefte für Chemie*, vol. 102, No. 2, pp. 627–634, 1971 (English Summary, p. 627).

Klötzer et al. "Synthesis of Substituted 2–Amino–1–pyrrolines, I." *Monatshefte für Chemie*, vol. 101, No. 5, pp. 1263–1270, 1979 (English Summary, p. 1263).

Nakane et al., "Novel Potent and Selective Inhibitors of Inducible Nitric Oxide Synthase", *Molecular Pharmacology*, vol. 47, pp. 831–834, 1995.

Dunbar et al., "Design, Synthesis, and Neurochemical Evaluation of 2–Amino–5–(alkoxycarbonyl)–3,4,5,6–tetrahydopyridines and 2–Amino–5–(alkoxycarbonyl)–1,4,5,6–tetrahydropyrimidines as $M_1$ Muscarinic Receptor Agonists", *J. Med. Chem.*, vol. 37, No. 17, pp. 2774–2782, 1994.

Klötzer et al. "Synthesis of Substituted 2–Aminopyrrolines, II." *Monatshefte für Chemie*, vol. 101, No. 6, pp. 1841–1850, 1970 (English Summary, p. 1841).

Berge et al., "Pharmaceutical Salts", *J. Pharm. Sci.*, vol. 66, No. 1, pp. 1–19, 1977.

Moncada et al., "Nitric Oxide: Physiology, Pathophysiology, and Pharmacology", *Pharmacological Reviews*, Vo. 43, No. 2, pp. 109–142, 1991.

Moncada et al, "Biosynthesis of Nitric Oxide from L–Arginine", *Biochemical Pharm.*, Vol 38, No. 11, pp. 1709–1715, 1989.

Mazurek et al., "Theoretical Studies of Tautomerism of Clonidine Vacuum and in Water Medium", *Theochem*, 82(1–2), 23–8, 1991.

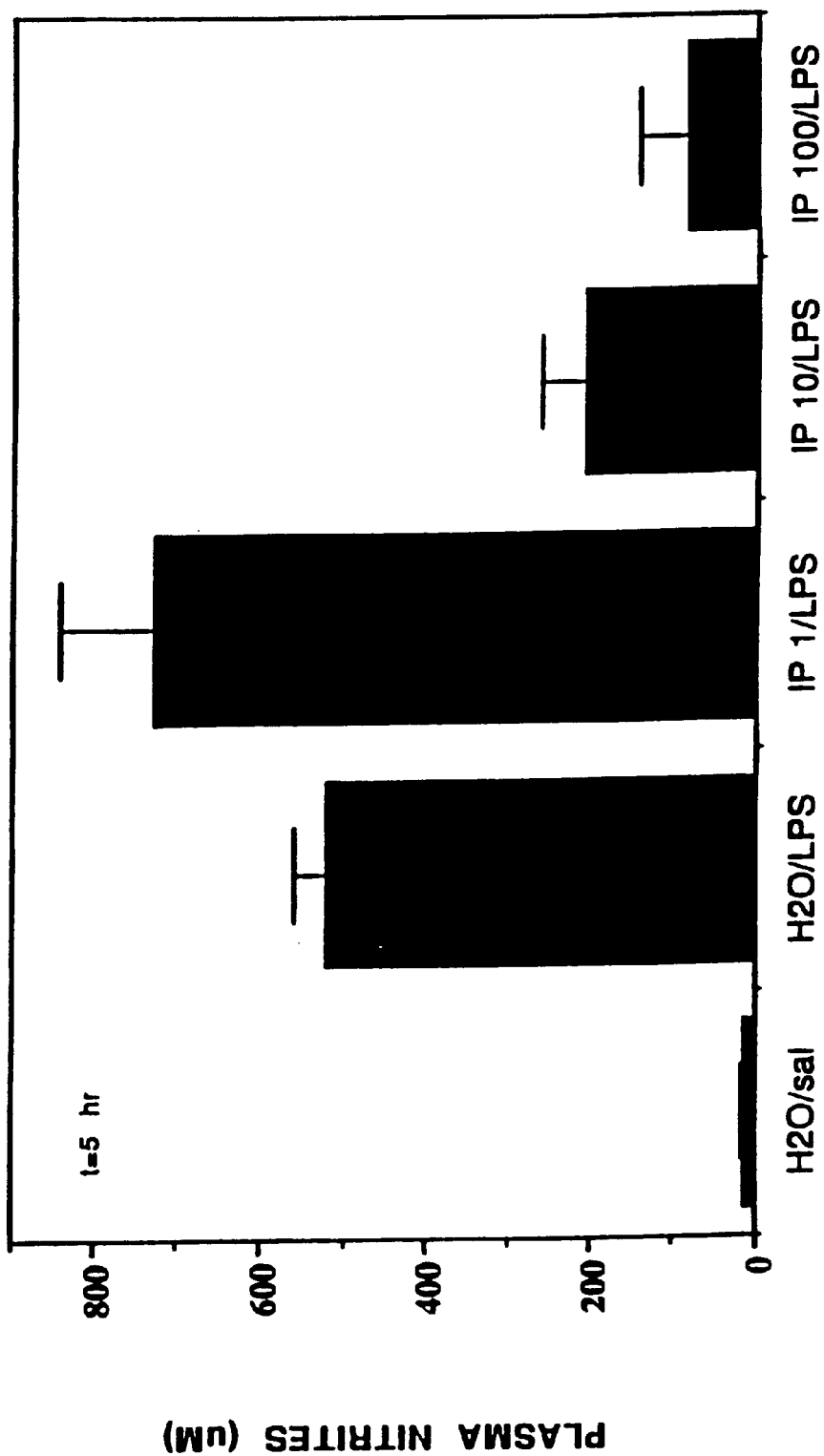
FIG. 1/1

AMIDINO DERIVATIVES USEFUL AS NITRIC OXIDE SYNTHASE INHIBITORS

This application is a divisional of U.S. patent application Ser. No. 08/448,473 filed Jun. 6, 1995, incorporated by reference, which is a 371 of PCT/US94/11832 filed Oct. 20, 1994 which is a continuation-in-part of U.S. patent application Ser. No. 08/141,168 filed Oct. 21, 1993, now abandoned.

BACKGROUND OF THE INVENTION

1. Field of the Invention

The present invention relates to amidino derivatives, pharmaceutical compositions containing amidino derivatives, and to their use in therapy, in particular their use as nitric oxide synthase inhibitors.

2. Related Art

It has been known since the early 1980's that the vascular relaxation brought about by acetycholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amylnitrite, glyceryltrinitrite and other nitrovasodilators. The recent identification of EDRF as NO has coincided with the discovery of a biochemical pathway by which NO is synthesized from the amino acid L-arginine by the enzyme NO synthase.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al, *Biochemical Pharmacology*, 38, 1709–1715 (1989) and Moncada et al, *Pharmacological Reviews*, 43, 109–142 (1991). It is now thought that excess NO production may be involved in a number of conditions, particularly conditions which involve systemic hypotension such as toxic shock and therapy with certain cytokines.

The synthesis of NO from L-arginine can be inhibited by the L-arginine analogue, L-N-monomethyl-arginine (L-NMMA) and the therapeutic use of L-NMMA for the treatment of toxic shock and other types of systemic hypertension has been proposed (WO 91/04024 and GB-A-2240041). The therapeutic use of certain other NO synthase inhibitors apart from L-NMMA for the same purpose has also been proposed in WO 91/04024 and in EP-A-0446699.

It has recently become apparent that there are at least three types of NO synthase as follows:

(i) a constitutive, $Ca^{++}$/calmodulin dependent enzyme, located in the endothelium, that releases NO in response to receptor or physical stimulation.

(ii) a constitutive, $Ca^{++}$/calmodulin dependent enzyme, located in the brain, that releases No in response to receptor or physical stimulation.

(iii) a $Ca^{++}$ independent enzyme which is induced after activation of vascular smooth muscle, macrophages, endothelial cells, and a number of other cells by endotoxin and cytokines. Once expressed this inducible No synthase synthesizes NO for long periods.

The NO released by the constitutive enzymes acts as a transduction mechanism underlying several physiological responses. The NO produced by the inducible enzyme is a cytotoxic molecule for tumor cells and invading microorganisms. It also appears that the adverse effects of excess NO production, in particular pathological vasodilation and tissue damage, may result largely from the effects of NO synthesized by the inducible NO synthase.

There is also a growing body of evidence that NO may be involved in the degeneration of cartilage which takes place in certain conditions such as arthritis and it is also known that NO synthesis is increased in rheumatoid arthritis. Accordingly, further conditions in which there is an advantage in inhibiting NO production from L-arginine include autoimmune and/or inflammatory conditions affecting the joints, for example arthritis.

Conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy. Further conditions in which there is an advantage in inhibiting NO production from L-arginine include autoimmune diseases and/or inflammatory conditions such as those affecting the joints, for example arthritis or inflammatory bowel disease, cardiovascular ischemia, diabetes, hyperalgesia (allodynia) cerebral ischemia (Both focal ischemia, thrombotic stroke and global ischemia, secondary to cardiac arrest) and other CNS disorders mediated by NO.

Some of the NO synthase inhibitors proposed for therapeutic use so far, and in particular L-NMMA, are non-selective in that they inhibit both the constitutive and the inducible NO synthase. Use of such a non-selective NO synthase inhibitor requires that great care be taken in order to avoid the potentially serious consequences of over-inhibition of the constitutive NO-synthase including hypertension and possible thrombosis and tissue damage. In particular, in the case of the therapeutic use of L-NMMA for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive NO synthase would be of even greater therapeutic benefit and easier to use.

WO 94/12165, WO 94/14780, Wo93/13055, EP 0446699A1 and U.S. Pat. No. 5,132,453 disclose compounds that inhibit nitric oxide synthesis and preferentially inhibit the inducible isoform of nitric oxide synthase. The disclosures of which are hereby incorporated by reference in their entirety as if written herein.

BRIEF DESCRIPTION OF THE DRAWINGS

FIG. 1 shows the effect of orally administered 2-iminopiperidine (mg/kg) on LPS-induced increase in plasma nitrites in rat.

SUMMARY OF THE INVENTION

In a broad aspect, the present invention is directed to inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase.

The invention further relates to a pharmaceutical composition comprising a compound having the formula (I):

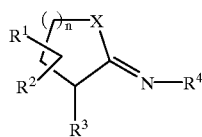

(I)

and salts, pharmaceutically acceptable esters and prodrugs thereof, wherein:

X is selected from the group consisting of methylene, nitrogen, oxygen, S, SO, and $SO_2$ wherein nitrogen and lower alkyl radicals may optionally be substituted with hydroxy, lower alkyl, lower alkoxy, amino, and haloalkyl groups;

n=0 to about 7;

$R^1$ and $R^2$, are independently selected from the group consisting of hydrogen, hydroxy, lower alkyl, lower alkenyl, lower alkynyl, lower alkoxy, lower thioalkoxy, halogen, nitro, amino, carboxyl, cyano, sulfonyl, haloalkyl, carboalkoxy, carboaryloxy, carboalkylaryloxy, alicyclic hydrocarbon, heterocycly, aromatic hydrocarbon, —$CONR^5R^6$, —$SO_2NR^5R^6$, —$COR^5$, —$SO_2R^5$, alkyl sulfoxide, aryl sulfoxide, alkyl sulfone, aryl sulfone, alkyl sulfate, aryl sulfate, and sulfonamide, wherein all said radicals can be optionally substituted with one or more of the following:

hydroxy, lower alkyl, lower alkenyl, lower alkynyl, lower alkoxy, lower thioalkoxy, halogen, nitro, amino, carboxyl, cyano, sulfonyl, carboalkoxy, carboaryloxy, carboxyalkylaryloxy, haloalkyl, —$SO_2NR^5R^6$ and —$SO_2R^5$ wherein all said substitutions may be optionally substituted with one or more of the following: amino, carboxyl, carboalkoxy, carboaryloxy, carboxyalkylaryloxy and lower alkoxy;

and $R^1$, $R^2$, may optionally together form an alicyclic hydrocarbon, heterocycly or aromatic hydrocarbon and said optionally formed ring may be optionally substituted with one or more of the following:

lower alkyl, lower alkenyl, lower alkynyl which may be optionally substituted with carboxyl, carboalkoxy, carboaryloxy, carboxyalkylaryloxy and lower alkoxy;

$R^3$, $R^4$ are independently selected from the group consisting of hydrogen, hydroxy, and alkyloxy;

$R^5$ and $R^6$ are independently selected from the group consisting of hydrogen, lower alkyl, and aryl;

with the proviso that when n=1

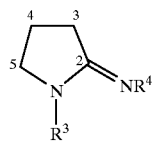

and $R^1$ and/or $R^2$ are at position 3 or 4, neither $R^1$ or $R^2$ is aryl; and together with at least one non-toxic pharmaceutical acceptable carrier.

n is preferably 1,2,3,4,5,6, or 7, more preferably n is 1–5, still more preferred n is 1–4, most preferred n is 1–3.

Compounds and compositions defined above have usefulness as inhibitors of nitric oxide synthase. These compounds also preferentially inhibit the inducible form over the constitutive form.

DETAILED DESCRIPTION OF THE INVENTION

A preferred embodiment of the present invention is a pharmaceutical composition of the formula;

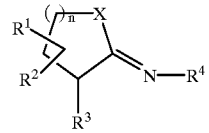

X is selected from the group consisting of methylene, nitrogen, oxygen and sulfur;

n is an integer 0 to 5;

$R^1$ and $R^2$, are independently selected from the group consisting of hydrogen, hydroxy, lower alkyl, lower alkenyl, lower alkynyl, haloalkyl, aromatic hydrocarbon and alicyclic hydrocarbon wherein all said radicals are optionally substituted with one or more of the following: carboxyl, carboalkoxy, amino, lower alkoxy, lower thioalkoxy and lower alkyl wherein all said substitutions may be optionally substituted with one or more of the following:amino, carboxyl, and carboalkoxy;

and $R^1$, $R^2$, may optionally together form an alicyclic hydrocarbon or aromatic hydrocarbon; and $R^3$, $R^4$ are independently selected from the group consisting of hydrogen and hydroxy.

Another preferred embodiment of the present invention is a compound of the formula:

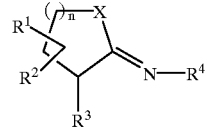

and salts, pharmaceutically acceptable ester and prodrugs thereof, wherein:

X is selected from the group consisting of methylene, nitrogen, oxygen, sulfur, SO, or $SO_2$;

n=o to about 7;

$R^1$ and $R^2$, are independently selected from the group consisting of hydrogen, hydroxy, lower alkyl, lower alkenyl, lower alkynyl, lower alkoxy, lower thioalkoxy, halogen, nitro, amino, carboxyl, cyano, sulfonyl, haloalkyl, carboalkoxy, carboaryloxy, carboalkylargyloxy, alicyclic hydrocarbon, heterocycly, aromatic hydrocarbon, —$CONR^5R^6$, —$SO_2nR^5R^6$, —$COR^5$, —$SO_2R^5$, alkyl sulfoxide, aryl sulfoxide, alkyl sulfone, aryl sulfone, alkyl sulfate, aryl sulfate, and sulfonamide, wherein all said radicals are optionally substituted with one or more of the following: hydroxy, alkyl, lower alkenyl, lower alkynyl, lower alkoxy, halogen, nitro, amino, carboxyl, cyano, sulfonyl, carboalkoxy, carboaryloxy, carboxyalkylaryloxy, haloalkyl, —$SO_2NR^5R^6$ and —$SO_2R^5$ wherein all said substitutions may be optionally substituted with one or more of the following: amino, carboxyl,carboalkoxy, carboaryloxy, carboxyalkylaryloxy and lower alkoxy;

and $R^1$, $R^2$, may optionally together form an alicyclic hydrocarbon, heterocycly or aromatic hydrocarbon and said optionally formed ring may be optionally substituted with one or more of the following lower alkyl, lower alkenyl, lower alkynyl which may be optionally substituted with carboxyl,carboalkoxy, carboaryloxy, carboxyalkylaryloxy and lower alkoxy;

R³, R⁴ are hydrogen,hydroxy, and alkyloxy;

R⁵ and R⁶ are independently selected from the group consisting of hydrogen, lower alkyl, and aryl;

with the proviso that when n=1

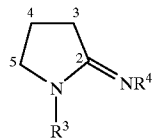

and R¹ and/or R² are at position 3 or 4, neither R¹ or R² is aryl and with the further proviso that when X is methylene, nitrogen, oxygen, or sulfur then R¹ and R² cannot be both H, or be a haloalkyl and where N=3 R¹ cannot be Methyl at position 7.

The present invention includes compounds listed above in the form of salts, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, p-toluenesulphonic, benzenesulphonic and isethionic acids. Salts of the compounds of formula (I) can be made by reacting the appropriate compound in the form of the free base with the appropriate acid.

While it may be possible for the compounds of formula (I) to be administered as the raw chemical, it is preferable to present them as a pharmaceutical formulation. According to a further aspect, the present invention provides a pharmaceutical formulation comprising a compound of formula (I) or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.1 to 500 mg/kg per day. The dose range for adult humans is generally from 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

It will be understood that the specific dose level for any particular patient will depend upon a variety of factors including the activity of the specific compound employed, the age, body weight, general health, sex, diets, time of administration, route of administration, rate of excretion, drug combination, and the severity of the particular disease undergoing therapy.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, penten-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radicals in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "alicyclic hydrocarbon" means a aliphatic radical in a ring with 3 to about 10 carbon atoms, and preferably from 3 to about 6 carbon atoms. Examples of suitable alicyclic radicals include cyclopropyl, cyclopropylenyl, cyclobutyl, cyclopentyl, cyclohexyl, 2-cyclohexen-1-ylenyl, cyclohexenyl and the like.

The term "aromatic hydrocarbon radical" means 4 to about 16 carbon atoms, preferably 6 to about 12 carbon atoms, more preferably 6 to about 10 carbon atoms. Examples of suitable aromatic hydrocarbon radicals include phenyl, naphthyl, and the like.

The term "acyloxy" means 1 to about 4 carbon atoms. Suitable examples include alkanoyloxy, benzoyloxy and the like.

The term "heterocyclic radical" means a saturated or unsaturated cyclic hydrocarbon radical with 4 to about 10 carbon atoms, preferably about 5 to about 6; wherein 1 to about 3 carbon atoms are replaced by nitrogen, oxygen or sulfur. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazonlinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, and the like.

The term "lower alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, isobutoxy, sec-butoxy, tert-butoxy and the like.

The term "lower thioalkoxy" means the same as "alkoxy" except sulfur replaces oxygen.

The term "halogen" means fluorine, chlorine, bromine or iodine.

The term "haloalkyl" means a lower alkyl as defined above having 1–5 preferably 1–3 halogens attached to said lower alkyl chain.

The term "prodrug" refers to a compound that is made more active in vivo.

As used herein, reference to "treatment" of a patient is intended to include prophylaxis.

All references, patents or applications, U.S. or foreign, cited in the application are hereby incorporated by reference as if written herein.

The following schemes can be used to practice the present invention.

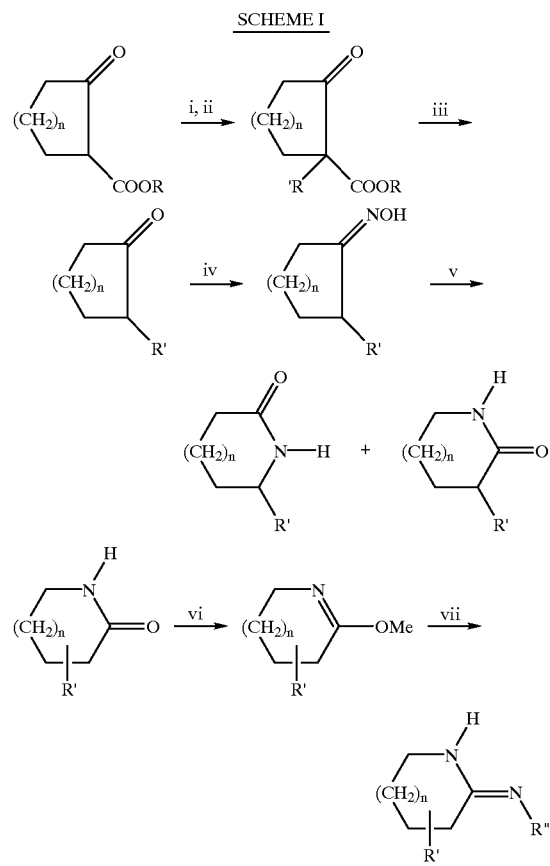

Legend:
i. NaH/DMF;
ii. R'Br;
iii. LiCl/DMSO/H$_2$O/heat;
iv. NH$_2$OH•HCl/NaOAc/EtOH/H$_2$O/Acetone;
vi. Me$_3$O$^+$BF$_4^-$/CH$_2$Cl$_2$;
vii. R"NH$_2$/MeOH/Heat

SCHEME II

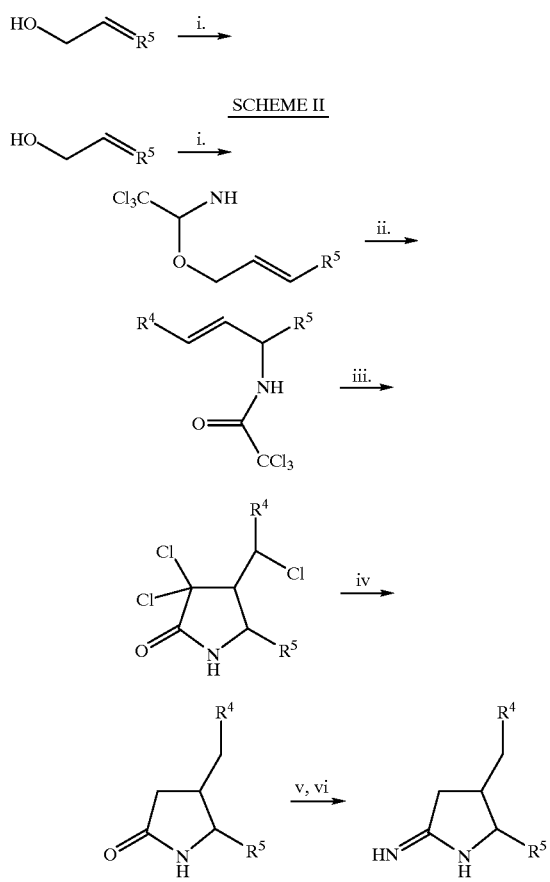

Legend:
i. Base,
CCl₃CN
ii. 140° C.
iii. (Ph₃P)₂RuCl₂
iv. Bu₃SnH
v. (CH₃)₃OBF₄
vi. NH₄Cl

SCHEME III

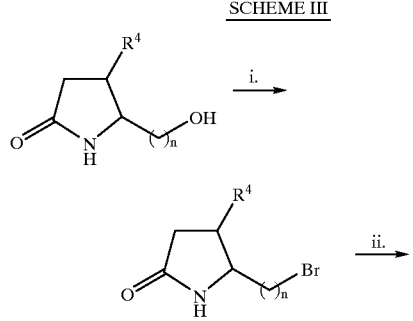

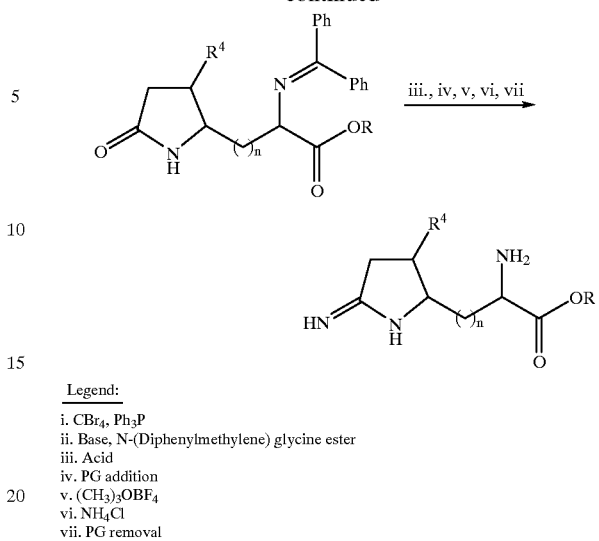

Legend:
i. CBr₄, Ph₃P
ii. Base, N-(Diphenylmethylene) glycine ester
iii. Acid
iv. PG addition
v. (CH₃)₃OBF₄
vi. NH₄Cl
vii. PG removal

SCHEME IV

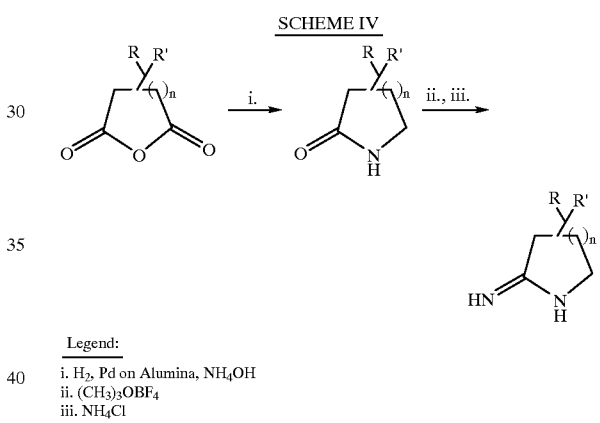

Legend:
i. H₂, Pd on Alumina, NH₄OH
ii. (CH₃)₃OBF₄
iii. NH₄Cl

The invention is illustrated by the following examples. Some of the compounds disclosed are publicly available from the source cited.

EXAMPLE 1

2-Imino-heptamethyleneimine hydrochloride

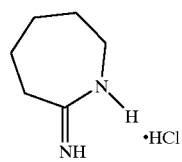

To a 50 mL flask was added 5 g (0.04 mol) of 2-oxo-heptamethyleneimine and 15 mL of benzene. This was stirred at reflux while 4.8 g (0.038 mol) of dimethylsulfate were added dropwise. After the addition was complete, stirring was continued at reflux for 18 hours. The heat was then removed, the reaction mixture was diluted with ethyl acetate (EtOAc) and washed with two 100 mL portions of aqueous potassium carbonate ($K_2CO_3$). The organic layer was dried ($MgSO_4$), filtered and concentrated to afford 4.2 g of the iminoether as a yellow oil. 2.2 g (0.016 mol) of the iminoether were dissolved in 50 mL of anhydrous ethanol (EtOH) and 0.85 g (0.016 mol) of ammonium chloride was added. This mixture was stirred at 25° C. for three days. Removal of the solvent in vacuo afforded 1.7 g (48%) of the 2-imino-heptamethyleneimine hydrochloride as a white solid, mp 166–175° C. MH$^+$=127.

Elemental analysis: $C_7H_{14}N_2 \cdot HCl \cdot 1/4 \, H_2O$

|  | C | H | N |
|---|---|---|---|
| Calculated: | 50.30 | 9.35 | 16.76 |
| Found: | 49.95 | 9.22 | 17.12 |

EXAMPLE 2

2-Imino-octamethyleneimine hydrochloride

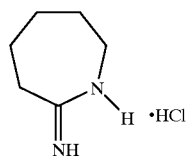

To a 100 mL flask was added 5 g (0.035 mol) of 2-oxo-octamethyleneimine and 15 mL of benzene. This was stirred at reflux while 4.4 g (0.035 mol) of dimethylsulfate was added dropwise. After the addition were complete, stirring was continued at reflux for 18 hours. The heat was then removed, the reaction mixture was diluted with EtOAc and washed with two 100 mL portions of aqueous potassium carbonate. The organic layer was dried (MgSO$_4$), filtered and concentrated to afford 4.4 g of the iminoether as a yellow oil. The iminoether was dissolved in 50 mL of anhydrous EtOH and 1.5 g (0.028 mol) of ammonium chloride was added. This mixture was stirred at 25° C. for six days. Removal of the solvent in vacuo afforded 2.75 g (45%) of the 2-imino-octamethyleneimine hydrochloride as a white solid, mp 108–128° C. MH$^+$=141.

Elemental analysis: $C_8H_{16}N_2 \cdot HCl \cdot 1/3 H_2O$

|  | C | H | N |
|---|---|---|---|
| Calculated: | 52.77 | 9.74 | 15.35 |
| Found: | 53.05 | 9.41 | 14.98 |

EXAMPLE 3

3,4,5,6,7,8-hexahydro-2[1H]-quinolineimine hydroiodide

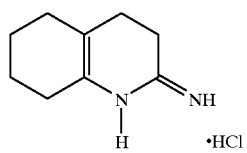

3,4,5,6,7,8-Hexahydro-2[1H]-quinolinone (3.0 g, 20 mmol), 2,4-bis(4-methoxy-phenyl)1,3-dithia-2,4-diphosphetane 2,4-disulfide (4.0 g, 10 mmol), and 100 ml of toluene were mixed and refluxed for three hours. The dark brown solution was cooled to room temperature, and filtered. The filtrate was rotary evaporated. The residue was dissolved in methylene chloride (CH$_2$Cl$_2$) and applied to a column of silica gel equilibrated with Ch$_2$Cl$_2$. The thioamide rich fractions, identified by mass spectroscopic analyses, were combined and evaporated. The residue (0.38 g, 2.3 mmol) was treated with methyl iodide (0.36 g, 2.6 mmol) in acetone at 20° C. for four hours. After rotary evaporation, the residue was washed with (Et$_2$O), several times. The residue was treated with ammonia-saturated EtOH at 20° C. for 12 hours. After evaporation, the residue was washed with Et$_2$O, and recrystallized from a mixture of EtOH and Et$_2$O. The product was isolated as pale yellow solid and the mass spectrum was consistent with the proposed structure. (MH$^+$=150.1); m.p. 150–155° C.

EXAMPLE 4

2-Imino-3-methyltetramethyleneimine hydriodide

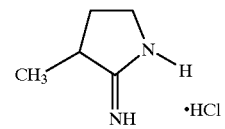

The title compound was prepared by the method of EXAMPLE 3. 3-Methyl-2-pyrrolidinone (5.0 g, 50 mmol) was converted to the thioamide which was reacted with methyl iodide, and treated subsequently with ammonia-saturated ethyl alcohol. The product was isolated as a white amorphous solid with mass spectrum consistent with the proposed structure. (MH+=98.4); m.p. 73–75° C.

EXAMPLE 5

2-Imino-5-methyltetramethyleneimine hydriodide

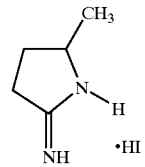

The method of preparation of 3,4,5,6,7,8-nexahydro-2[1H]quinolineimine hydriodide, EXAMPLE 3, was used to convert 5-methyl-2-pyrrolidone to the title compound which was obtained as white solid. The mass spectrum of the product was found to be consistent with the proposed structure. (MH+=98.4); m.p. 83–85° C.

EXAMPLE 6

2-Imino-4-methylpiperidine acetate

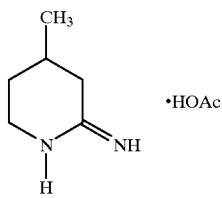

2-Amino-4-methylpyridine (1.56 g; 15 mmoles) and 5% rhodium on carbon (0.51 g, wet, Degussa type G10) in glacial acetic acid (30 mL) were shaken on a Parr hydrogenation apparatus at 55 psi of hydrogen overnight. The catalyst was removed by filtration and the filtrate was diluted with water to 250 mL, and lyophilized to yield a light tan powder. The powder was recrystallized from warm ethanol/ether to give 0.3 g of white solid. mp 181–182° C. A second crop of white solid was obtained (0.85 g; mp 180–182° C.). MH+=113; $^1$H NMR (D$_2$O): δ3.32–3.16 (m, 2H); 2.54–2.46 (m, 1H); 2.10–2.00 (m, 1H); 1.80–1.70 (m, 2H); 1.74 (s, 3H); 1.32–1.25 (m, 1H); 0.87 (d, J=6.6 Hz, 3H).

Elemental analysis: $C_6H_{12}N_2 \cdot CH_3COOH$

|  | C | H |
|---|---|---|
| Calculated: | 55.79 | 9.36 |
| Found: | 55.85 | 9.22 |

EXAMPLE 7

2-Imino-5-methylpiperidine acetate

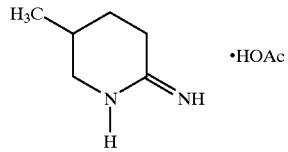

The method of preparation of 2-imino-4-methylpiperidine acetate, EXAMPLE 6, was used to convert 2-amino-5-methylpyridine to the title compound which was obtained as a white solid. The analysis of the product was found to be consistent with the proposed structure. m.p. 175–178° C. MH+=113; d$^1$H NMR (D$_2$O): δ3.28–3.21 (m, 1H); 2.79–2.70 (m, 1H); 2.49–2.43 (m, 2H); 1.79–1.67 (m, 2H); 1.73 (s, 3H); 1.30–1.23 (m, 1H); 0.82 (d, J=6.6 Hz, 3H).

Elemental analysis: $C_6H_{12}N_2 \cdot CH_3COOH$

|  | C | H |
|---|---|---|
| Calculated: | 55.79 | 9.36 |
| Found: | 55.81 | 9.39 |

EXAMPLE 8

2-Imino-6-methylpiperidine hydrochloride

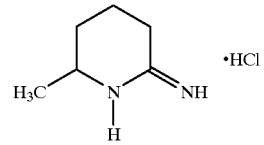

The method of preparation of 2-imino-4-methylpiperidine acetate, EXAMPLE 6, was used to convert 2-amino-6-methylpyridine to the title compound which was obtained as a white solid. The analysis of the product was found to be consistent with the proposed structure. m.p. 160–162° C. MH+=113; $^1$H NMR (D$_2$O): δ3.58–3.40 (m, 1H); 2.60–2.35 (m, 2H); 1.95–1.70 (m, 2H); 1.68–1.50 (m, $^1$H); 1.40–1.35 (m, 1H); 1.05 (d, J=6.6 Hz, 3H).

Elemental analysis: $C_6H_{12}N_2 \cdot HCl$

|  | C | H | N |
|---|---|---|---|
| Calculated: | 48.49 | 8.82 | 18.85 |
| Found: | 48.32 | 9.01 | 18.70 |

EXAMPLE 9

2-imino-3-methylpiperidine acetate

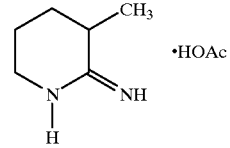

The method of preparation of 2-imino-3-methylpiperidine acetate, EXAMPLE 6, was used to convert 2-amino-6-methylpyridine to the title compound which was obtained as a white solid. The analysis of the product was found to be consistent with the proposed structure. m.p. 88–100° C. MH+=113; $^1$H NMR (D$_2$O): δ3.22–3.15 (m, 2H); 2.67–2.55 (m, 1H); 1.80–1.40 (m, 4H); 1.75 (s, 3H); 1.17 (d, J=7.2 Hz, 3H).

Elemental analysis: $C_6H_{12}N_2 \cdot CH_3COOH \cdot 3/4\ H_2O$

|  | C | H | N |
|---|---|---|---|
| Calculated: | 51.73 | 9.50 | 15.08 |
| Found: | 51.87 | 9.29 | 15.04 |

EXAMPLE 10

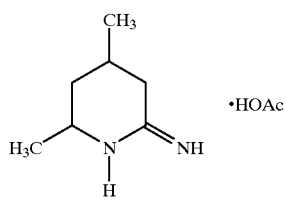

2-imino-4,6-dimethylpiperidine acetate

The method of preparation of 2-Imino-3-methylpiperidine acetate, EXAMPLE 6, was used to convert 2-amino-4,6-dimethylpyridine to the title compound which was obtained as a white solid. The analysis of the product was found to be consistent with the proposed structure. m.p. 163–166° C. MH+=127; $^1$H NMR (D$_2$O): δ3.48–3.40 (m, 1H); 2.52–2.40 (m, 1H); 2.07–1.95 (m, 1H); 1.85–1.75 (m, 2H); 1.75 (s, 3H); 1.12 (d, J=6.3 Hz, 3H); 1.02–0.92 (m, 1H); 0.86 (d, J=6.3 Hz, 3H).

Elemental analysis: C$_7$H$_{14}$N$_2$.CH$_3$COOH

|  | C | H | N |
|---|---|---|---|
| Calculated: | 58.04 | 9.74 | 15.04 |
| Found: | 57.86 | 10.09 | 15.01 |

EXAMPLE 11

2-Imino-3-hydroxypiperidine acetate

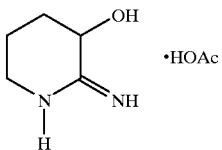

The method of preparation of 2-imino-3-methylpiperidine acetate, EXAMPLE 6, was used to convert 2-amino-3-hydroxypyridine to the title compound which was obtained as a white solid. The analysis of the product was found to be consistent with the proposed structure. m.p. 128–130° C. MH+=115; $^1$H NMR (D$_2$O): δ4.34–4.28 (m, 1H); 3.20–3.10 (m, 2H); 2.05–1.50 (m, 4H); 1.71 (S, 3H).

Elemental analysis: C$_7$H$_{10}$N$_2$O.CH$_3$COOH

|  | C | H | N |
|---|---|---|---|
| Calculated: | 48.27 | 8.10 | 16.08 |
| Found: | 48.04 | 8.48 | 15.96 |

Additional compounds of this invention include:

EXAMPLE 12

2-iminopyrrolidine hydrochloride; E. J. Moriconi and A. A. Cevasco, J. Org. Chem. 33, 2109–2111 (1968).

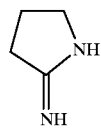

EXAMPLE 13

2-Iminopiperidine hydrochloride; Aldrich Chemical Co.

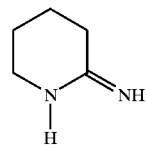

EXAMPLE 14

2-Iminotetrahydropyrimidine hemihydrosulfate; D. J. Brown and R. F. Evans, J. Chem. Soc. 4039–4045 (1962).

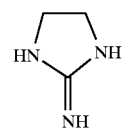

EXAMPLE 15

2-Iminoimidazolidine D. Stefanye and W. C. Howard, J. Amer. Chem. Soc., 77, 761–762 (1955).

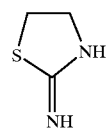

EXAMPLE 16

2-Iminothiazolidine hydrochloride; Aldrich Chemical Co.

EXAMPLE 17

2-Imino-3-thiapiperidine hydrochloride; D. L. Klayman and T. S. Woods, J. Org. Chem., 39, 1819–1823 (1974).

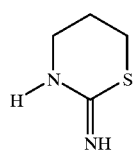

EXAMPLE 18

2-Imino-3-oxopiperidine hydrochloride; B. Adcock and A. Lawson, J. Chem.Soc. 474–479 (1965).

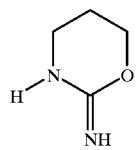

EXAMPLE 19

2-Iminooxazolidine; Transworld Chemical Inc.

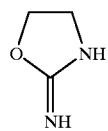

EXAMPLE 20

5-Chloromethyl-2-iminooxazolidine; Janssen Chimica.

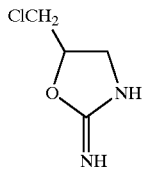

EXAMPLE 21

2-Iminobiotin; Sigma Chemical Co.

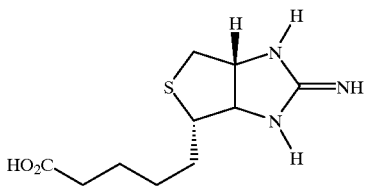

EXAMPLE 22

2-Iminobiotin ethyl ester

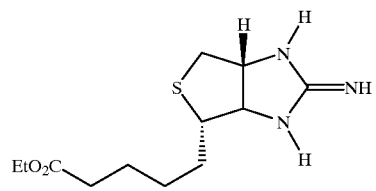

EXAMPLE 23

1-Methyl-2-iminotetrahydropyrimidine; GER 765,547

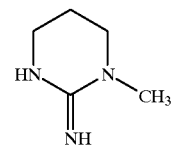

EXAMPLE 24

4-ethylcyclohexanone, oxime

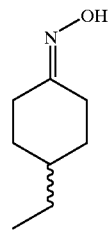

A sample of 4-ethylcyclohexanone (Aldrich, 4.9 g, 38.8 mmol) was combined with $NH_2OH \cdot HCl$ (4.0 g, 58.3 mmol) and sodium acetate (NaOAc, 5.7 g, 69.8 mmol) in a mixture of ethanol (EtOH, 35 mL) and water (25 mL). This mixture was refluxed for 5 h under a nitrogen atmosphere. After the reaction was cooled to room temperature and stirred for an additional 5 days, all solvent was removed under reduced pressure. The residue was partitioned between ethyl acetate (EtOAc) and water and the organic phase was washed with 1×75 mL of saturated NaCl (brine), dried over $Na_2SO_4$, and stripped of all solvent under reduced pressure. This provided 5.5 g (100%) of the title compound as light yellow mobile oil. This material showed a retention time of 9.83 min (100% purity by peak area integration) on a Shimadzu GC-14A gas chromatograph (GC) with a 0.25 mm×25 M methyl, 5% phenylsilicone column and NMR and IR spectra consistent with the assigned structure.

Elemental analysis: $C_8H_{15}NO \cdot H_2O$ (MW=159.23)

|  | C | H | N |
|---|---|---|---|
| Calculated: | 60.35 | 10.76 | 8.80 |
| Found: | 60.64 | 9.25 | 8.41 |

EXAMPLE 25

5-ethyl-hexahydro-1H-azepin-2-one

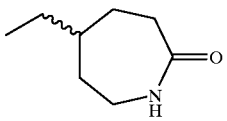

A 5.3 g (37.7 mmol) sample of the title material of EXAMPLE 24 was added to a dropping funnel containing 6 mL of 80% $H_2SO_4$. After using a stirring rod to obtain a turbid solution, this mixture was added dropwise (10 min) to 5 mL of 80% $H_2SO_4$ stirred magnetically and maintained at 120° C. with an external oil bath. Within 5 minutes of the start of addition an exotherm was noted and the temperature of the reaction rose to 160° C. before cooling again to 120° C. Ten minutes later the flask was removed from the bath and allowed to cool to room temperature. The product mixture was diluted with water (20 mL) and brought to pH 6 with concentrated $NH_4OH$. This solution was further diluted with 75 mL of water and extracted with 3×75 mL of $CH_2Cl_2$. The combined organic phase was washed with 1×50 mL of brine, dried ($Na_2SO_4$), filtered, and stripped of all solvent under reduced pressure. The oily residue was purified by HPLC on silica gel to yield 3.73 g (70%) of the title product as a cream colored solid. This material had a GC retention time of 13.17 min and peak area integration of 100% under conditions identical to those used for the product of EXAMPLE 24.

Elemental analysis: $C_8H_{15}NO.0.05\ H_2O$ (MW=142.12)

|  | C | H | N |
|---|---|---|---|
| Calculated: | 67.61 | 10.71 | 9.86 |
| Found: | 67.47 | 10.67 | 9.90 |

EXAMPLE 26

4-ethyl-3,4,5,6-tetrahydro-7-methoxy-2H-azepine

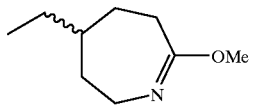

To a magnetically stirred slurry of trimethyloxonium tetrafluoroborate (Lancaster, 0.62 g, 4.2 mmol) in $CH_2Cl_2$ (15 mL) under argon (Ar) was added the title product of EXAMPLE 25 (0.50 g, 3.5 mmol). This mixture was stirred at room temperature for 12 h before it was diluted with 10 mL of $CH_2Cl_2$ and partitioned between 40 mL of saturated $KHCO_3$ and 50 mL of EtOAc. The organic phase was separated, dried over $Na_2SO_4$, filtered, and stripped of all solvent under reduced pressure to provide the crude title product as a pale yellow oil. This material was chromatographed on a short path Merck flash silica column eluting with EtOAc/n-hexane (1:1). The title pale yellow liquid product had a GC retention time of 8.56 min (100%) and NMR and IR sprectra consistent with the indicated product.

EXAMPLE 27

5-ethyl-hexahydro-1H-azepin-2-imine, monohydrochloride

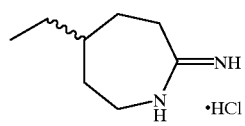

The title product of EXAMPLE 26 (0.28 g, 1.80 mmol) and 0.11 g (2.0 mmol) of ammonium chloride ($NH_4Cl$) were refluxed in 20 mL of methanol (MeOH) under a nitrogen atmosphere for 3.5 h. After cooling the reaction to room temperature, it was filtered, stripped of all solvent under reduced pressure, and partitioned between 20 mL of water and 25 mL of EtOAc. The organic and aqueous phases were separated and the aqueous phase was washed with another 25 mL portion of EtOAc before it was lyophilized to provide 0.27 g (80%) of the white solid title material.

HRMS (EI) calcd for $C_8H_{16}N_2$ m/e 140.131, found m/e 140.131. $^1$H NMR(CD3OD) δ3.50–3.36 (m, 2H), 2.79–2.60 (m, 2H), 1.99–2.08 (m, 1H), 1.96–1.87 (m, 1H), 1.56 (m, 1H), 1.36 (m, 2H) 1.27–1.12 (m, 2H), 0.94 (t, 3H, J=7.5 Hz).

Elemental analysis: $C_8H_{16}N_2.HCl.0.1\ H_2O.0.2\ NH_4Cl$ (MW=189.19)

|  | C | H | N | Cl |
|---|---|---|---|---|
| Calculated: | 50.79 | 9.59 | 16.26 | 22.49 |
| Found: | 50.71 | 9.48 | 16.30 | 22.45 |

EXAMPLE 28

4-phenylcyclohexanone, oxime

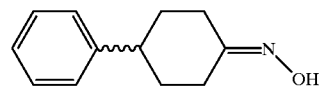

A sample of 4-phenylcyclohexanone (Aldrich, 10.0 g, 57.4 mmol) was converted to the title compound by the method of EXAMPLE 24 using 6.0 g (86.1 mmol) of hydroxylamine hydrochloride and 8.5 g (103.3 mmol) of NaOAc in a mixture of 75 mL of EtOH and 50 mL of water. The procedure produced 10.2 g (94%) of the title material as a white solid.

Elemental analysis: $C_{12}H_{15}NO$ (MW=189.26)

|  | C | H | N |
|---|---|---|---|
| Calculated: | 76.16 | 7.99 | 7.40 |
| Found: | 75.96 | 7.89 | 7.33 |

EXAMPLE 29 hexahydro-5-phenyl-1H-azepin-2-one

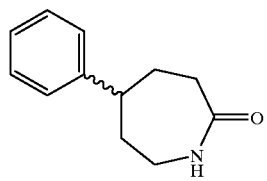

To the title product of EXAMPLE 28 (9.0 g, 47.6 mmol) in 50 mL of acetone was added 1N NaOH (52.4 mL, 52.4 mmol). After cooling this mixture in an ice bath, benzene sulfonylchloride (8.5 g, 48.0 mmol) was added drop-wise over 5 minutes to the stirred reaction mixture maintained under a $N_2$ atmosphere. The reaction was allowed to warm to room temperature and stir for 1 week. A white solid was filtered from the reaction mixture and washed with acetone to yield 4.2 g of the title material. The filtrate was concentrated and partitioned between EtOAc and brine. The organic layer was dried ($Na_2SO_4$), filtered, and stripped of all solvent under reduced pressure. The residue solid was triturated with EtOAc/n-hexane (1:1) and filtered to provide an additional 2.9 g (total yield=80%) of the title lactam.

Elemental analysis: $C_{12}H_{15}NO$ (MW=189.26)

|  | C | H | N |
|---|---|---|---|
| Calculated: | 76.16 | 7.99 | 7.40 |
| Found: | 75.95 | 8.16 | 7.28 |

EXAMPLE 30

3,4,5,6,-tetrahydro-7-methoxy-4-phenyl-2H-azepine

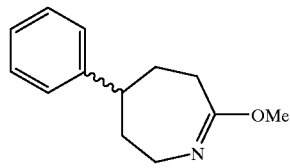

The product of EXAMPLE 29 (2.0 g, 10.5 mmol) was reacted with trimethyloxonium tetrafluoroborate (2.0 g, 13.6 mmol) by the method of EXAMPLE 26 to yield 1.9 g (89%) of the title material.

Elemental analysis: $C_{13}H_{17}NO.0.5\ H_2O$ (MW=209.23)

|  | C | H | N |
|---|---|---|---|
| Calculated: | 74.63 | 8.51 | 6.69 |
| Found: | 74.77 | 8.14 | 6.65 |

EXAMPLE 31 hexahydro-5-phenyl-1H-azepin-2-imine, monohydrochloride

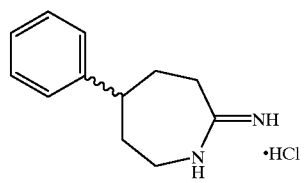

The product of EXAMPLE 30 (1.7 g, 8.6 mmol) in 20 mL of MeOH was reacted with ammonium chloride (0.43 g, 8.0 mmol) by the method of EXAMPLE 27 to yield 1.7 g (91%) of the title material.

HRMS (EI) calcd for $C_{12}H_{16}N_2$ m/e 188.131, found m/e 188.133. $^1$H NMR($CD_3OD$): δ7.33–7.26 (m, 2H), 7.25–7.17 (m, 3H), 3.60–3.53 (m, 2H), 2.98–2.87 (m, 2H), 2.78–2.69 (m, 1H), 2.17–2.08 (m, 1H), 2.05–1.98 (m, 1H), 1.80–1.69 (m, 2H).

Elemental analysis: $C_{12}H_{16}N_2.HCl.0.33\ H_2O$ (MW=230.68)

|  | C | H | N | Cl |
|---|---|---|---|---|
| Calculated: | 62.48 | 7.72 | 12.14 | 15.37 |
| Found: | 62.41 | 7.54 | 12.13 | 15.63 |

EXAMPLE 32

3,5-dimethylcyclohexanone, oxime

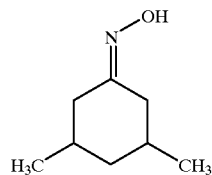

A sample of 3,5-dimethylcyclohexanone (TCI, 22.6 g, 180 mmol) was converted to the title compound by the method of EXAMPLE 24 using 18.7 g (270 mmol) of hydroxylamine hydrochloride and 26.6 g (324 mmol) of NaOAc in a mixture of 200 mL of EtOH and 110 mL of water. The procedure produced 23.1 g (94%) of the title material as a white solid.

Elemental analysis: $C_8H_{15}NO.0.1\ H_2O$ (MW=143.02)

|  | C | H | N |
|---|---|---|---|
| Calculated: | 67.19 | 10.71 | 9.79 |
| Found: | 67.37 | 10.52 | 9.78 |

EXAMPLE 33 hexahydro-4,6-dimethyl-1H-azepine-2-one

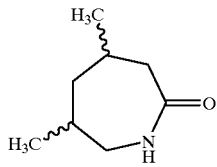

A sample of the product of EXAMPLE 32 (10.0 g, 69.9 mmol) was converted to the title compound as a mixture of two diastereomeric pairs by the method of EXAMPLE 25 using 22 mL of 80% $H_2SO_4$. The procedure produced 8.4 g (85%) of the title material as a pale yellow tacky solid.

Elemental analysis: $C_8H_{15}NO$ (MW=141.21)

|  | C | H | N |
|---|---|---|---|
| Calculated: | 68.04 | 10.71 | 9.92 |
| Found: | 67.92 | 10.04 | 9.83 |

EXAMPLE 34

3,4,5,6-tetrahydro-7-methoxy-3,5-dimethyl-2H-azepine

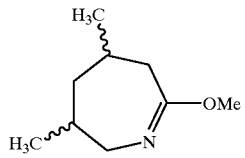

The product of EXAMPLE 33 (2.0 g, 14.2 mmol) was reacted with trimethyloxonium tetrafluoroborate (2.7 g, 18.4 mmol) by the method of EXAMPLE 26 to yield 1.9 g (73%) of the title material.

Elemental analysis: $C_9H_{17}NO.0.125$ $H_2O$ (MW=157.49)

|  | C | H | N |
|---|---|---|---|
| Calculated: | 68.64 | 11.04 | 8.89 |
| Found: | 68.66 | 11.14 | 8.87 |

EXAMPLE 35 hexahydro-4,6-dimethyl-1H-azepin-2-imine, monohydrochloride

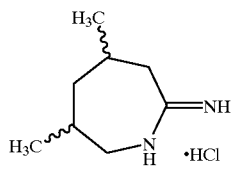

The product of EXAMPLE 34 (1.75 g, 8.6 mmol) in 25 mL of MeOH was reacted with ammonium chloride (0.48 g, 9.0 mmol) by the method of EXAMPLE 27 to yield 1.4 g (83%) of the title material.

HRMS (EI) calcd for $C_8H_{16}N_2$ m/e 140.131, found m/e 140.130. $^1$H NMR($CD_3OD$): δ3.26–3.18 (m, 1H), 2.42 (m, 1H), 1.91 (m, 1H), 1.85–1.62 (m, 2H), 1.09 (d, 3H, J=6.8 Hz), 0.95 (d, 3H, J=6.8 Hz).

Elemental analysis: $C_8H_{16}N_2.HCl0.25$ $H_2O$ (MW=181.195)

|  | C | H | N | Cl |
|---|---|---|---|---|
| Calculated: | 53.03 | 9.74 | 15.46 | 19.57 |
| Found: | 53.19 | 9.85 | 15.46 | 19.26 |

EXAMPLE 36

2,6-dimethylcyclohexanone, oxime

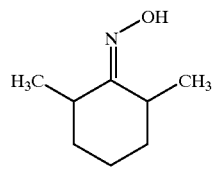

A sample of 2,6-dimethylcyclohexanone (Aldrich, 20.0 g, 158.5 mmol) was converted to the title compound by the method of EXAMPLE 24 using 16.5 g (237.6 mmol) of hydroxylamine hydrochloride and 23.4 g (285.1 mmol) of NaOAc in a mixture of 150 mL of EtOH and 100 mL of water. The procedure produced 20.3 g (88%) of the title material as a white crystalline solid.

Elemental analysis: $C_8H_{15}NO.0.25$ $H_2O$ (MW=145.72)

|  | C | H | N |
|---|---|---|---|
| Calculated: | 65.94 | 10.72 | 9.61 |
| Found: | 65.74 | 10.45 | 9.67 |

EXAMPLE 37 hexahydro-3,7-dimethyl-1H-azepin-2-one

Diastereomeric pair-A and Diastereomeric pair-B

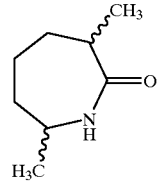

A sample of the product of EXAMPLE 36 (8.14 g, 57.6 mmol) was converted to the title mixture of two diastereomeric pairs by the method of EXAMPLE 25 using 15 mL of 80% $H_2SO_4$. Normal phase silica gel chromatography was used to separate the two diastereomeric pairs by elution with 3–10% isopropanol/n-heptane. The procedure generated 3.3 g (41%) of the title enantiomeric pair-A eluting first from the column and 1.05 g (13%) material of the title enantiomeric pair-B eluting second from the column both as white solids.

Enantiomeric Pair-A:

Elemental analysis: $C_8H_{15}NO\cdot0.05\ H_2O$ (MW=142.12)

|  | C | H | N |
|---|---|---|---|
| Calculated: | 67.61 | 10.71 | 9.86 |
| Found: | 67.83 | 10.71 | 9.87 |

Enantiomeric Pair-B:

Elemental analysis: $C_8H_{15}NO$ (MW=141.214)

|  | C | H | N |
|---|---|---|---|
| Calculated: | 68.04 | 10.71 | 9.92 |
| Found: | 68.94 | 10.88 | 9.43 |

EXAMPLE 38

3,4,5,6-tetrahydro-7-methoxy-2,6-dimethyl-2H-azepine

Enantiomeric pair-A

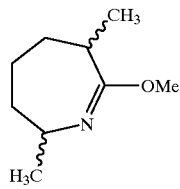

Enantiomeric pair-A of EXAMPLE 37 (2.0 g, 14.1 mmol) was reacted with trimethyloxonium tetrafluoroborate (2.7 g, 18.4 mmol) by the method of EXAMPLE 26 to yield 1.9 g (86%) of the title material as a clear volatile liquid.

EXAMPLE 39 hexahydro-3,7-dimethyl-1H-azepin-2-imine, monohydrochloride

Enantiomeric pair-A

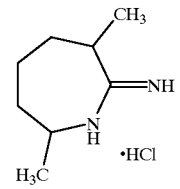

The product of EXAMPLE 38 (1.24 g, 8.0 mmol) in 25 mL of MeOH was reacted with ammonium chloride (0.37 g, 6.8 mmol) by the method of EXAMPLE 27 to yield 1.23 g (91%) of the title material.

MS (EI) calcd for $C_8H_{16}N_2$ m/e 140.131, found m/e 140 (100%). $^1$H NMR($CD_3OD$): δ3.89–3.79 (m, 1H), 3.10–3.00 (m, 1H), 1.98–1.90 (m, 1H), 1.87–1.75 (m, 3H), 1.54–1.32 (m, 2H), 1.32 (d, 3H, J=6.7 Hz), 1.26 (d, 3H, J=7.0 Hz).

Elemental analysis: $C_8H_{16}N_2\cdot HCl\cdot0.125\ H_2O\cdot0.05\ NH_4Cl$ (MW=181.62)

|  | C | H | N | Cl |
|---|---|---|---|---|
| Calculated: | 52.91 | 9.68 | 15.81 | 20.50 |
| Found: | 52.89 | 9.63 | 15.49 | 20.76 |

EXAMPLE 40

3,4,5,6-tetrahydro-7-methoxy-2,6-dimethyl-2H-azepine

Enantiomeric pair-B

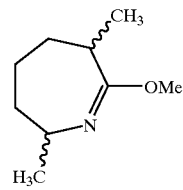

Enantiomeric pair-B of EXAMPLE 37 (510 mg, 3.6 mmol) was reacted with trimethyloxonium tetrafluoroborate (694 mg, 4.7 mmol) by the method of EXAMPLE 26 to yield 480 mg (86%) of the title material as a clear volatile liquid.

EXAMPLE 41 hexahydro-3,7-dimethyl-1H-azepin-2-imine, monohydrochloride

Enantiomeric pair-B

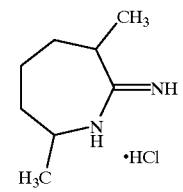

The product of EXAMPLE 40 (380 mg, 2.4 mmol) in 15 mL of MeOH and 5 mL of $CH_2Cl_2$ was reacted with ammonium chloride (104 mg, 2.0 mmol) by the method of EXAMPLE 27 to yield 368 mg (100%) of the title material.

MS (EI) calcd for $C_8H_{16}N_2$ m/e 140.131, found m/e 140.132 (100%). $^1$H NMR($CD_3OD$): δ3.85 (m, 1H), 3.00 (m, 1H), 1.95–1.70 (m, 5H), 1.42 (m, 1H), 1.40 (d, 3H, J=7 Hz), 1.30 (d, 3H, J=6 Hz)

Elemental analysis: $C_8H_{16}N_2\cdot HCl\cdot0.1\ H_2O\cdot0.1\ NH_4Cl$ (MW=183.84)

|  | C | H | N | Cl |
|---|---|---|---|---|
| Calculated: | 52.27 | 9.65 | 16.00 | 21.21 |
| Found: | 52.44 | 10.16 | 15.85 | 21.23 |

EXAMPLE 42

2-methylcyclohexanone, oxime

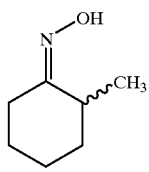

A sample of 2-methylcyclohexanone (Aldrich, 11.2 g, 100.0 mmol) was converted to the title compound by the method of EXAMPLE 24 using 13.9 g (200.0 mmol) of hydroxylamine hydrochloride and 17.2 g (210.0 mmol) of NaOAc in a mixture of 160 mL of EtOH and 160 mL of water. The procedure produced 10.1 g (79%) of the title material as a white solid.

EXAMPLE 43 hexahydro-3-methyl-1H-azepin-2-one, mixture with hexahydro-7-methyl-1H-azepin-2-one

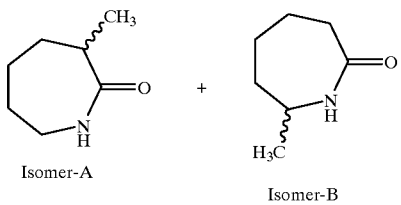

Isomer-A    Isomer-B

A sample of the product of EXAMPLE 42 (5.1 g, 40.0 mmol) was converted to the title compound mixture of two regioisomers by the method of EXAMPLE 25 using 10 mL of 80% $H_2SO_4$. The procedure produced 3.1 g (62%) of the title materials. This mixture was subjected to silica gel chromatography eluting with 3–7% isopropanol/n-heptane to obtain Isomer-A (525 mg) and Isomer-B (735 mg).

EXAMPLE 44

3,4,5,6-tetrahydro-7-methoxy-6-methyl-2H-azepine

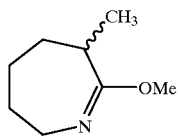

The Isomer-A product of EXAMPLE 43 (511 mg, 4.1 mmol) was reacted with trimethyloxonium tetrafluoroborate (227 mg, 5.5 mmol) by the method of EXAMPLE 26 to yield, after chromatography, 505 mg (87%) of the title material.

EXAMPLE 45

3,4,5,6-tetrahydro-7-methoxy-2-methyl-2H-azepine

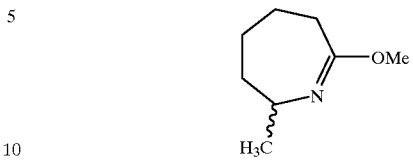

The Isomer-B product of EXAMPLE 43 (762 mg, 6.0 mmol) was reacted with trimethyloxonium tetrafluoroborate (1.15 g, 7.8 mmol) by the method of EXAMPLE 26 to yield, after chromatography, 780 mg (92%) of the title material.

EXAMPLE 46 hexahydro-3-methyl-1H-azepin-2-imine, monohydrochloride

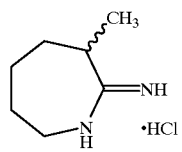

The product of EXAMPLE 44 (294 mg, 2.1 mmol) in 14.5 mL of MeOH was reacted with ammonium chloride (103 mg, 2.0 mmol) by the method of EXAMPLE 27 to yield 260 mg (77%) of the title material.

MS (EI) calcd for $C_7H_{14}N_2$ m/e 126.116, found m/e 126 (100%). $^1$H NMR(CD$_3$OD): δ3.51–3.42 (m, 2H), 3.06–3.00 (m, 1H), 1.99–1.93 (m, 1H), 1.82–1.73 (m, 3H), 1.61–1.50 (m, 2H), 1.30 (d, 3H, J=7.14 Hz).

Elemental analysis: $C_7H_{14}N_2 \cdot HCl \cdot 0.2\ H_2O \cdot 0.1\ NH_4Cl$ (MW=171.62)

|  | C | H | N | Cl |
| --- | --- | --- | --- | --- |
| Calculated: | 48.99 | 9.28 | 17.14 | 22.72 |
| Found: | 48.95 | 9.60 | 17.29 | 22.59 |

EXAMPLE 47 hexahydro-7-methyl-1H-azepin-2-imine, monohydrochloride

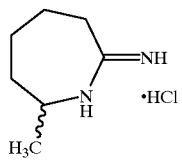

The product of EXAMPLE 45 (125 mg, 0.89 mmol) in 9.0 mL of MeOH was reacted with ammonium chloride (44.0 mg, 0.83 mmol) by the method of EXAMPLE 27 to yield 101 mg (63%) of the title material.

MS (EI) calcd for $C_7H_{14}N_2$ m/e 126.116, found m/e 126 (100%). $^1$H NMR(CD$_3$OD): δ3.77 (m, 1H), 2.77 (ddd, 1H), 2.62 (m, 1H), 2.03–1.95 (m, 2H), 1.84 (m, 1H), 1.7 (m, 3H), 1.51–1.35 (m, 2H), 1.32 (d, 3H, J=6.84 Hz).

Elemental analysis: $C_7H_{14}N_2 \cdot HCl \cdot 0.33\ H_2O \cdot 0.21\ NH_4Cl$ (MW=179.84)

|  | C | H | N | Cl |
|---|---|---|---|---|
| Calculated: | 46.75 | 9.25 | 17.21 | 23.85 |
| Found: | 46.53 | 9.45 | 17.29 | 24.25 |

EXAMPLE 48

3-(trifluoromethyl)cyclohexanone, oxime

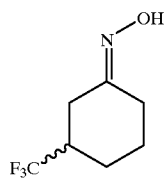

A sample of 3-trifluoromethylcyclohexanone (Aldrich, 3.3 g, 20.0 mmol) was converted to the title compound by the method of EXAMPLE 24 using 2.8 g (40.0 mmol) of hydroxylamine hydrochloride and 3.4 g (42.0 mmol) of NaOAc in a mixture of 30 mL of EtOH and 30 mL of water. The procedure provided 2.9 g (80%) of the title material as a white solid.

EXAMPLE 49 hexahydro-4-(trifluoromethyl)-1H-azepin-2-one, mixture with hexahydro-6-(trifluoromethyl)-1H-azepin-2-one

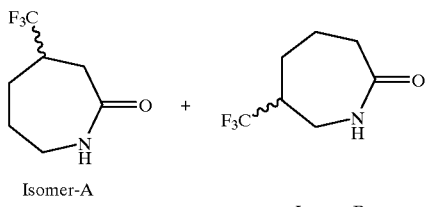

A sample of the product of EXAMPLE 48 (2.3 g, 12.5 mmol) was converted to the title compound mixture of two regioisomers by the method of EXAMPLE 25 using 4 mL of 80% $H_2SO_4$. The procedure produced 795 mg (36%) of the title materials. This mixture of 80% Isomer-A was subjected to reverse phase HPLC eluting with acetonitrile/water to obtain only Isomer-A (330 mg).

EXAMPLE 50 hexahydro-4-(trifluoromethyl)-1H-azepin-2-one, mixture with hexahydro-6-(trifluoromethyl)-1H-azepin-2-one

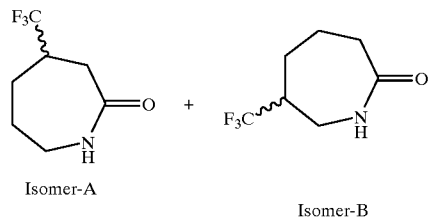

A sample of 3-trifluoromethylcyclohexanone (Aldrich, 1.7 g, 10.0 mmol) was added dropwise to a stirred mixture of 12 mL of conc $H_2SO_4$ and 4 mL of $CH_2Cl_2$. To this mixture, maintained at 0–10° C., was added 0.8 g (0.12 mmol) of sodium azide portionwise over 1 hr. After the reaction had warmed to room temperature and stirred overnight, it was poured into 50 mL of ice water and the mixture was extracted with $CHCl_3$ (50mL). The organic layer was washed with water, dried ($Na_2SO_4$), filtered, and concentrated to the crude title mixture that was 63% Isomer-B. This material was subjected to reverse phase HPLC eluting with acetonitrile/water to obtain only Isomer-B (438 mg).

EXAMPLE 51

3,4,5,6-tetrahydro-7-methoxy-5-(trifluoromethyl)-2H-azepine

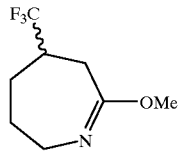

The Isomer-A product of EXAMPLE 49 (457 mg, 2.5 mmol) was reacted with trimethyloxonium tetrafluoroborate (484 mg, 3.3 mmol) by the method of EXAMPLE 26 to yield, after chromatography, 430 mg (87%) of the title material.

EXAMPLE 52

3,4,5,6-tetrahydro-7-methoxy-3-(trifluoromethyl)-2H-azepine

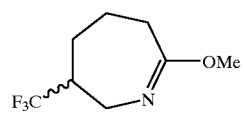

The Isomer-B product of EXAMPLE 50 (350 mg, 1.9 mmol) was reacted with trimethyloxonium tetrafluoroborate (371 mg, 2.5 mmol) by the method of EXAMPLE 26 to yield, after chromatography, 280 mg (76%) of the title material.

EXAMPLE 53 hexahydro-4-(trifluoromethyl)-1H-azepin-2-imine, monohydrochloride

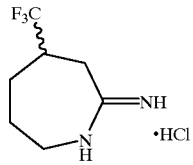

The product of EXAMPLE 51 (240 mg, 1.2 mmol) in 7.0 mL of MeOH was reacted with ammonium chloride (66.0 mg, 1.2 mmol) by the method of EXAMPLE 27 to yield 265 mg (94%) of the title material.

HRMS (EI) calcd for $C_7H_{11}N_2F_3$ m/e 180.087, found m/e 180.087. $^1$H NMR(CD$_3$OD): δ1.63 (m, 1H), 1.79 (M, 1H), 1.99 (m, 1H), 2.22 (m, 1H), 2.63 (m, 1H), 2.86 (dt, 1H), 2.98 (dd, 1H), 3.42–3.46 (m,2H).

Elemental analysis: $C_7H_{11}N_2F_3 \cdot HCl \cdot 0.125H_2) \cdot 0.2\,NH_4Cl$ (MW=229.59)

|  | C | H | N | Cl |
|---|---|---|---|---|
| Calculated: | 36.62 | 5.73 | 13.42 | 18.53 |
| Found: | 36.93 | 5.51 | 13.19 | 18.41 |

EXAMPLE 54 hexahydro-6-(trifluoromethyl)-1H-azepin-2-imine, monohydrochloride

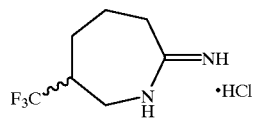

The product of EXAMPLE 52 (77 mg, 0.39 mmol) in 3.0 mL of MeOH was reacted with ammonium chloride (21.0 mg, 0.39 mmol) by the method of EXAMPLE 27 to yield 83 mg (94%) of the title material.

HRMS (EI) calcd for $C_7H_{11}N_2F_3$ m/e 180.087, found m/e 180.087. $^1$H NMR(CD$_3$OD): δ3.7 (m, 1H), 3.57–3.66 (m, 1H), 2.85 (ddd, 1H), 2.75 (ddd, 1H), 2.53 (m, 1H), 2.2 (m, 1H), 2.1 (m, 1H), 1.84 (m, 1H), 1.70 (m, 1H).

Elemental analysis: $C_7H_{11}N_2F_3 \cdot HCl \cdot 0.2\,H_2O + 0.1\,NH_4Cl$ (MW=225.59)

|  | C | H | N | Cl |
|---|---|---|---|---|
| Calculated: | 37.27 | 5.72 | 13.04 | 17.29 |
| Found: | 37.21 | 5.47 | 12.72 | 16.93 |

EXAMPLE 55

2-ethylcyclohexanone, oxime

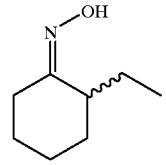

A sample of 2-ethylcyclohexanone (Pfaltz & Bauer, 9.5 g, 75.0 mmol) was converted to the title compound by the method of EXAMPLE 24 using 10.4 g (150 mmol) of hydroxylamine hydrochloride and 12.6 g (153.7 mmol) of NaOAc in a mixture of 120 mL each of EtOH and water. The procedure produced 9.8 g (93%) of the title material as a white solid.

EXAMPLE 56

7-ethyl-hexahydro-1H-azepin-2-one, mixture with 3-ethyl-hexahydro-1H-azepin-2-one

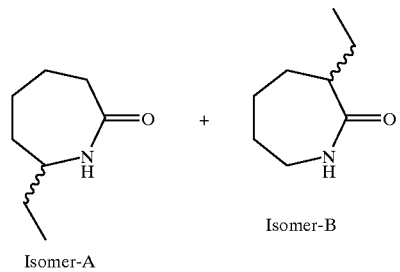

A sample of the product of EXAMPLE 55 (4.9 g, 34.3 mmol) was converted to the title compound mixture of two regioisomers by the method of EXAMPLE 25 using 11 mL of 80% $H_2SO_4$. The procedure produced 7.2 g (73%) of the title materials as a pale yellow liquid. This mixture was separated into its components by chromatography to yield 2.1 g of isomer-A and 1.1 g of isomer-B.

EXAMPLE 57

2-ethyl-3,4,5,6-tetrahydro-7-methoxy-2H-azepine

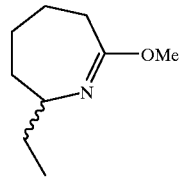

The Isomer-A product of EXAMPLE 56 (938 mg, 6.65 mmol) was reacted with trimethyloxonium tetrafluoroborate (1.28 g, 8.6 mmol) by the method of EXAMPLE 26 to yield, after chromatography, 802 mg (78%) of the title material.

EXAMPLE 58

6-ethyl-3,4,5,6-tetrahydro-7-methoxy-2H-azepine

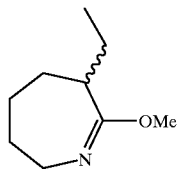

The Isomer-B product of EXAMPLE 56 (700 mg, 5.0 mmol) was reacted with trimethyloxonium tetrafluoroborate (955 mg, 6.4 mmol) by the method of EXAMPLE 26 to yield, after chromatography, 613 mg (89%) of the title material.

EXAMPLE 59

7-ethyl-hexahydro-1H-azepin-2-imine, monohydrochloride

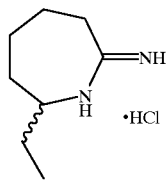

The product of EXAMPLE 57 (802 mg, 5.2 mmol) in 15 mL of MeOH was reacted with ammonium chloride (225 mg, 4.2 mmol) by the method of EXAMPLE 27 to yield 627 mg (82%) of the title material.

HRMS (EI) calcd for $C_8H_{16}N_2$ m/e 140.131, found m/e 140.131. $^1$H NMR(CD$_3$OD): δ3.57–3.51 (m, 1H), 2.82–2.75 (m, 1H), 2.65–2.60 (m, 1H), 2.03–1.97 (m, 2H), 1.89–1.83 (m, 1H), 1.72–1.62 (m, 3H), 1.54–1.47 (m, 1H), 1.41–1.32 (m, 1H), 1.05–1.01 (t, 3H, J=7.45 HZ)).

Elemental analysis: $C_8H_{16}N_2 \cdot HCl \cdot 0.1\ H_2O + 0.01\ NH_4Cl$ (MW=179.03)

|             | C     | H     | N     | Cl    |
|-------------|-------|-------|-------|-------|
| Calculated: | 53.67 | 9.71  | 15.85 | 20.06 |
| Found:      | 53.62 | 10.13 | 15.86 | 20.02 |

EXAMPLE 60

3-ethyl-hexahydro-1H-azepin-2-imine, monohydrochloride

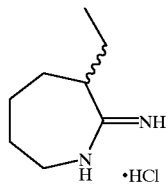

The product of EXAMPLE 58 (600 mg, 3.9 mmol) in 20 mL of MeOH was reacted with ammonium chloride (165 mg, 3.1 mmol) by the method of EXAMPLE 27 to yield 512 mg (93%) of the title material.

HRMS (EI) calcd for $C_8H_{16}N_2$ m/e 140.131, found m/e 140.132. $^1$H NMR(CD$_3$OD): δ3.48–3.30 (m, 2H), 2.76–2.74 (m, 1H), 1.90–1.71 (m, 4H), 1.70–1.64 (m, 4H), 1.05–1.02 (m, 3H).

Elemental analysis: $C_8H_{16}N_2 \cdot HCl \cdot 0.2\ H_2O + 0.01\ NH_4Cl$ (MW=180.83)

|             | C     | H     | N     | Cl    |
|-------------|-------|-------|-------|-------|
| Calculated: | 53.14 | 9.72  | 15.57 | 19.80 |
| Found:      | 52.98 | 10.46 | 15.60 | 20.04 |

EXAMPLE 61

3,3-dimethylcyclohexanone, oxime

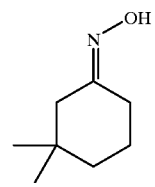

A sample of 3,3-dimethylcyclohexanone (Wiley, 18.9 g, 150.0 mmol) was converted to the title compound by the method of EXAMPLE 24 using 20.7 g (300.0 mmol) of hydroxylamine hydrochloride and 25.2 g (307.5 mmol) of NaOAc in a mixture of 400 mL of EtOH and 400 mL of water. The procedure produced 16.2 g (77%) of the title material as a pale yellow oil.

EXAMPLE 62 hexahydro-6,6-dimethyl-1H-azepin-2-one, mixture with hexahydro-4,4-dimethyl-1H-azepin-2-one

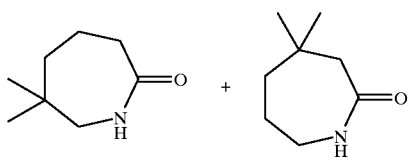

Isomer-A      Isomer-B

A sample of the product of EXAMPLE 61 (7.1 g, 50.0 mmol) was converted to the title compound mixture of two regioisomers by the method of EXAMPLE 25 using 12.5 mL of 80% H$_2$SO$_4$. The procedure produced 6.2 g (87%) of the title materials as a light brown solid. This mixture was separated into its components by chromatography to yield 1.4 g of isomer-A and 1.8 g of isomer-B.

EXAMPLE 63

3,4,5,6-tetrahydro-7-methoxy-3,3-dimethyl-2H-azepine

The Isomer-A product of EXAMPLE 62 (985 mg, 7.0 mmol) was reacted with trimethyloxonium tetrafluoroborate (1.3 g, 9.1 mmol) by the method of EXAMPLE 26 to yield, after chromatography, 525 mg (48%) of the title material.

EXAMPLE 64

3,4,5,6-tetrahydro-7-methoxy-5,5-dimethyl-2H-azepine

The Isomer-B product of EXAMPLE 62 (437 mg, 3.1 mmol) was reacted with trimethyloxonium tetrafluoroborate (573 mg, 3.9 mmol) by the method of EXAMPLE 26 to yield, after chromatography, 265 mg (55%) of the title material.

EXAMPLE 65 hexahydro-6,6-dimethyl-1H-azepin-2-imine, monohydrochloride

The product of EXAMPLE 63 (490 mg, 3.2 mmol) in 18 mL of MeOH was reacted with ammonium chloride (125 mg, 2.4 mmol) by the method of EXAMPLE 27 to yield 387 mg (69%) of the title material.

MS (EI) calcd for $C_8H_{16}N_2$ m/e 140.131, found m/e 140 (100%). $^1$H NMR(CD$_3$OD): δ5.80–5.72 (m, 2H), 5.62–5.58 (m, 2H), 3.2 (s, 2H), 2.68–2.63 (m, 2H), 0.95(s, 6H).

Elemental analysis: $C_8H_{16}N_2$.HCl (MW=176.69)

|  | C | H | N | Cl |
|---|---|---|---|---|
| Calculated: | 54.38 | 9.70 | 15.85 | 20.06 |
| Found: | 54.57 | 9.58 | 15.17 | 19.61 |

EXAMPLE 66 hexahydro-4,4-dimethyl-1H-azepin-2-imine, monohydrochloride

The product of EXAMPLE 64 (260 mg, 1.7 mmol) in 10 mL of EtOH was reacted with ammonium chloride (88 mg, 1.7 mmol) by the method of EXAMPLE 27 to yield 185 mg (55%) of the title material.

HRMS (EI) calcd for $C_8H_{16}N_2$ m/e 140.131, found m/e 140.132. $^1$H NMR(CD$_3$OD): δ3.42–3.39 (m, 2H), 2.62 (s, 2H), 1.75–1.65 (m, 4H), 1.07 (s, 6H).

Elemental analysis: $C_8H_{16}N_2$.HCl.0.2 $H_2O$.0.32 $NH_4Cl$ (MW=197.26)

|  | C | H | N | Cl |
|---|---|---|---|---|
| Calculated: | 48.71 | 9.47 | 16.47 | 23.72 |
| Found: | 48.68 | 9.41 | 16.49 | 24.04 |

EXAMPLE 67

4-methylcyclohexanone, oxime

A sample of 4-methylcyclohexanone (Aldrich, 5.0 g, 44.6 mmol) was converted to the title compound by the method of EXAMPLE 24 using 4.6 g (66.9 mmol) of hydroxylamine hydrochloride and 6.2 g (75.8 mmol) of NaOAc in a mixture of 25 mL of EtOH and 25 mL of water. The procedure produced 4.8 g (84%) of the title material as a pale yellow oil.

EXAMPLE 68 hexahydro-5-methyl-1H-azepin-2-one

A sample of the product of EXAMPLE 67 (4.0 g, 31.4 mmol) was converted to the title compound by the method of EXAMPLE 25 using 10 mL of 80% $H_2SO_4$. The procedure produced 3.2 g (80%) of the title material as a yellow oil.

EXAMPLE 69

3,4,5,6-tetrahydro-7-methoxy-4-methyl-2H-azepine

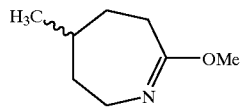

The product of EXAMPLE 68 (2.5 g, 19.7 mmol) dissolved in 25 mL of benzene was dried by refluxing the mixture through a Dean-Stark trap for 30 minutes. To this mixture was added dimethylsulfate (1.4 mL, 19.7 mmol) and the heating was continued for an additional 17 hours. After cooling to room temperature, the reaction was diluted with EtOAc (50 mL) and washed with 50 mL of saturated $NaHCO_3$. The aqueous layer was extracted with 2×100 mL EtOAc and the combined organic phase was dried ($Na_2SO_4$), filtered, and stripped of all solvent under reduced pressure to yield a mixture of two immiscible oils. The top lighter phase (1.6 g, 58%) was separated and identified as the title material.

EXAMPLE 70 hexahydro-5-methyl-1H-azepin-2-imine, monohydrochloride

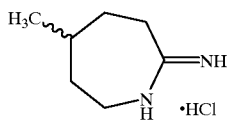

The product of EXAMPLE 69 (750 mg, 5.3 mmol) in 3 mL of EtOH was reacted with ammonium chloride (285 mg, 5.3 mmol) by the method of EXAMPLE 27 to yield 700 mg (77%) of the title material.

HRMS m/z $M^+$, $C_7H_{15}N_2$ requires 127.124; $^1$H NMR (400 MHz, $CD_3OD$) δ3.4–3.45 (m, 2H), 2.7–2.8 (m, 1H), 1.6–1.69 (m, 1H), 1.9–2.0 (m, 1H), 1.75–1.89 (m, 2H), 1.14–1.28 (m, 2H), 1 (d, 3H, J=4.2 Hz).

Elemental analysis: $C_7H_{14}N_2$.0.8 HCl.0.8 $H_2O$ (MW= 171.59)

|  | C | H | N | Cl |
|---|---|---|---|---|
| Calculated: | 48.99 | 9.66 | 16.32 | 17.56 |
| Found: | 49.20 | 8.94 | 16.01 | 17.24 |

EXAMPLE 71

4-cyclohexylcyclohexanone, oxime

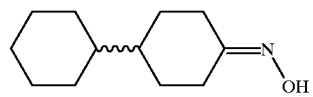

A sample of 4-cyclohexylcyclohexanone (Bader, 5.0 g, 27.7 mmol) was converted to the title compound by the method of EXAMPLE 24 using 2.9 g (41.6 mmol) of hydroxylamine hydrochloride and 3.9 g (47.1 mmol) of NaOAc in a mixture of 25 mL of EtOH and 25 mL of water. The procedure produced 5.3 g (97%) of the title material as a pale yellow oil.

EXAMPLE 72

5-cyclohexyl-hexahydro-1H-azepin-2-one

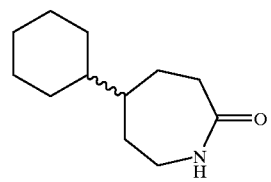

A sample of the product of EXAMPLE 71 (4.5 g, 23.0 mmol) was converted to the title compound by the method of EXAMPLE 25 using 10 mL of 80% $H_2SO_4$. The procedure produced 2.1 g (47%) of the title material after chromatography.

EXAMPLE 73

4-cyclohexyl-3,4,5,6-tetrahydro-7-methoxy-2H-azepine

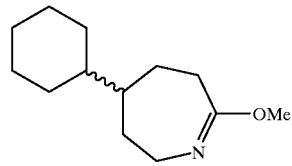

The product of EXAMPLE 72 is reacted with trimethyloxonium tetrafluoroborate by the method of EXAMPLE 26 to produce the title material.

EXAMPLE 74

5-cyclohexyl-hexahydro-1H-azepin-2-imine, monohydrochloride

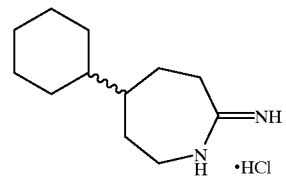

The product of EXAMPLE 73 in MeOH is reacted with ammonium chloride by the method of EXAMPLE 27 to generate the title material.

EXAMPLE 75

4-(1-methylethyl)cyclohexanone, oxime

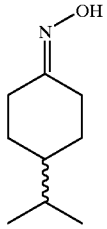

A sample of 4-isopropylcyclohexanone (P & B, 3.8 g, 26.9 mmol) was converted to the title compound by the method of EXAMPLE 24 using 2.8 g (40.4 mmol) of hydroxylamine hydrochloride and 3.7 g (45.7 mmol) of NaOAc in a mixture of 25 mL of EtOH and 25 mL of water. The procedure produced 4.1 g (100%) of the title material as a clear oil.

EXAMPLE 76 hexahydro-5-(1-methylethyl)-1H-azepin-2-one

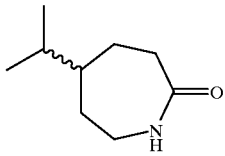

A sample of the product of EXAMPLE 75 (3.7 g, 24.2 mmol) was converted to the title compound by the method of EXAMPLE 25 using 10 mL of 80% H$_2$SO$_4$. The procedure produced 2.4 g (63%) of the title material after chromatography.

EXAMPLE 77

3,4,5,6-tetrahydro-7-methoxy-4-(1-methylethyl)-2H-azepine

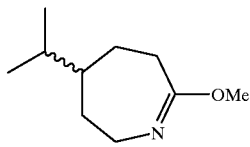

The product of EXAMPLE 76 is reacted with trimethyloxonium tetrafluoroborate by the method of EXAMPLE 26 to produce the title material.

EXAMPLE 78 hexahydro-5-(1-methylethyl)-1H-azepin-2-imine, monohydrochloride

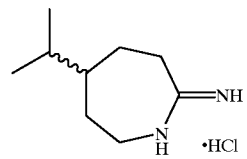

The product of EXAMPLE 77 in MeOH is reacted with ammonium chloride by the method of EXAMPLE 27 to generate the title material.

EXAMPLE 79

4-pentylcyclohexanone, oxime

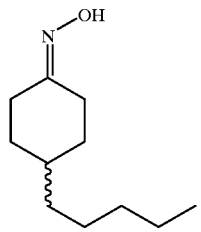

A sample of 4-n-pentylcyclohexanone (TCI, 5.2 g, 31.0 mmol) was converted to the title compound by the method of EXAMPLE 24 using 3.2 g (46.7 mmol) of hydroxylamine hydrochloride and 4.3 g (52.8 mmol) of NaOAc in a mixture of 25 mL of EtOH and 25 mL of water. The procedure produced 6.1 g (96%) of the title material as a pale yellow liquid.

EXAMPLE 80 hexahydro-5-pentyl-1H-azepin-2-one

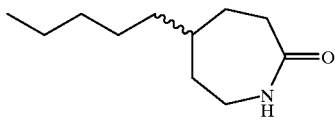

A sample of the product of EXAMPLE 79 (5.7 g, 31.4 mmol) was converted to the title compound by the method of EXAMPLE 25 using 20 mL of 80% H$_2$SO$_4$. The procedure produced 3.7 g (64%) of the title material after chromatography.

EXAMPLE 81

3,4,5,6-tetrahydro-7-methoxy-4-pentyl-2H-azepine

The product of EXAMPLE 80 (1.5 g, 8.2 mmol) was reacted with trimethyloxonium tetrafluoroborate (1.4 g, 9.8 mmol) by the method of EXAMPLE 26 to yield, after chromatography, 1.1 g (65%) of the title material.

EXAMPLE 82 hexahydrohydro-5-pentyl-1H-azepin-2-imine, monohydrochloride

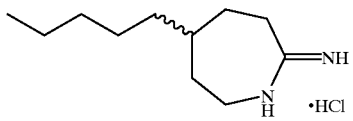

The product of EXAMPLE 81 (755 mg, 3.8 mmol) in 7.5 mL of EtOH was reacted with ammonium chloride (204 mg, 3.8 mmol) by the method of EXAMPLE 27 to yield 643 mg (73%) of the title material.

HRMS (EI) calcd for $C_{11}H_{22}N_2$ m/e 182.178, found m/e 182.179. $^1$H NMR (400 MHz, $D_2O$) δ3.35–3.53 (m, 2H), 2.6–2.75 (m, 2H), 1.96–2.04 (m, 1H), 1.85–1.95 (m, 1H), 1.6–1.75 (m, 1H), 1.2–1.4 (m, 10H), 0.88 (t, 3H, J=4 Hz).

Elemental analysis: $C_{11}H_{22}N_2.1.0$ HCl.0.2 $H_2O.0.15$ $NH_4Cl$ (MW=230.40)

|  | C | H | N | Cl |
|---|---|---|---|---|
| Calculated: | 57.31 | 10.56 | 13.06 | 17.68 |
| Found: | 57.55 | 10.53 | 13.23 | 17.69 |

EXAMPLE 83

4-(1,1-dimethylethyl)-3,4,5,6-tetrahydro-7-methoxy-2H-azepine

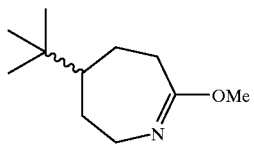

A sample of 4-tertbutylcaprolactam (Bader, 2.5 g, 14.8 mmol) was reacted with dimethylsulfate (1.4 mL, 14.8 mmol) by the method of EXAMPLE 69 to yield, after chromatography, 2.7 g of the title material.

EXAMPLE 84

5-(1,1-dimethylethyl)-hexahydro-1H-azepin-2-imine, monohydrochloride

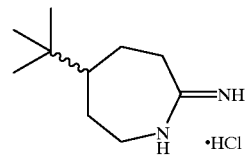

The product of EXAMPLE 83 (2.5 g, 13.6 mmol) in 50 mL of EtOH was reacted with ammonium chloride (730 mg, 13.6 mmol) by the method of EXAMPLE 27 to yield 2.2 g (78%) of the title material.

$^1$H NMR (400 MHz, $CD_3OD$) δ3.5 (ddd, 1H, J=1.87, 6.08, 15.0 Hz), 3.33–3.41 (m, 1H), 2.66–2.71 (m, 2H), 2.13–2.21 (m, 1H), 2.0–2.08 (m, 1H), 1.39 (tt, 1H, J=2.9, 11.9 Hz), 1.15–1.26 (m, 2H), 0.9 (s, 9H).

Elemental analysis: $C_{10}H_{20}N_2.0.8$ HCl.1.125 $H_2O.0.6$ $NH_4Cl$ (MW=249.80)

|  | C | H | N | Cl |
|---|---|---|---|---|
| Calculated: | 47.65 | 10.28 | 14.45 | 19.69 |
| Found: | 47.75 | 9.76 | 14.22 | 19.97 |

EXAMPLE 85

3R-methylcyclohexanone, oxime

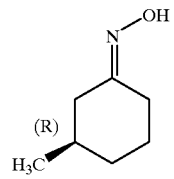

A sample of R(+)-3-methylcyclohexanone (Aldrich, 5.0 g, 44.6 mmol) was converted to the title compound by the method of EXAMPLE 24 using 4.6 g (66.9 mmol) of hydroxylamine hydrochloride and 6.2 g (75.8 mmol) of NaOAc in a mixture of 25 mL of EtOH and 25 mL of water. The procedure produced 5.7 g (100%) of the title material as a clear oil.

EXAMPLE 86 hexahydro-4R-methyl-1H-azepin-2-one, mixture with hexahydro-6R-methyl-1H-azepin-2-one

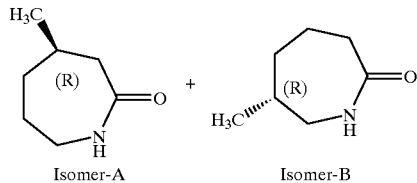

A sample of the product of EXAMPLE 85 (5.0 g, 39.3 mmol) was converted to the title compound mixture of two regioisomers by the method of EXAMPLE 25 using 10 mL of 80% $H_2SO_4$. The procedure produced 4.3 g of the title materials as a pale yellow oil. This mixture was separated into its components by chromatography to yield 215 mg of isomer-A and 318 mg of isomer-B.

EXAMPLE 87

3,4,5,6-tetrahydro-7-methoxy-5R-methyl-2H-azepine

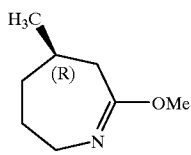

The Isomer-A product of EXAMPLE 86 is reacted with trimethyloxonium tetrafluoroborate by the method of EXAMPLE 26 to generate the title material.

EXAMPLE 88

3,4,5,6-tetrahydro-7-methoxy-3R-methyl-2H-azepine

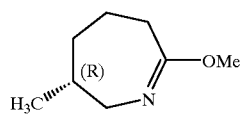

The Isomer-B product of EXAMPLE 86 (225 mg, 1.8 mmol) was reacted with trimethyloxonium tetrafluoroborate (340 mg, 2.3 mmol) by the method of EXAMPLE 26 to yield, after chromatography, 900 mg of the crude title material.

EXAMPLE 89 hexahydro-4R-methyl-1H-azepin-2-imine, monohydrochloride

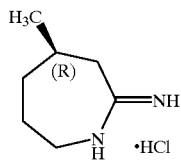

The product of EXAMPLE 87 in MeOH is reacted with ammonium chloride by the method of EXAMPLE 27 to generate the title material.

EXAMPLE 90 hexahydro-6R-methyl-1H-azepin-2-imine, monohydrochloride

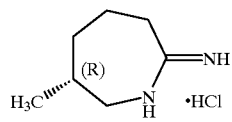

The product of EXAMPLE 88 (250 mg, 1.8 mmol) in 10 mL of MeOH was reacted with ammonium chloride (80 mg, 1.5 mmol) by the method of EXAMPLE 27 to yield 155 mg (44%) of the title material.

$^1$H NMR (300 MHz, D$_2$O) δ3.22–3.36 (m, 2H), 2.58–2.72 (m, 2H), 1.89–1.94 (m, 2H), 1.75–1.79 (m, 1H), 1.59–1.66 (m, 1H), 1.44–1.50 (m, 1H), 0.92 (d, 3H, J=4.2 Hz).

Elemental analysis: C$_7$H$_{14}$N$_2$.1.0 HCl.0.25 H$_2$O.0.55 NH$_4$Cl (MW=196.60)

|  | C | H | N | Cl |
|---|---|---|---|---|
| Calculated | 42.77 | 9.08 | 18.17 | 27.95 |
| Found: | 43.07 | 9.04 | 18.42 | 28.37 |

EXAMPLE 91

2-cyclohexylcyclohexanone, oxime

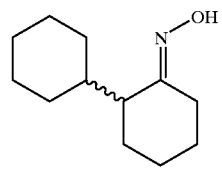

A sample of 2-cyclohexylcyclohexanone (Fluka, 10.0 g, 55.5 mmol) was converted to the title compound by the method of EXAMPLE 24 using 5.8 g (69.5 mmol) of hydroxylamine hydrochloride and 7.7 g (82.0 mmol) of NaOAc in a mixture of 50 mL of EtOH and 50 mL of water. The procedure produced 11.7 g of the crude title compound as pale yellow oil.

EXAMPLE 92

3-cyclohexyl-hexahydro-1H-azepin-2-one, mixture with 7-cyclohexyl-hexahydro-1H-azepin-2-one

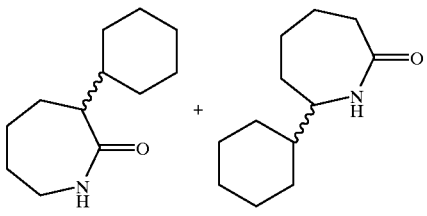

Isomer-A          Isomer-B

The product of EXAMPLE 91 (10.0 g, 51.2 mmol) was converted to the title compound mixture of two regioisomers by the method of EXAMPLE 29 using 9.13 g (51.7 mmol) of benzene sulfonylchloride. The crude product mixture was triturated with Et$_2$O to give 4.9 g of title product Isomer B. The filtrate was concentrated to provide a mixture of isomers but predominately title product Isomer A. This mixture is separated into its Isomer-A and Isomer-B components by chromatography.

EXAMPLE 93

6-cyclohexyl-3,4,5,6-tetrahydro-7-methoxy-2H-azepine

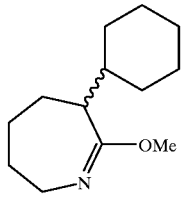

The Isomer-A product of EXAMPLE 92 is reacted with trimethyloxonium tetrafluoroborate by the method of EXAMPLE 26 to produce the title material.

EXAMPLE 94

2-cyclohexyl-3,4,5,6-tetrahydro-7-methoxy-2H-azepine

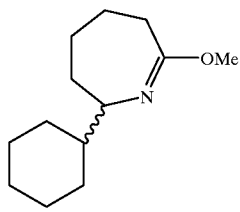

The Isomer-B product of EXAMPLE 92 (1.50 g, 3.6 mmol) was reacted with trimethyloxonium tetrafluoroborate (1.48 g, 10.0 mmol) by the method of EXAMPLE 26 to yield 0.76 g (48%) of the title material as a clear liquid.

EXAMPLE 95

3-cyclohexyl-hexahydro-1H-azepin-2-imine, monohydrochloride

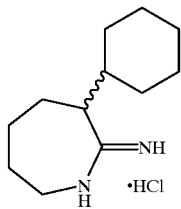

The product of EXAMPLE 93 in MeOH is reacted with ammonium chloride by the method of EXAMPLE 27 to generate the title material.

EXAMPLE 96

7-cyclohexyl-hexahydro-1H-azepin-2-imine, monohydrochloride

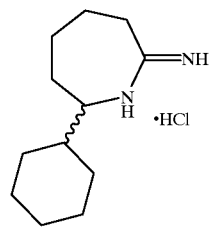

The product of EXAMPLE 94 (730 mg, 3.45 mmol) in 30 mL of MeOH was reacted with ammonium chloride (177 mg, 3.31 mmol) by the method of EXAMPLE 27 to yield 579 mg (75%) of the title material.

$^1$H NMR (400 MHz, D$_2$O) δ3.48–3.41 (dd, J=9.3 Hz, 1H), 2.8–2.7 (m, 1H), 2.61–2.54 (m, 1H), 2.0–1.0 (m, 17H).

Elemental analysis: $C_{12}H_{22}N_2 \cdot 1.0$ HCl$\cdot 0.6$ H$_2$O (MW= 241.59)

|  | C | H | N | Cl |
| --- | --- | --- | --- | --- |
| Calculated | 59.66 | 10.10 | 11.60 | 14.67 |
| Found: | 59.41 | 9.92 | 11.31 | 14.83 |

EXAMPLE 97

2-(1,1-dimethylethyl)cyclohexanone, oxime

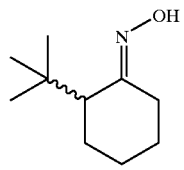

A sample of 2-tert-butylcyclohexanone (Aldrich, 5.0 g, 32.4 mmol) was converted to the title compound by the method of EXAMPLE 24 using 3.4 g (48.6 mmol) of hydroxylamine hydrochloride and 4.5 g (55.0 mmol) of NaOAc in a mixture of 50 mL of EtOH and 50 mL of water. The procedure produced 5.0 g (92%) of the crude title compound.

EXAMPLE 98

3-(1,1-dimethylethyl)-hexahydro-1H-azepin-2-one, mixture with 7-(1,1-dimethylethyl)-hexahydro-1H-azepin-2-one

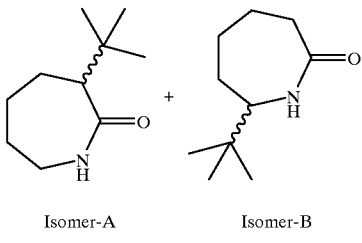

Isomer-A          Isomer-B

A sample of the product of EXAMPLE 97 (4.7 g, 27.8 mmol) was converted to the title compound mixture of two regioisomers by the method of EXAMPLE 25 using 9 mL of 80% $H_2SO_4$. The procedure produced 3.9 g of the title materials as a yellow solid. This mixture was separated into its components by chromatography to yield 832 mg of Isomer-A and 2.52 g of Isomer-B.

EXAMPLE 99

6-(1,1-dimethylethyl)-3,4,5,6-tetrahydro-7-methoxy-2H-azepine

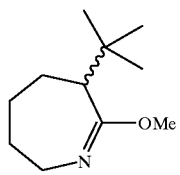

The Isomer-A product of EXAMPLE 98 (664 mg, 3.9 mmol) was reacted with trimethyloxonium tetrafluoroborate (696 mg, 4.7 mmol) by the method of EXAMPLE 26 to yield, after chromatography, 654 mg (91%) of the title material.

EXAMPLE 100

2-(1,1-dimethylethyl)-3,4,5,6-tetrahydro-7-methoxy-2H-azepine

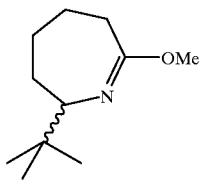

The Isomer-B product of EXAMPLE 98 (352 mg, 2.1 mmol) was reacted with trimethyloxonium tetrafluoroborate (370 mg, 2.5 mmol) by the method of EXAMPLE 26 to yield, after chromatography, the title material.

EXAMPLE 101

3-(1,1-dimethylethyl)-hexahydro-1H-azepin-2-imine, monohydrochloride

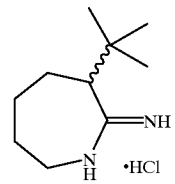

The product of EXAMPLE 99 (551 mg, 2.7 mmol) in 10 mL of MeOH was reacted with ammonium chloride (145 mg, 2.7 mmol) by the method of EXAMPLE 27 to yield 350 mg of the crude title material.

EXAMPLE 102

7-(1,1-dimethylethyl)-hexahydro-1H-azepin-2-imine, monohydrochloride

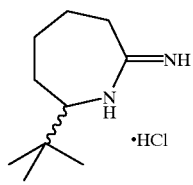

The product of EXAMPLE 100 (174 mg, 1.0 mmol) in 10 mL of EtOH was reacted with ammonium chloride (51 mg, 1.0 mmol) by the method of EXAMPLE 27 to yield the crude title material.

EXAMPLE 103

2-(2-propenyl)cyclohexanone, oxime

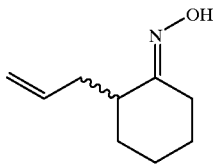

A sample of 2-allylcyclohexanone (Frinton, 2.0 g, 14.5 mmol) was converted to the title compound by the method of EXAMPLE 24 using 1.5 g (21.7 mmol) of hydroxylamine hydrochloride and 2.0 g (24.6 mmol) of NaOAc in a mixture of 25 mL of EtOH and 25 mL of water. The procedure produced 2.6 g of the crude title compound.

EXAMPLE 104 hexahydro-3-(2-propenyl)-1H-azepin-2-one, mixture with hexahydro-7-(2-propenyl)-1H-azepin-2-one

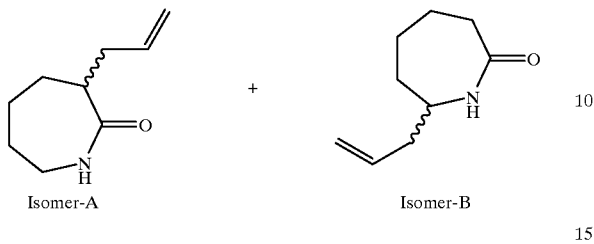

Isomer-A          Isomer-B

The title product of EXAMPLE 103 (2.0 g, 13.0 mmol) in 15 mL of acetone containing 1N NaOH (14.3 mL, 52.4 mmol) was reacted with benzene sulfonylchloride (2.3 g, 13.1 mmol) by the method described in EXAMPLE 29. The crude reaction mixture was separated into its Isomer-A and Isomer-B components by silica gel chromatography.

EXAMPLE 105

3,4,5,6-tetrahydro-7-methoxy-6-(2-propenyl)-2H-azepine

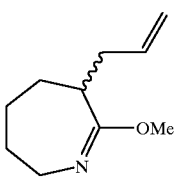

The Isomer-A product of EXAMPLE 104 (130 mg, 0.85 mmol) was reacted with trimethyloxonium tetrafluoroborate (163 mg, 1.10 mmol) by the method of EXAMPLE 26 to yield, after chromatography, 91 mg (64%) of the title material.

EXAMPLE 106

3,4,5,6-tetrahydro-7-methoxy-2-(2-propenyl)-2H-azepine

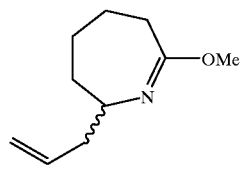

The Isomer-B product of EXAMPLE 104 (250 mg, 1.63 mmol) was reacted with trimethyloxonium tetrafluoroborate (312 mg, 2.11 mmol) by the method of EXAMPLE 26 to yield, after chromatography, 194 mg (71%) of the title material.

EXAMPLE 107 hexahydro-3-(2-propenyl)-1H-azepin-2-imine, monohydrochloride

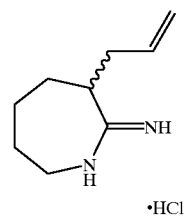

The product of EXAMPLE 105 (90 mg, 0.54 mmol) in 10 mL of MeOH was reacted with ammonium chloride (24.5 mg, 0.46 mmol) by the method of EXAMPLE 27 to yield 68 mg (67%) of the title material.

$^1$H NMR (300 MHz, CD$_3$OD) δ5.9–5.7 (m, 1H), 5.3–5.1 (m, 2H), 3.6–3.4 (m, 2H), 3.0–2.9 (m, 1H), 2.7–2.5 (m, 1H), 2.45–2.3 (m, 1H), 2.0–1.6 (M, 6H).

EXAMPLE 108 hexahydro-7-(2-propenyl)-1H-azepin-2-imine, monohydrochloride

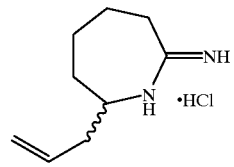

The product of EXAMPLE 106 (70 mg, 0.42 mmol) in 3 mL of MeOH was reacted with ammonium chloride (21.4 mg, 0.4 mmol) by the method of EXAMPLE 27 to yield 60 mg (76%) of the title material.

$^1$H NMR (400 MHz, D$_2$O) δ5.9–5.8 (m, 1H), 5.26–5.19 (m, 2H), 3.79–3.70 (m, 1H), 2.8–2.7 (m, 1H), 2.62–2.56 (m, 1H), 2.42–2.39 (m, 2H), 2.04–1.94 (m, 2H,), 1.91–1.84 (m, 1H), 1.7–1.6 (m, 1H), 1.56–1.35 (m, 2H).

Elemental analysis: C$_9$H$_{16}$N$_2$.1.0 HCl.0.75 H$_2$O.0.05 NH$_4$Cl (MW=204.88)

|  | C | H | N | Cl |
|---|---|---|---|---|
| Calculated: | 52.76 | 9.20 | 14.01 | 18.17 |
| Found: | 53.13 | 9.06 | 14.05 | 18.32 |

EXAMPLE 109

2-propylcyclohexanone, oxime

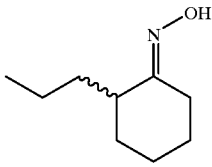

A sample of 2-n-propylcyclohexanone (Farchan, 19.7 g, 140.5 mmol) was converted to the title compound by the method of EXAMPLE 24 using 14.6 g (211.0 mmol) of hydroxylamine hydrochloride and 20.8 g (252.9 mmol) of NaOAc in a mixture of 150 mL of EtOH and 100 mL of water. The procedure produced 23.4 g of the crude title compound.

EXAMPLE 110 hexahydro-3-propyl-1H-azepin-2-one, mixture with hexahydro-7-propyl-1H-azepin-2-one

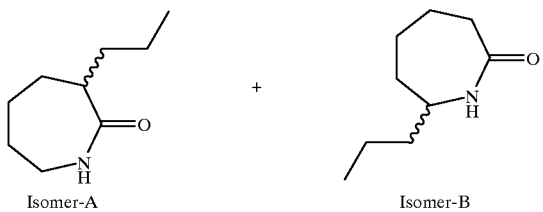

Isomer-A                Isomer-B

The product of EXAMPLE 109 (11.5 g, 74.1 mmol) was converted to the title compound mixture of two regioisomers by the method of EXAMPLE 29 using 13.2 g ( 74.5 mmol) of benzene sulfonylchloride. The crude pale yellow solid product mixture (6.1 g) was separated into its Isomer-A and Isomer-B components by chromatography.

EXAMPLE 111

3,4,5,6-tetrahydro-7-methoxy-6-propyl-2H-azepine

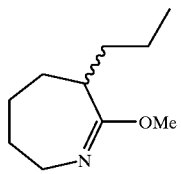

The Isomer-A product of EXAMPLE 110 (0.50 g, 3.2 mmol) was reacted with trimethyloxonium tetrafluoroborate (0.62 g, 4.2 mmol) by the method of EXAMPLE 26 to yield, after chromatography, 0.45 g (83%) of the title material.

Elemental analysis: $C_{10}H_{19}NO.0.1\ H_2O$ (MW=169.27)

|  | C | H | N |
|---|---|---|---|
| Calculated: | 70.21 | 11.31 | 8.19 |
| Found: | 70.35 | 11.32 | 7.97 |

EXAMPLE 112

3,4,5,6-tetrahydro-7-methoxy-2-propyl-2H-azepine

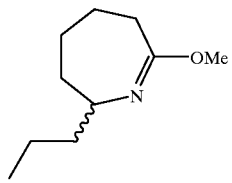

The Isomer-B product of EXAMPLE 110 (0.65 g, 4.2 mmol) was reacted with trimethyloxonium tetrafluoroborate (0.81 g, 5.4 mmol) by the method of EXAMPLE 26 to yield, after chromatography, 0.60 g (84%) of the title material.

Elemental analysis: $C_{10}H_{19}NO.0.125\ H_2O$ (MW=171.52)

|  | C | H | N |
|---|---|---|---|
| Calculated: | 70.03 | 11.31 | 8.47 |
| Found: | 69.94 | 11.41 | 7.92 |

EXAMPLE 113 hexahydro-3-propyl-1H-azepin-2-imine, monohydrochloride

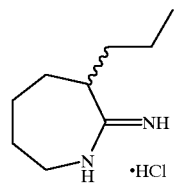

The product of EXAMPLE 111 (415 mg, 2.45 mmol) in 20 mL of MeOH was reacted with ammonium chloride (111 mg, 2.1 mmol) by the method of EXAMPLE 27 to yield 360 mg (76%) of the title material.

$^1$H NMR (400 MHz, CD$_3$OD) δ3.48 (m, 2H), 2.90–2.81 (m, 1H), 1.96–1.85 (m, 1H), 1.85–1.55 (m, 7H), 1.55–1.32 (m, 2H), 1.00 (t, 3H, J=7.3 Hz).

Elemental analysis: $C_9H_{18}N_2.1.0\ HCl.0.15\ H_2O.0.02\ NH_4Cl$ (MW=194.43)

|  | C | H | N | Cl |
|---|---|---|---|---|
| Calculated: | 55.60 | 10.02 | 14.55 | 18.60 |
| Found: | 55.57 | 9.92 | 14.35 | 18.62 |

EXAMPLE 114 hexahydro-7-propyl-1H-azepin-2-imine, monohydrochloride

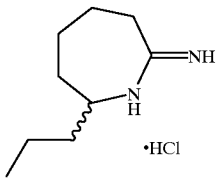

The product of EXAMPLE 112 (560 mg, 3.3 mmol) in 20 mL of MeOH was reacted with ammonium chloride (150 mg, 2.8 mmol) by the method of EXAMPLE 27 to yield 514 mg (78%) of the title material.

$^1$H NMR (400 MHz, CD$_3$OD) δ3.68–3.58 (m, 1H), 2.79 (ddd, 1H, J=14.3, 12.2, 1.9 Hz), 2.61 (dd, 1H, J=14.6, 6.6 Hz), 2.06–1.95 (m, 2H), 1.90–1.81 (m, 1H), 1.75–1.32 (m, 7H), 0.98 (t, 3H, J=7.2 Hz).

Elemental analysis: C$_9$H$_{18}$N$_2$.1.0 HCl.0.4 H$_2$O.0.05 NH$_4$Cl (MW=200.60)

|  | C | H | N | Cl |
|---|---|---|---|---|
| Calculated: | 53.89 | 10.05 | 14.31 | 18.56 |
| Found: | 53.95 | 10.15 | 13.96 | 18.64 |

EXAMPLE 115

2-(1-methylpropyl)cyclohexanone, oxime

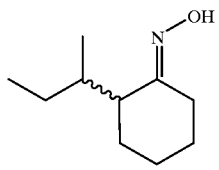

A sample of 2-sec-butylcyclohexanone (Lancaster, 9.9 g, 64.2 mmol) was converted to the title compound by the method of EXAMPLE 24 using 6.7 g (96.3 mmol) of hydroxylamine hydrochloride and 9.5 g (115.6 mmol) of NaOAc in a mixture of 75 mL of EtOH and 50 mL of water. The procedure produced 11.3 g of the crude title compound.

EXAMPLE 116 hexahydro-3-(1-methylpropyl)-1H-azepin-2-one, mixture with hexahydro-7-(1-methylpropyl)-1H-azepin-2-one

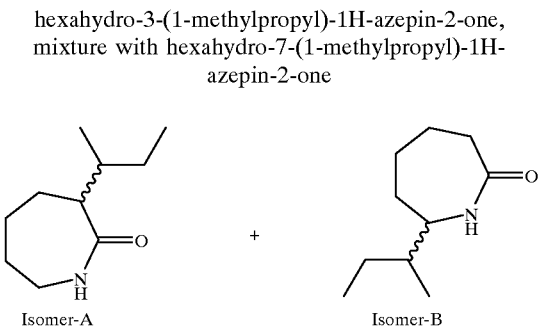

Isomer-A          Isomer-B

The product of EXAMPLE 115 is converted to the title compound mixture of two regioisomers by the method of EXAMPLE 25 using 80% H$_2$SO$_4$. This product mixture is separated into its Isomer-A and Isomer-B components by chromatography.

EXAMPLE 117

3,4,5,6-tetrahydro-7-methoxy-6-(1-methylpropyl)-2H-azepine

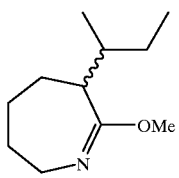

The Isomer-A product of EXAMPLE 116 is reacted with trimethyloxonium tetrafluoroborate by the method of EXAMPLE 26 to produce the title material.

EXAMPLE 118

3,4,5,6-tetrahydro-7-methoxy-2-(1-methylpropyl)-2H-azepine

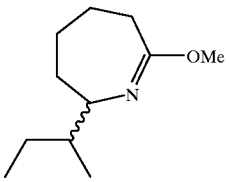

The Isomer-B product of EXAMPLE 116 is reacted with trimethyloxonium tetrafluoroborate by the method of EXAMPLE 26 to produce the title material.

EXAMPLE 119 hexahydro-3-(1-methylpropyl)-1H-azepin-2-imine, monohydrochloride

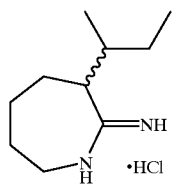

The product of EXAMPLE 117 in MeOH is reacted with ammonium chloride by the method of EXAMPLE 27 to generate the title material.

EXAMPLE 120 hexahydro-7-(1-methylpropyl)-1H-azepin-2-imine, monohydrochloride

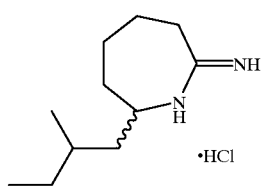

The product of EXAMPLE 118 in MeOH is reacted with ammonium chloride by the method of EXAMPLE 27 to generate the title material.

EXAMPLE 121

3,4-dimethylcyclohexanone, oxime

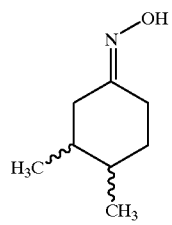

A sample of 3,4-dimethylcyclohexanone (TCI, 9.0 g, 71.0 mmol) was converted to the title compound by the method of EXAMPLE 24 using 7.4 g (107.0 mmol) of hydroxylamine hydrochloride and 9.9 g (121.0 mmol) of NaOAc in a mixture of 50 mL of EtOH and 50 mL of water. The procedure yielded 2.6 g of the crude title compound.

EXAMPLE 122 hexahydro-4,5-dimethyl-1H-azepin-2-one, mixture with hexahydro-5,6-dimethyl-1H-azepin-2-one

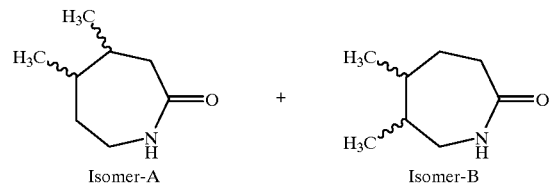

Isomer-A          Isomer-B

A sample of the product of EXAMPLE 121 (8.0 g, 56.6 mmol) was converted to the title compound mixture of two regioisomers by the method of EXAMPLE 25 using 20 mL of 80% $H_2SO_4$. The procedure gave 7.1 g of the title materials as an amber liquid. This mixture was separated into its component regioisomers by chromatography to yield 233 mg of Isomer-A title compound and 87 mg of Isomer-B title compound.

EXAMPLE 123

3,4,5,6-tetrahydro-7-methoxy-4,5-dimethyl-2H-azepine

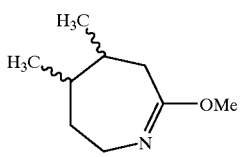

The Isomer-A product of EXAMPLE 122 (205 mg, 1.5 mmol) was reacted with trimethyloxonium tetrafluoroborate (279 mg, 1.9 mmol) by the method of EXAMPLE 26 to yield, after chromatography, 100 mg (53%) of the title material.

EXAMPLE 124

3,4,5,6-tetrahydro-7-methoxy-3,4-dimethyl-2H-azepine

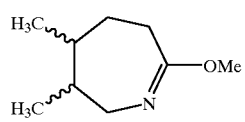

The Isomer-B product of EXAMPLE 122 is reacted with trimethyloxonium tetrafluoroborate by the method of EXAMPLE 26 to produce the title material.

EXAMPLE 125 hexahydro-4,5-dimethyl-1H-azepin-2-imine, monohydrochloride

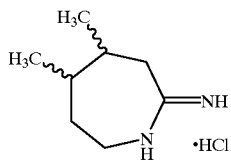

The product of EXAMPLE 123 (100 mg, 0.64 mmol) in 5 mL of MeOH was reacted with ammonium chloride (29.3 mg, 547 mmol) by the method of EXAMPLE 27 to yield 68 mg (66%) of the white solid title material.

1H NMR (300 MHz, $D_2O$) δ3.25–3.45 (m, 2H), 2.85 (d, 1H, J=12 Hz), 2.6 (dd, 1H, J=9, 15 Hz), 2.05–2.08 (m, 1H), 1.9–2.0 (m, 1H), 1.4–1.61 (m, 2H), 0.94 (d, 3H, J=9 Hz), 0.88 (d, 3H, J=6 Hz).

Elemental analysis: $C_8H_{16}N_2 \cdot 1.0$ HCl $\cdot 0.01$ $H_2O \cdot 0.2$ $NH_4Cl$ (MW=187.57)

|  | C | H | N | Cl |
|---|---|---|---|---|
| Calculated: | 51.23 | 9.58 | 16.43 | 22.68 |
| Found: | 50.85 | 9.51 | 16.22 | 22.59 |

EXAMPLE 126 hexahydro-5,6-dimethyl-1H-azepin-2-imine, monohydrochloride

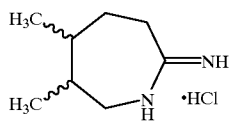

The product of EXAMPLE 124 in MeOH is reacted with ammonium chloride by the method of EXAMPLE 27 to generate the title material.

EXAMPLE 127

2,5-dimethylcyclohexanone, oxime

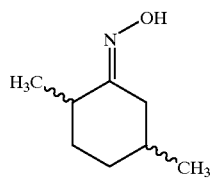

A sample of 2,5-dimethylcyclohexanone (TCI, 9.0 g, 71.0 mmol) was converted to the title compound by the method of EXAMPLE 24 using 7.4 g (107.0 mmol) of hydroxylamine hydrochloride and 9.9 g (121.0 mmol) of NaOAc in a mixture of 50 mL of EtOH and 50 mL of water. The procedure generated 7.1 g (71%) of the crude title compound.

EXAMPLE 128 hexahydro-3,6-dimethyl-1H-azepin-2-one, mixture with hexahydro-4,7-dimethyl-1H-azepin-2-one

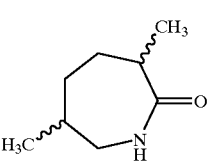 + 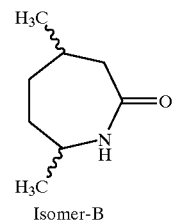

Isomer-A          Isomer-B

A sample of the product of EXAMPLE 127 (6.8 g, 48.5 mmol) was converted to the title compound mixture of two regioisomers by the method of EXAMPLE 25 using 20 mL of 80% $H_2SO_4$. The procedure produced the crude title materials. This mixture was separated into its component regioisomers by chromatography to yield no clean amount of Isomer-A title compound and 1.3 g of pure Isomer-B title compound. Rechromatography of the mixtures yields pure Isomer-A.

EXAMPLE 129

3,4,5,6-tetrahydro-7-methoxy-3,6-dimethyl-2H-azepine

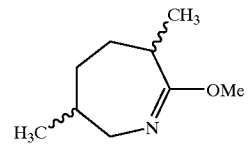

The Isomer-A product of EXAMPLE 128 is reacted with trimethyloxonium tetrafluoroborate by the method of EXAMPLE 26 to produce the title material.

EXAMPLE 130

3,4,5,6-tetrahydro-7-methoxy-2,5-dimethyl-2H-azepine

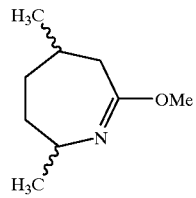

The Isomer-B product of EXAMPLE 128 (1.0 g, 7.1 mmol) was reacted with trimethyloxonium tetrafluoroborate (1.3 g, 8.5 mmol) by the method of EXAMPLE 26 to yield, after chromatography, 700 mg of the title material.

EXAMPLE 131 hexahydro-3,6-dimethyl-1H-azepin-2-imine, monohydrochloride

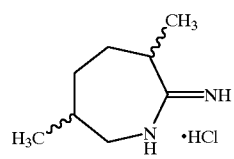

The product of EXAMPLE 129 in MeOH is reacted with ammonium chloride by the method of EXAMPLE 27 to generate the title material.

EXAMPLE 132 hexahydro-4,7-dimethyl-1H-azepin-2-imine, monohydrochloride

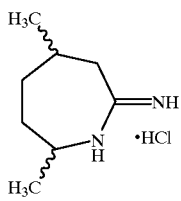

The product of EXAMPLE 130 (250 mg, 1.6 mmol) in 2.5 mL of EtOH was reacted with ammonium chloride (86.0 mg, 1.6 mmol) by the method of EXAMPLE 27 to yield 220 mg (75%) of the white solid title material.

$^1$H NMR (400 MHz, D$_2$O) δ3.7–3.8 (m, 1H,), 2.7 (dd, 1H, J=10,12 Hz), 2.4 (d, 1H, J=15 Hz), 1.9–2.0 (m, 1H), 1.7–1.85 (m, 2H), 1.4–1.55 (m, 2H), 1.3 (d, 6H, J=8 Hz), 1.06 (d, 3H, J=8 Hz).

Elemental analysis: C$_8$H$_{16}$N$_2$.1.06 HCl.0.25 H$_2$O (MW 183.38)

|  | C | H | N | Cl |
|---|---|---|---|---|
| Calculated: | 52.40 | 9.65 | 15.28 | 20.49 |
| Found: | 52.10 | 9.82 | 15.94 | 20.77 |

EXAMPLE 133

(2R-trans)-2-(1-methylethyl)-5-methylcyclohexanone, oxime

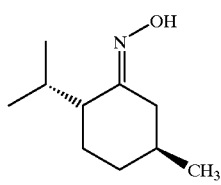

A sample of (−)menthone (Aldrich, 10.0 g, 64.8 mmol) was converted to the title compound by the method of EXAMPLE 24 using 6.8 g (97.3 mmol) of hydroxylamine hydrochloride and 9.0 g (110.2 mmol) of NaOAc in a mixture of 50 mL of EtOH and 50 mL of water. The procedure produced the crude title compound.

EXAMPLE 134

(4R-trans)-hexahydro-7-(1-methylethyl)-4-methyl-1H-azepin-2-one, mixture with (3S-trans)-hexahydro-3-(1-methylethyl)-6-methyl-1H-azepin-2-one

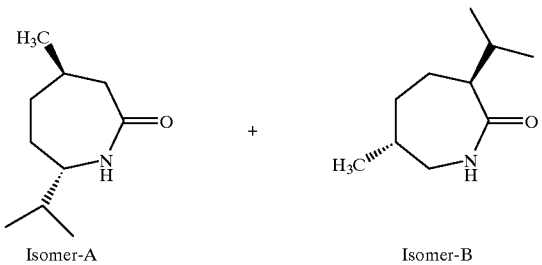

Isomer-A           Isomer-B

A sample of the product of EXAMPLE 133 (10.0 g, 59.0 mmol) was converted to the title compound mixture of two regioisomers by the method of EXAMPLE 25 using 20 mL of 80% H$_2$SO$_4$. The procedure produced the crude title materials.

This mixture was separated into its component regioisomers by chromatography to yield 3.1 g of Isomer-A title compound and 1.5 g of pure Isomer-B title compound.

EXAMPLE 135

(5R-trans)-3,4,5,6-tetrahydro-7-methoxy-2-(1-methylethyl)-5-methyl-2H-azepine

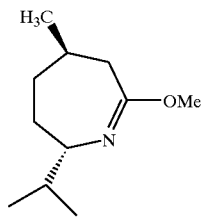

The Isomer-A product of EXAMPLE 134 (1.0 g, 5.9 mmol) was reacted with trimethyloxonium tetrafluoroborate (1.1 g, 7.1 mmol) by the method of EXAMPLE 26 to yield, after chromatography, 740 mg (68%) of the title material.

EXAMPLE 136

(6R-trans)-3,4,5,6-tetrahydro-7-methoxy-6-(1-methylethyl)-3-methyl-2H-azepine

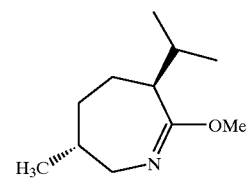

The Isomer-B product of EXAMPLE 134 (840 mg, 5.0 mmol) was reacted with trimethyloxonium tetrafluoroborate (880 mg, 6.0 mmol) by the method of EXAMPLE 26 to yield, after chromatography, 441 mg (49%) of the title material.

EXAMPLE 137

(7S-trans)-hexahydro-7-(1-methylethyl)-4-methyl-1H-azepin-2-imine, monohydrochloride

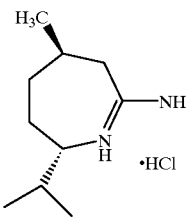

The product of EXAMPLE 135 (690 mg, 3.8 mmol) in 20 mL of MeOH was reacted with ammonium chloride (201 mg, 3.8 mmol) by the method of EXAMPLE 27 to yield 570 mg (73%) of the white solid title material.

HRMS (EI) calcd for $C_{10}H_{20}N_2$ m/e 168.163, found m/e 168.163. $^1$H NMR (400 MHz, $D_2O$) δ3.4–3.5 (m, 1H), 2.7 (dd, 1H, J=12, 15 Hz), 2.4 (bd, 1H, J=14 Hz), 1.8–2 (m, 3H), 1.7–1.8 (m, 1H), 1.31–1.45 (m, 2H), 1.05 (d, 3H, J=7.6 Hz), 0.95 (d, 6H, J=8 Hz).

Elemental analysis: $C_{10}H_{20}N_2 \cdot 1.0$ $HCl \cdot 0.33$ $H_2O \cdot 0.05 NH_4Cl$ (MW=213.36)

|  | C | H | N | Cl |
|---|---|---|---|---|
| Calculated: | 56.29 | 10.33 | 13.46 | 17.45 |
| Found: | 56.28 | 10.81 | 13.57 | 17.58 |

EXAMPLE 138

(3S-trans)-hexahydro-3-(1-methylethyl)-6-methyl-1H-azepin-2-imine, monohydrochloride

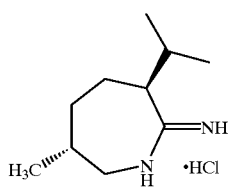

The product of EXAMPLE 136 (300 mg, 1.6 mmol) in 10 mL of MeOH was reacted with ammonium chloride (70 mg, 1.3 mmol) by the method of EXAMPLE 27 to yield 240 mg (86%) of the white solid title material.

$[\alpha]_D$=+33.6° (0.53, $CH_3OH$) $^1$H NMR (400 MHz, $D_2O$) δ3.6 (bd, 1H, J=14 Hz), 3.2 (dd, 1H, J=4,16 Hz) 2.35–2.45 (m, 1H), 2.2–2.3 (m, 1H), 1.95 (m, 3H), 1.65–1.75 (m, 1H), 1.42–1.52 (m, 1H), 1.0 (dd, 6H, J=7 Hz), 0.95 (d, 3H, J=6 Hz).

Elemental analysis: $C_{10}H_{20}N_2 \cdot 1.0$ $HCl \cdot 0.33$ $H_2O \cdot 0.05 NH_4Cl$ (MW=213.73)

|  | C | H | N | Cl |
|---|---|---|---|---|
| Calculated: | 56.20 | 10.45 | 13.11 | 15.76 |
| Found: | 56.58 | 10.24 | 12.70 | 15.88 |

EXAMPLE 139

3R-methylcyclopentanone, oxime

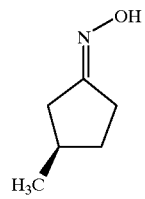

A sample of R(+)-3-methylcyclopentanone (Aldrich, 5.0 g, 50.9 mmol) was converted to the title compound by the method of EXAMPLE 24 using 5.3 g (76.4 mmol) of hydroxylamine hydrochloride and 7.1 g (86.5 mmol) of NaOAc in a mixture of 25 mL of EtOH and 25 mL of water. The procedure produced 4.9 g (86%) of the title material as white solid.

EXAMPLE 140

4R-methylpiperidin-2-one, mixture with 5R-methylpiperidin-2-one

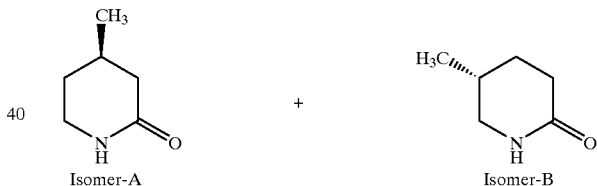

A sample of the product of EXAMPLE 139 (4.5 g, 39.8 mmol) was converted to the title compound mixture of two regioisomers by the method of EXAMPLE 25 using 10 mL of 80% $H_2SO_4$. The procedure produced 4.6 g of the title materials. This mixture was separated into its components by chromatography to yield Isomer-A and Isomer-B.

EXAMPLE 141

2,3,4,5-tetrahydro-6-methoxy-4R-methylpyridine

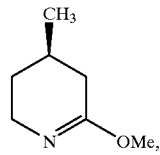

The Isomer-A product of EXAMPLE 140 is reacted with trimethyloxonium tetrafluoroborate by the method of EXAMPLE 26 to produce the title material.

EXAMPLE 142

2,3,4,5-tetrahydro-6-methoxy-3R-methylpyridine,

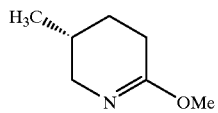

The Isomer-B product of EXAMPLE 140 is reacted with trimethyloxonium tetrafluoroborate by the method of EXAMPLE 26 to produce the title material.

EXAMPLE 143

4R-methylpiperidin-2-imine, monohydrochloride

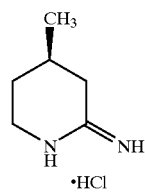

The product of EXAMPLE 141 in MeOH is reacted with ammonium chloride by the method of EXAMPLE 27 to generate the title material.

EXAMPLE 144

5R-methylpiperidin-2-imine, monohydrochloride

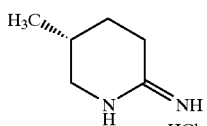

The product of EXAMPLE 142 in MeOH is reacted with ammonium chloride by the method of EXAMPLE 27 to generate the title material.

EXAMPLE 145

3-ethylcyclopentanone, oxime

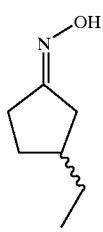

A sample of 3-ethylcyclopentanone is converted to the title compound by the method of EXAMPLE 24 using hydroxylamine hydrochloride and NaOAc in a mixture of EtOH and water.

EXAMPLE 146

4-ethylpiperidin-2-one, mixture with 5-ethylpiperidin-2-one

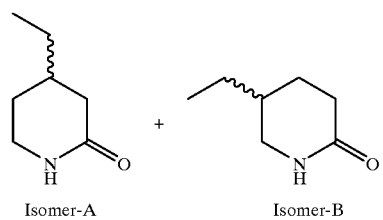

The product of EXAMPLE 145 is converted to the title compound mixture of two regioisomers by the method of EXAMPLE 25 using 80% $H_2SO_4$. This product mixture is separated into its Isomer-A and Isomer-B components by chromatography.

EXAMPLE 147

4-ethyl-2,3,4,5-tetrahydro-6-methoxypyridine

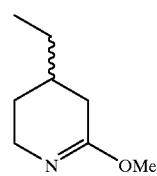

The Isomer-A product of EXAMPLE 146 is reacted with trimethyloxonium tetrafluoroborate by the method of EXAMPLE 26 to produce the title material.

EXAMPLE 148

3-ethyl-2,3,4,5-tetrahydro-6-methoxypyridine

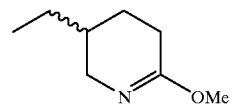

The Isomer-B product of EXAMPLE 146 is reacted with trimethyloxonium tetrafluoroborate by the method of EXAMPLE 26 to produce the title material.

EXAMPLE 149

4-ethylpiperidin-2-imine, monohydrochloride

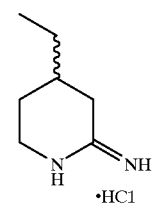

The product of EXAMPLE 147 in MeOH is reacted with ammonium chloride by the method of EXAMPLE 27 to generate the title material.

EXAMPLE 150

5-ethylpiperidin-2-imine, monohydrochloride

The product of EXAMPLE 148 in MeOH is reacted with ammonium chloride by the method of EXAMPLE 27 to generate the title material.

EXAMPLE 151

2-ethylcyclopentanone, oxime

A sample of 2-ethylcyclopentanone (P & B, 9.8 g, 87.5 mmol) was converted to the title compound by the method of EXAMPLE 24 using 8.5 g (122.5 mmol) of hydroxylamine hydrochloride and 12.9 g (157.5 mmol) of NaOAc in a mixture of 90 mL of EtOH and 90 mL of water. The procedure produced 12.0 g of the crude title compound as a yellow oil.

EXAMPLE 152

6-ethylpiperidin-2-one, mixture with 3-ethylpiperidin-2-one

Isomer-A    Isomer-B

The product of EXAMPLE 151 (2.1 g, 16.4 mmol) was converted to the title compound mixture of two regioisomers by the method of EXAMPLE 29 using 2.9 g (16.4 mmol) of benzene sulfonylchloride. The crude pale yellow solid product mixture (2.3 g) was separated into its Isomer-A and Isomer-B components by chromatography.

EXAMPLE 153

2-ethyl-2,3,4,5-tetrahydro-6-methoxypyridine

The Isomer-A product of EXAMPLE 152 (280 mg, 2.2 mmol) was reacted with trimethyloxonium tetrafluoroborate (425 mg, 2.9 mmol) by the method of EXAMPLE 26 to yield, after chromatography, 300 mg (96%) of the title material as a crystalline solid.

EXAMPLE 154

3-ethyl-3,4,5,6-tetrahydro-2-methoxypyridine

The Isomer-B product of EXAMPLE 152 is reacted with trimethyloxonium tetrafluoroborate by the method of EXAMPLE 26 to produce the title material.

EXAMPLE 155

6-ethylpiperidin-2-imine, monohydrochloride

The product of EXAMPLE 153 in MeOH is reacted with ammonium chloride by the method of EXAMPLE 27 to generate the title material.

EXAMPLE 156

3-ethylpiperidin-2-imine, monohydrochloride

The product of EXAMPLE 154 in MeOH is reacted with ammonium chloride by the method of EXAMPLE 27 to generate the title material.

EXAMPLE 157

2,2-dimethylcyclopentanone, oxime

A sample of 2,2-dimethylcyclopentanone (Aldrich, 9.0 g, 80.0 mmol) was converted to the title compound by the method of EXAMPLE 24 using 7.8 g (112.0 mmol) of hydroxylamine hydrochloride and 11.8 g (144.0 mmol) of NaOAc in a mixture of 90 mL of EtOH and 90 mL of water. The procedure produced 13.1 g of the crude title compound as a colorless oil.

EXAMPLE 158

6,6-dimethylpiperidin-2-one, mixture with 3,3-dimethylpiperidin-2-one

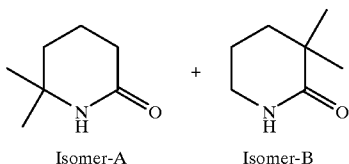

Isomer-A      Isomer-B

The product of EXAMPLE 157 (13.3 g, 104.7 mmol) was converted to the title compound mixture of two regioisomers by the method of EXAMPLE 29 using 18.5 g (104.7 mmol) of benzene sulfonylchloride. The crude pale yellow solid product mixture (8.3 g) was separated into its Isomer-A and Isomer-B components by chromatography.

EXAMPLE 159

2,3,4,5-tetrahydro-6-methoxy-2,2-dimethylpyridine

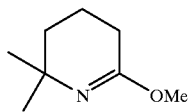

The Isomer-A product of EXAMPLE 158 (880 mg, 6.9 mmol) was reacted with trimethyloxonium tetrafluoroborate (1.3 g, 9.0 mmol) by the method of EXAMPLE 26 to yield, after chromatography, 502 mg (51%) of the title material as a pale yellow solid.

EXAMPLE 160

3,4,5,6-tetrahydro-2-methoxy-3,3-dimethylpyridine

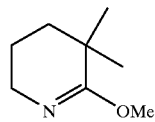

The Isomer-B product of EXAMPLE 158 is reacted with trimethyloxonium tetrafluoroborate by the method of EXAMPLE 26 to produce the title material.

EXAMPLE 161

6,6-dimethylpiperidin-2-imine, monohydrochloride

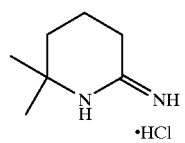

The product of EXAMPLE 159 in MeOH is reacted with ammonium chloride by the method of EXAMPLE 27 to generate the title material.

EXAMPLE 162

3,3-dimethylpiperidin-2-imine, monohydrochloride

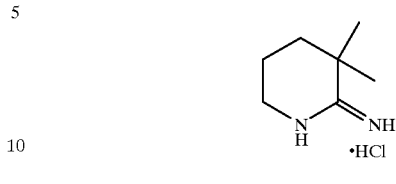

The product of EXAMPLE 160 in MeOH is reacted with ammonium chloride by the method of EXAMPLE 27 to generate the title material.

EXAMPLE 163

3,4-dihydro-2-methoxyquinoline

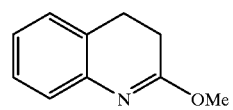

A sample of 3,4-dihydrocarbostyril (Apin Chemicals Ltd., 736 mg, 5.0 mmol) was reacted with trimethyloxonium tetrafluoroborate (924 mg, 6.2 mmol) by the method of EXAMPLE 26 to yield, after chromatography, 130 mg (16%) of the title material.

EXAMPLE 164

1,2,3,4-tetrahydroquinolin-2-imine, monohydrochloride

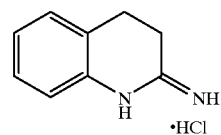

The product of EXAMPLE 163 (98 mg, 0.61 mmol) in 10 mL of MeOH and 10 mL of $CH_2Cl_2$ was reacted with ammonium chloride (27 mg, 0.52 mmol) by the method of EXAMPLE 27 to yield 57 mg (47%) of the title material.

HRMS m/z M$^+$ 147.086; $C_9H_{11}N_2$ requires 147.092. IR (KBr): $^1$H NMR(D$_2$O): δ7.37–7.30 (m, 2H), 7.25 (m, 1H), 7.10 (m, 1H), 3.00 (m, 2H), 2.93 (m, 2H).

Elemental analysis: $C_9H_{10}N_2 \cdot 1.0\, HCl \cdot 0.2\, H_2O \cdot 1.0\, NH_4Cl$ (MW=240.65)

|  | C | H | N | Cl |
|---|---|---|---|---|
| Calculated: | 44.92 | 6.49 | 17.46 | 29.46 |
| Found: | 44.94 | 6.48 | 17.58 | 29.60 |

EXAMPLE 165

2,3,4,5-tetrahydro-1H-1-benzazepin-2-one

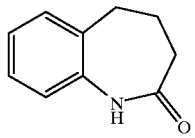

A sample of alpha tetralone (Aldrich, 36.5 g, 0.25 mol) was converted to the title material by the method of EXAMPLE 50 using 19.5 g (0.3 mol) of sodium azide in a mixture of 300 mL of conc $H_2SO_4$ and 100 mL of $CH_2Cl_2$. This procedure yielded after recrystallization from EtOH 12.1 g (30%) of the title product.

EXAMPLE 166

4,5-dihydro-2-methoxy-3H-1-benzazepine

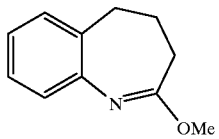

A sample of the title compound of EXAMPLE 165 (3.2 g, 20.0 mmol) was reacted with trimethyloxonium tetrafluoroborate (4.4 g, 30.0 mmol) by the method of EXAMPLE 26 to yield, after chromatography, 2.5 g (73%) of the title material.

EXAMPLE 167

2,3,4,5-tetrahydro-1H-1-benzazepin-2-imine, monohydrochloride

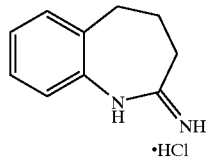

The product of EXAMPLE 166 (1.9 g, 11.1 mmol) in 15 mL of MeOH and 10 mL of $CH_2Cl_2$ was reacted with ammonium chloride (413 mg, 7.8 mmol) by the method of EXAMPLE 27 to yield 1.4 g (88%) of the title material.

HRMS m/z M+ 161.103; $C_{10}H_{13}N_2$ requires 161/108. $^1$H NMR($D_2O$): δ7.44–7.32 (m, 3H), 7.2 (m, 1H), 2.81 (m, 2H), 2.50 (m, 2H), 2.34 (m, 2H).

Elemental analysis: $C_{10}H_{12}N_2 \cdot 1.0$ HCl$\cdot 0.33$ $H_2O$ (MW=202.63)

|  | C | H | N | Cl |
|---|---|---|---|---|
| Calculated: | 59.28 | 6.80 | 14.24 | 17.50 |
| Found: | 59.30 | 6.68 | 13.90 | 17.41 |

EXAMPLE 168

4,4-dimethylpiperidin-2-one

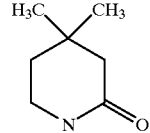

A solution of 3,3-dimethylglutaric anhydride (10 g, 70 mmol) in ammonium hydroxide (conc., 30 mL) was hydrogenated over Pd/$Al_2O_3$ at 1600 psi and 250° C. for 3 h. The flask was cooled to RT and treated with brine (satd., 75 mL) followed by extraction with $CH_2Cl_2$ (150 mL), dried ($Na_2SO_4$) and evaporated to yield a solid, that was purified by chromatography to yield 1.4 g (16%) of the title material. IR (KBr): 3260, 2949, 1655, 1626, 1502, 1338 $^1$H NMR (CDCl$_3$): δ5.98 (br s, 1H), 3.38–3.32 (m, 2H), 2.13 (s, 2H), 1.59 (t, J=5 Hz, 2H), 1.05 (s, 6H)

Elemental analysis: $C_7H_{13}NO\cdot 0.02$ CHCl$_3$ (MW=127.19)

|  | C | H | N |
|---|---|---|---|
| Calculated: | 65.07 | 10.13 | 10.81 |
| Found: | 65.20 | 9.74 | 10.78 |

EXAMPLE 169

2,3,4,5-tetrahydro-4,4-dimethyl-6-methoxypyridine

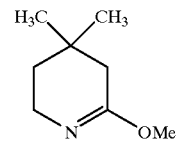

A sample of the title compound of EXAMPLE 168 (636 mg, 5 mmol) was reacted with trimethyloxonium tetrafluoroborate (890 mg, 6 mmol) by the method of EXAMPLE 26 to yield, after chromatography, 550 mg (78%) of the title material.

EXAMPLE 170

4,4-dimethylpiperidin-2-imine, monohydrochloride

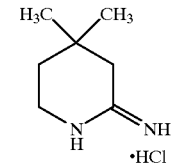

The product of EXAMPLE 169 (550 mg, 3.9 mmol) in 25 mL of MeOH was reacted with ammonium chloride (178 mg, 3.3 mmol) by the method of EXAMPLE 27 to yield 460 mg (86%) of the title material.

DSC: 167.65° C.; MS (EI) m/e, 126 (100 %, M.). IR (KBr) : 3294, 3148, 3009, 2945, 1687; $^1$H NMR(DMSO d$_6$-D$_2$O exchange): δ3.33 (t, J=5 Hz, 2H), 2.34 (s, 2H), 1.60 (t, J=5 Hz,, 2H), 1.00 (s, 6H)

Elemental analysis: C$_7$H$_{14}$N$_2$.1.0 HCl.0.2 H$_2$O.0.2 NH$_4$Cl (MW=176.97)

|  | C | H | N | Cl |
|---|---|---|---|---|
| Calculated: | 47.51 | 9.23 | 17.41 | 24.04 |
| Found: | 47.13 | 9.05 | 17.76 | 24.31 |

EXAMPLE 171

(trans)-octahydro-1H-isoindol-1-one

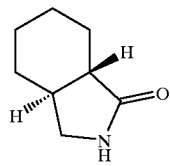

A solution of trans-1,2-cyclohexanedicarboxylic anhydride (10 g, 65 mmol) in ammonium hydroxide (conc., 30 ml) was hydrogenated by the method of EXAMPLE 168 to yield 7.4 g (80%) of the title material.

mp: 85–88° C.; $^1$H NMR(CDCl$_3$): δ6.47 (br s, 1H), 3.42–3.31 (m, 1H), 3.00–2.93 (m, 1H), 2.50–2.35 (m, 1H), 2.07–1.15 (m, 9H).

EXAMPLE 172

(trans)-3a, 4,5,6,7,7a-hexahydro-3-methoxy-1H-isoindole

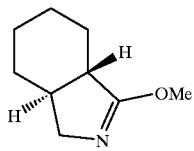

A sample of the title compound of EXAMPLE 171 (1.39 g, 10 mmol) was reacted with trimethyloxonium tetrafluoroborate (1.78 g, 12 mmol) by the method of EXAMPLE 26 to yield, after chromatography, 1.05 g (69%) of the title material.

EXAMPLE 173

(trans)-octahydro-2H-isoindol-1-imine, monohydrochloride

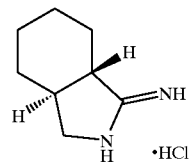

The product of EXAMPLE 172 (1.04 g, 6.79 mmol) in 50 mL of MeOH was reacted with ammonium chloride (359 mg, 6.70 mmol) by the method of EXAMPLE 27 to yield 940 mg (75%) of the title material.

IR (KBr): 3400–2700, 1686 cm$^{-1}$; $^1$H NMR(DMSO d$_6$-D$_2$O exchange): δ3.52–3.45 (m, 1H), 3.28–3.22 (m, 1H), 3.04–2.98 (m, 1H), 2.51–2.43 (m, 1H), 1.90–1.20 (m, 8H).

Elemental analysis: C$_8$H$_{14}$N$_2$1.0 HCl.0.25 H$_2$O.0.25 NH$_4$Cl (MW=192.55)

|  | C | H | N | Cl |
|---|---|---|---|---|
| Calculated: | 49.90 | 8.64 | 16.37 | 23.02 |
| Found: | 50.00 | 8.27 | 16.28 | 23.09 |

EXAMPLE 174 bicyclo[2.2.1]heptan-2-one, oxime

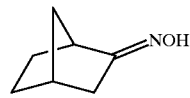

Norcamphor (11 g, 100 mmol) was reacted with hydroxylamine hydrochloride (13.2 g) and sodium acetate (13.1 g) by the method of EXAMPLE 173 to yield, 11.5 g (96%) of the title material.

EXAMPLE 175

2-azabicyclo[3.2.1]octan-3-one, mixture with 3-azabicyclo[3.2.1]octan-2-one

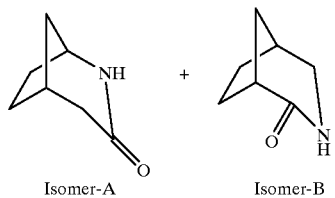

Isomer-A     Isomer-B

The product of EXAMPLE 174 (10 g, 80 mmol) was converted to the title compound mixture of two regioisomers by the method of EXAMPLE 25 using 80% H$_2$SO$_4$. This product mixture was purified by chromatography but not separated into its Isomer-A and Isomer-B components to yield 835 mg (8%), as a clear liquid.

EXAMPLE 176

3-methoxy-2-azabicyclo[3.2.1]oct-2-ene, mixture with 2-methoxy-3-azabicyclo[3.2.1]oct-2-ene

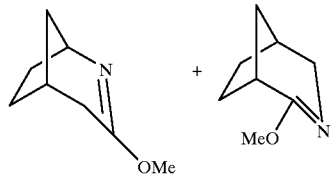

A sample of the title compounds of EXAMPLE 175 (650 mg, 5 mmol) was reacted with trimethyloxonium tetrafluoroborate (890 g, 6 mmol) by the method of EXAMPLE 26 to yield, after chromatography, 550 mg (80%) of the title materials.

EXAMPLE 177

2-azabicyclo[3.2.1]octan-3-imine, monohydrochloride, mixture with 3-azabicyclo[3.2.1]octan-2-imine, monohydrochloride

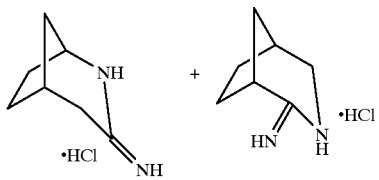

The products of EXAMPLE 176 (530 mg, 3.9 mmol) in 25 mL of MeOH were reacted with ammonium chloride (178 mg, 3.3 mmol) by the method of EXAMPLE 27 to yield 400 mg (67%) of the title materials. MS (EI) m/e;124 (90%, M.), 83 (100%) $^1$H NMR(DMSO $d_6$-$D_2O$ exchange): δ3.44–3.37 (m, 1H), 3.19–3.11(m, 1H), 2.95–2.89 (m, 1H), 2.57–2.50 (m, 2H), 2.07–1.52 (m, 5H).

Elemental analysis: $C_8H_{14}N_2$.1.08 HCl 0.75 $H_2O$.0.4 $NH_4Cl$ (MW=212.500)

|  | C | H | N | Cl |
|---|---|---|---|---|
| Calculated: | 42.36 | 8.22 | 16.94 | 26.44 |
| Found: | 42.70 | 8.27 | 17.03 | 26.65 |

EXAMPLE 178

2,2,2-trichloro-N-(2-propenyl)acetamide

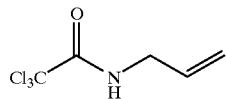

To a stirred solution of allylamine (5 g, 88 mmol) and triethylamine (9.6 g, 95 mmol) in $CH_2Cl_2$ (200 mL) at −10° C. was added trichloroacetyl chloride (16.7 g, 92 mmol). The resulting solution was allowed to gradually warm to RT and stir for 24 h. The reaction solution was extracted with brine (satd., 100 mL) and dried ($Na_2SO_4$) to yield 17 g (96%) of the title compound as a white solid.

EXAMPLE 179

3,3-dichloro-4-(chloromethyl)pyrrolidin-2-one

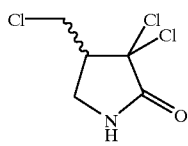

To a stirred solution of the title compound EXAMPLE 178 (15 g, 74 mmol) in xylene (600 mL) under $N_2$ was added $RuCl_2(PPh_3)_3$ (696 mg (0.74 mmol), and the solution was refluxed for 2 h. The solvent was removed and the residue was chromatographed and crystallized (EtOAc) to yield 4.5 g (30%) of the title compound as a solid.

$^1$H NMR(CDCl$_3$): δ7.40 (br s, 1H), 4.00 (dd, J=4, 12 Hz, 1H), 3.76 (dd, J=9, 12 Hz, 1H), 3.70 (dd, J=6, 8 Hz, 1H), 3.28 (dd, J=8, 9 Hz, 1H), 3.12–3.23 (m, 1H).

EXAMPLE 180

4-methylpyrrolidin-2-one

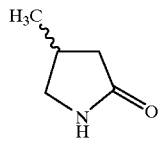

A mixture of the title compound in EXAMPLE 179 (3 g, 15 mmol), tributyltin hydride (14.3 mL) and AIBN (25 mg) was heated at 140° C. for 8 h. The product was chromatographed to yield 900 mg (61%) of the title compound as a solid.

EXAMPLE 181

3,4-dihydro-5-methoxy-3-methyl-2H-pyrrole

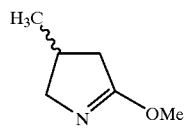

The product of EXAMPLE 180 (500 mg, 5 mmol) was reacted with trimethyloxonium tetrafluoroborate (890 mg, 6 mmol) by the method of EXAMPLE 26 to yield, after chromatography 610 mg of the title material containing traces of solvent.

EXAMPLE 182

4-methylpyrrolidin-2-imine, monohydrochloride

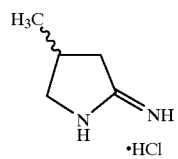

The product of EXAMPLE 181 (610 mg, 5 mmol) in 25 mL of MeOH was reacted with ammonium chloride (200 mg, 4 mmol) by the method of EXAMPLE 27 to yield 500 mg (70%) of the title material.

HRMS m/z M$^+$ 98.0844; $C_5H_{10}N_2$ requires 98.0844.

Elemental analysis: $C_5H_{10}N_2$.HCl 0.25 $H_2O$.0.75 $NH_4Cl$ (MW=179.23).

| | C | H | N | Cl |
|---|---|---|---|---|
| Calculated: | 33.50 | 8.15 | 21.49 | 34.62 |
| Found: | 33.17 | 7.96 | 21.40 | 34.69 |

EXAMPLE 183

2-butylcyclohexanone, oxime

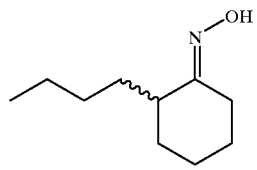

A sample of 2-n-butylcyclohexanone (Aldrich, 10.4 g, 67.2 mmol) was converted to the title compound by the method of EXAMPLE 24 using 7.0 g (100.7 mmol) of hydroxylamine hydrochloride and 9.8 g (120.1 mmol) of NaOAc in a mixture of 75 mL of EtOH and 50 mL of water. The procedure produced 11.3 g (99%) of the crude title compound.

EXAMPLE 184

3-butylhexahydro-1H-azepin-2-one, mixture with 7-butylhexahydro-1H-azepin-2-one

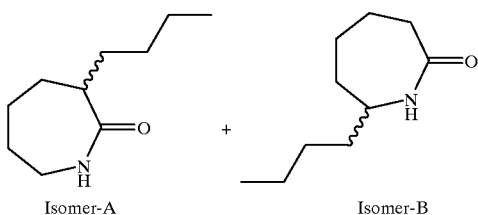

The product of EXAMPLE 184 (11.1 g, 65.6 mmol) was converted to the title compound mixture of two regioisomers by the method of EXAMPLE 29 using 12.3 g (70.0 mmol) of benzene sulfonylchloride. The crude pale yellow solid product mixture (8.3 g) was separated into its Isomer-A and Isomer-B components by chromatography.

EXAMPLE 185

6-butyl-3,4,5,6-tetrahydro-7-methoxy-2H-azepine

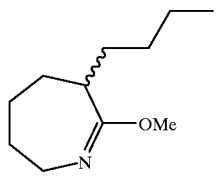

The Isomer-A product of EXAMPLE 184 is reacted with trimethyloxonium tetrafluoroborate by the method of EXAMPLE 26 to produce the title material.

EXAMPLE 186

2-butyl-3,4,5,6-tetrahydro-7-methoxy-2H-azepine

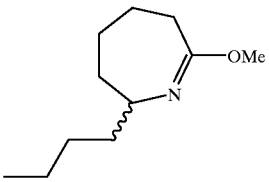

The Isomer-B product of EXAMPLE 184 (0.63 g, 3.7 mmol) was reacted with trimethyloxonium tetrafluoroborate (0.71 g, 4.8 mmol) by the method of EXAMPLE 26 to yield, after chromatography, 0.53 g (84%) of the title material.

Elemental analysis: $C_{11}H_{21}NO \cdot 0.125\ H_2O$ (MW=185.55)

| | C | H | N |
|---|---|---|---|
| Calculated: | 71.21 | 11.54 | 7.55 |
| Found: | 71.14 | 11.73 | 7.25 |

EXAMPLE 187

3-butylhexahydro-1H-azepin-2-imine, monohydrochloride

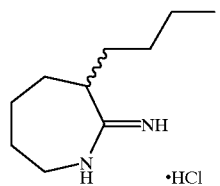

The product of EXAMPLE 185 in MeOH is reacted with ammonium chloride by the method of EXAMPLE 27 to generate the title material.

EXAMPLE 188

7-butylhexahydro-1H-azepin-2-imine, monohydrochloride

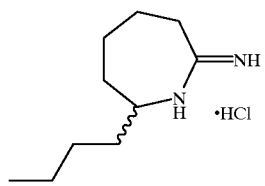

The product of EXAMPLE 186 (500 mg, 2.7 mmol) in 20 mL of MeOH was reacted with ammonium chloride (124 mg, 2.3 mmol) by the method of EXAMPLE 27 to yield 425 mg (74%) of the title material.

$^1$H NMR (400 MHz, CD$_3$OD) δ3.64–3.55 (m, 1H), 2.79 (ddd, 1H, J=14.6, 6.7, 1.5 Hz), 2.61 (ddt, 1H, J=14.6, 6.7, 1.5 Hz), 2.06–1.95 (m, 2H), 1.90–1.81 (m, 1H), 1.76–1.55 (m, 3H), 1.55–1.31 (m, 6H), 0.95 (t, 3H, J=7.1 Hz).

Elemental analysis: $C_{10}H_{20}N_2 \cdot 1.0$ HCl $0.33$ $H_2O \cdot 0.03$ $NH_4Cl$ (MW=212.29)

|  | C | H | N | Cl |
| --- | --- | --- | --- | --- |
| Calculated: | 56.58 | 10.34 | 13.39 | 17.20 |
| Found: | 56.49 | 10.47 | 12.99 | 17.55 |

EXAMPLE 189

2-phenylcyclohexanone, oxime

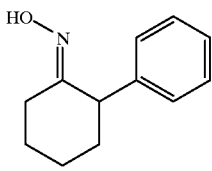

A sample of 2-phenylcyclohexanone (Aldrich, 10.4 g, 60 mmol) was converted to the title compound by the method of EXAMPLE 24 using 7.2 g (104 mmol) of hydroxylamine hydrochloride and 8.4 g (102 mmol) of NaOAc in a mixture of 75 mL of EtOH and 75 mL of water. The procedure produced 11.0 g (97%) of the title material as a white solid.

EXAMPLE 190 hexahydro-7-phenyl-1H-azepin-2-one

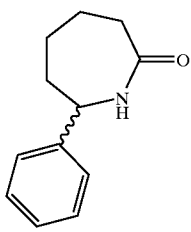

To the product of EXAMPLE 189 (10.9 g, 57.7 mmol) in 60 mL of acetone was added 1N NaOH (64 mL, 64 mmol). After cooling this mixture in an ice bath, benzene sulfonyl-chloride (10.6 g, 60 mmol) was added drop-wise over 5 minutes to the stirred reaction mixture maintained under a $N_2$ atmosphere. The reaction was allowed to warm to room temperature and stir overnight. The filtrate was concentrated and partitioned between EtOAc and brine. The organic layer was dried ($Na_2SO_4$), filtered, and stripped of all solvent under reduced pressure. A white solid was thus obtained and recrystallized from hot methyl t-butyl ether/acetone to yield 3.5 g (32%) of the title material.

EXAMPLE 191

3,4,5,6-tetrahydro-7-methoxy-2-phenyl-2H-azepine

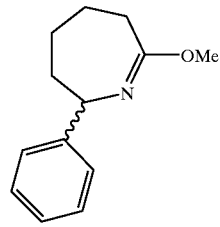

The product of EXAMPLE 29 (1.75 g, 9.3 mmol) was reacted with trimethyloxonium tetrafluoroborate (1.8 g, 12.0 mmol) by the method of EXAMPLE 26 to yield 1.4 g (72%) of the title material.

EXAMPLE 192 hexahydro-7-phenyl-1H-azepin-2-imine, monohydrochloride

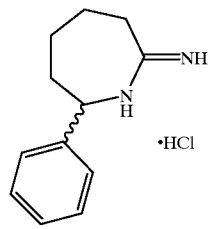

The product of EXAMPLE 191 (1.4 g, 6.9 mmol) in 75 mL of MeOH was reacted with ammonium chloride (0.31 g, 5.9 mmol) by the method of EXAMPLE 27 to yield 1.2 g (77%) of the title material.

$^1$H NMR(CD$_3$OD): δ7.50–7.30 (m, 5H), 2.98 (tt, 1H), 2.74 (dd, 1H), 2.12–1.76 (m, 6H), 1.60 (m, 1H).

Elemental analysis: $C_{12}H_{16}N_2 \cdot HCl \cdot 0.5$ $H_2O$ (MW=233.74)

|  | C | H | N | Cl |
| --- | --- | --- | --- | --- |
| Calculated: | 61.66 | 7.76 | 11.98 | 15.17 |
| Found: | 61.69 | 8.15 | 11.42 | 15.41 |

EXAMPLE 193

2-(2-ethylbutyl)cyclohexanone, oxime

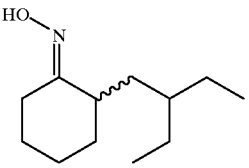

A sample of 2(2-ethyl)butylcyclohexanone (Aldrich, 10.1 g, 55.5 mmol) was converted to the title compound by the method of EXAMPLE 24 using 5.4 g (77.7 mmol) of hydroxylamine hydrochloride and 8.2 g (99.9 mmol) of NaOAc in a mixture of 90 mL of EtOH and 90 mL of water. The procedure produced 11.9 g (100%) of the crude title compound.

EXAMPLE 194

3-(2-ethylbutyl)hexahydro-1H-azepin-2-one, mixture with 7-(2-ethylbutyl)hexahydro-1H-azepin-2-one

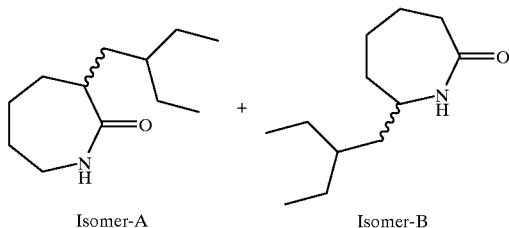

Isomer-A        Isomer-B

The product of EXAMPLE 193 (7.3 g, 37.1 mmol) was converted to the title compound mixture of two regioisomers by the method of EXAMPLE 29 using 7.1 g (40.0 mmol) of benzene sulfonylchloride. The crude pale yellow oil product mixture (7.3 g) was separated into its Isomer-A and Isomer-B components by chromatography.

EXAMPLE 195

6-(2-ethylbutyl)-3,4,5,6-tetrahydro-7-methoxy-2H-azepine

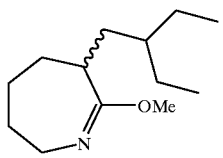

The Isomer-A product of EXAMPLE 194 is reacted with trimethyloxonium tetrafluoroborate by the method of EXAMPLE 26 to produce the title material.

EXAMPLE 196

2-(2-ethylbutyl)-3,4,5,6-tetrahydro-7-methoxy-2H-azepine

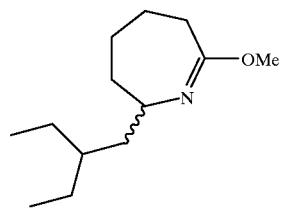

The Isomer-B product of EXAMPLE 194 (520 mg, 2.6 mmol) was reacted with trimethyloxonium tetrafluoroborate (506 mg, 3.4 mmol) by the method of EXAMPLE 26 to yield, after chromatography, 472 mg (85%) of the title material.

EXAMPLE 197

3-(2-ethylbutyl)hexahydro-1H-azepin-2-imine, monohydrochloride

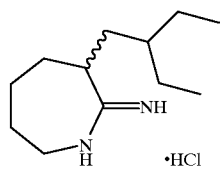

The product of EXAMPLE 195 in MeOH is reacted with ammonium chloride by the method of EXAMPLE 27 to generate the title material.

EXAMPLE 198

7-(2-ethylbutyl)hexahydro-1H-azepin-2-imine, monohydrochloride

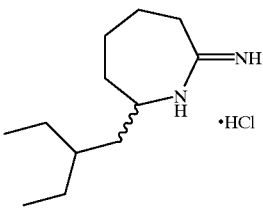

The product of EXAMPLE 196 (470 mg, 2.2 mmol) in 18 mL of MeOH was reacted with ammonium chloride (98 mg, 1.8 mmol) by the method of EXAMPLE 27 to yield 242 mg of the title material.

EXAMPLE 199 hexahydro-7-imino-1H-azepine-2-ethanol, monohydrochloride

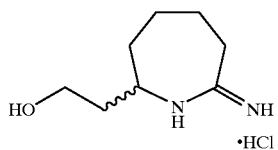

Hexahydro-7-(2-propenyl)-1H-azepin-2-imine, monohydrochloride (the product of EXAMPLE 108) (3.0 g, 14.7 mmol) is dissolved in a mixture of methylene chloride (100 mL) and methanol (50 mL) and cooled to −78° C. Ozone is then bubbled through until a blue color is observed. The reaction is flushed with $N_2$ to remove excess ozone. The reaction mixture is warmed to room temperature and concentrated in vacuo to a residue. The residue is dissolved in ethanol (100 mL), cooled to 0° C., and vigorously stirred as a cold solution of sodium borohydride (0.7 g, 18.5 mmol) in 1:1 ethanol-water is added. The pH of the reaction mixture is maintained by the concomitant addition of 2 M acetic acid in water, maintaining the pH (pH paper) at 8 to 9. After the addition is complete, the mixture is stirred at room temperature for 10 hr, the reaction mixture is acidified to pH 2 with dilute HCl, and the reaction mixture is concentrated in vacuo to a gum. The gum is dissolved in a small amount of ethanol, filtered, evaporated in vacuo to a solid, dissolved in water and applied to an ion exchange column of Dowex 50 (H⁺). The column is washed with deionized water, and the title compound eluted with 2 N HCl. The eluate is concentrated in vacuo to a solid, dissolved in a small amount of water, filtered, and lyophilized to give the title compound. $C_8H_{16}N_2O \cdot HCl$ mw=192.69.

EXAMPLE 200 hexahydro-7-imino-1H-azepine-2-acetic acid, monohydrochloride

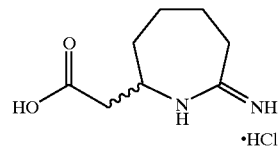

Hexahydro-7-(2-propenyl)-1H-azepin-2-imine, monohydrochloride (the product of EXAMPLE 108) (3.0 g, 14.7 mmol) is dissolved in methyl ethyl ketone (150 mL) and cooled to −78° C. Ozone is then bubbled through until a blue color is observed. A 10% solution of $H_2O_2$ (12 mL) is added at −78° C. The reaction mixture is allowed to warm to room temperature and concentrated in vacuo to a solid. The solid is triturated with diethyl ether, dried, dissolved in water, and lyophilized to give title compound. If purification is necessary, it is effected by dissolving the material in deionized water, and passing into a Dowex 50 ion exchange bed (H⁺). The resin is washed with deionized water, and the product eluted rapidly with 1 N ammonium hydroxide. The solution is rapidly evaporated in vacuo at room temperature, and taken up in water. The pH is adjusted to 6.2 with 1 N HCl. The solution is concentrated in vacuo to a solid, the title compound. $C_8H_{14}N_2O_2 \cdot HCl$ mw=206.67.

EXAMPLE 201 methyl hexhydro-7-imino-1H-azepine-2-acetate, monohydrochloride

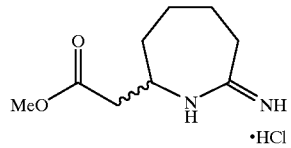

Thionyl chloride (3.5 g, 30 mmol) is added carefully and slowly to a stirring volume of dry cold (−20° C.) methanol (150 mL). After addition is complete, the solution is stirred at −20° C. for 30 min. The title product of EXAMPLE 200 (3.0 g, 14.6 mmol) is dissolved in the minimum of dry methanol and treated with 3A molecular sieves. The mixture is filtered protected from moisture, and added to the cold methanolic HCl solution. The reaction mixture is protected from moisture and allowed to stir at room temperature overnight. The reaction mixture is concentrated in vacuo to give the title product. $C_9H_{16}N_2O_2 \cdot HCl$ mw=220.81.

EXAMPLE 202

2-(2-propenyl)cycloheptanone, oxime

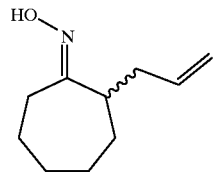

2-carboethoxycycloheptanone (1 mmol), finely powdered potassium carbonate (2 mmol), allyl bromide (1.5 mmol), and tetrabutyl ammonium iodide (10 mg/mmol) are combined in dry DMF (1.25 mL/mmol) and stirred under $N_2$ at 55 to 60° C. for 16 to 18 hours. The room temperature reaction mixture is poured into water and extracted with $Et_2O$ and EtOAc. The combined organics are washed with brine, dried, and stripped of all solvent under reduced pressure to provide 2-allyl-2-carboethoxycycloheptanone. This material is combined with lithium chloride (5 mmol), water (1.05 mmol) and dimethyl sulfoxide (5 mL/mmol) and the mixture refluxed for approximately 4 hrs. The mixture is poured into water and extracted with $Et_2O$ and EtOAc. The combined organics are washed with brine, dried, and stripped of all solvent under reduced pressure to provide 2-allylcycloheptanone. A sample of the 2-allylcycloheptanone is converted to the title compound by the method of EXAMPLE 24 using hydroxylamine hydrochloride and NaOAc in a mixture of EtOH and water.

EXAMPLE 203 octahydro-3-(2-propenyl)azocin-2-one, mixture with octahydro-8-(2-propenyl)azocin-2-one

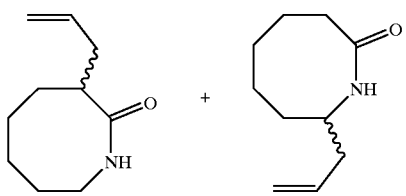

The product of EXAMPLE 202 is converted to the title compound mixture of two regioisomers by the method of EXAMPLE 29 using benzene sulfonylchloride. The crude product mixture is separated into its Isomer-A and Isomer-B components by chromatography.

EXAMPLE 204

3,4,5,6,7,8-hexahydro-2-methoxy-3-(2-propenyl)azocine

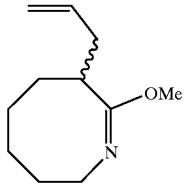

The Isomer-A product of EXAMPLE 203 is reacted with trimethyloxonium tetrafluoroborate by the method of EXAMPLE 26 to produce the title material.

EXAMPLE 205

2,3,4,5,6,7-hexahydro-8-methoxy-2-(2-propenyl)azocine

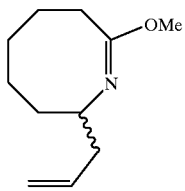

The Isomer-B product of EXAMPLE 203 is reacted with trimethyloxonium tetrafluoroborate by the method of EXAMPLE 26 to produce the title material.

EXAMPLE 206 octahydro-3-(2-propenyl)azocin-2-imine, monohydrochloride

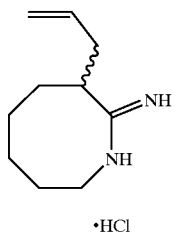

The product of EXAMPLE 204 in MeOH is reacted with ammonium chloride by the method of EXAMPLE 27 to generate the title material.

EXAMPLE 207 octahydro-3-(2-propenyl)azocin-2-imine, monohydrochloride

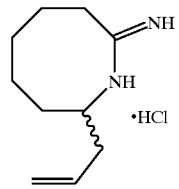

The product of EXAMPLE 205 in MeOH is reacted with ammonium chloride by the method of EXAMPLE 27 to generate the title material.

EXAMPLE 208

N-(2-butenyl)-2,2,2-trichloroacetamide

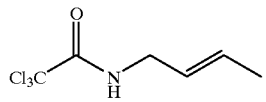

A solution of 3-butene-2-ol (8.7 mL, 100 mmol) in THF (50 mL) was added to potassium hydride (KH, 600 mg, 15 mmol) over 15 min. The resulting alkoxide solution was added to a stirred solution of trichloroacetonitrile (10.03 mL, 100 mmol) in ether (100 mL) at −10° C. The solution was stirred at 0° C. for 3 h, followed by removal of solvent under reduced pressure (temperature <25 ° C.); pentane (400 mL) and methanol (1 mL) were added, and the mixture filtered. Concentration afforded a yellow oil (17.4 g). The oil was dissolved in xylene (450 mL) and refluxed for 2.5 h. The solvent was removed to yield 16.8 g of the title compound as a white solid.

EXAMPLE 209

3,3-dichloro-4-(1-chloroethyl)pyrrolidin-2-one

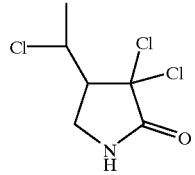

A mixture of the title compound in EXAMPLE 208 was treated with $RuCl_2(PPh_3)_3$ in refluxing xylene by the method of EXAMPLE 179 to produce the title material.

EXAMPLE 210

4-ethylpyrrolidin-2-one

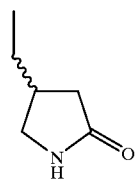

A mixture of the title compound in EXAMPLE 209 was treated with tributyltin hydride and AIBN by the method of EXAMPLE 180 to produce the title material.

EXAMPLE 211

3-ethyl-3,4-dihydro-5-methoxy-2H-pyrrole

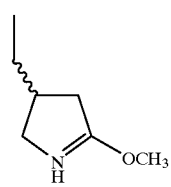

The product of EXAMPLE 180 is reacted with trimethyloxonium tetrafluoroborate by the method of EXAMPLE 26 to produce the title material.

EXAMPLE 212

4-ethylpyrrolidin-2-imine, monohydrochloride

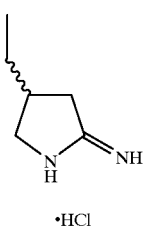

The product of EXAMPLE 211 in MeOH is reacted with ammonium chloride by the method of EXAMPLE 27 to generate the title material.

EXAMPLE 213

2,2,2-trichloro-N-(2-methylenebutyl)acetamide

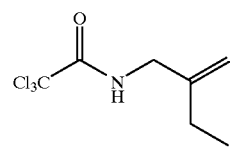

Cis-2-pentene-1-ol was treated with NaH and trichloroacetonitrile followed by work up and treatment in refluxing xylene by the method of EXAMPLE 208 to produce the material.

EXAMPLE 214

3,3-dichloro-4-(chloromethyl)-5-ethyl-pyrrolidin-2-one

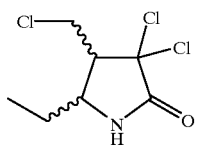

A mixture of the title compound in EXAMPLE 213 was treated with $RuCl_2(PPh_3)_3$ in refluxing xylene by the method of EXAMPLE 179 to produce the title material.

EXAMPLE 215

5-ethyl-4-methylpyrrolidin-2-one

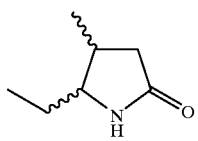

A mixture of the title compound in EXAMPLE 214 was treated with tributyltin hydride and AIBN by the method of EXAMPLE 180 to produce the title material.

EXAMPLE 216

2-ethyl-3,4-dihydro-5-methoxy-3-methyl-2H-pyrrole

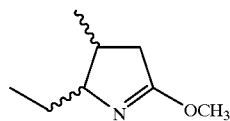

The product of EXAMPLE 215 is reacted with trimethyloxonium tetrafluoroborate by the method of EXAMPLE 26 to produce the title material.

EXAMPLE 217

5-ethyl-4-methylpyrrolidin-2-imine, monohydrochloride

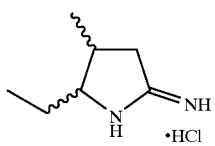

The product of EXAMPLE 216 in MeOH is reacted with ammonium chloride by the method of EXAMPLE 27 to generate the title material.

EXAMPLE 218

3,4-dihydro-5-methoxy-2S-(methoxymethyl)-2H-pyrrole

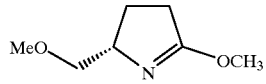

S-(+)-5-(hydroxymethyl)-2-pyrrolidinone is reacted with trimethyloxonium tetrafluoroborate (2.2 equivelants) by the method of EXAMPLE 26 to produce the title material.

EXAMPLE 219

5S-(methoxymethyl)pyrrolidin-2-imine, monohydrochloride

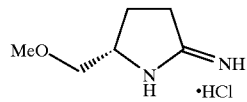

The product of EXAMPLE 218 in MeOH is reacted with ammonium chloride by the method of EXAMPLE 27 to generate the title material.

EXAMPLE 220

3,4-dihydro-5-methoxy-2R-(methoxymethyl)-2H-pyrrole

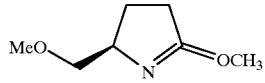

R-(−)-5-(hydroxymethyl)-2-pyrrolidinone is reacted with trimethyloxonium tetrafluoroborate (2.2 equivelants) by the method of EXAMPLE 26 to produce the title material.

EXAMPLE 221

5R-(methoxymethyl)pyrrolidin-2-imine, monohydrochloride

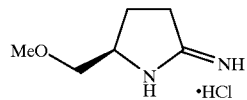

The product of EXAMPLE 220 in MeOH is reacted with ammonium chloride by the method of EXAMPLE 27 to generate the title material.

EXAMPLE 222 ethyl 3,4-dihydro-5-methoxy-2H-pyrrole-2S-carboxylate

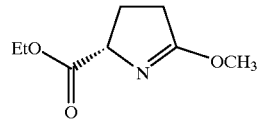

Ethyl (S)-(+)-2-pyrrolidinone-5-carboxylate is reacted with trimethyloxonium tetrafluoroborate by the method of EXAMPLE 26 to produce the title material.

EXAMPLE 223 ethyl 5-iminopyrrolidine-2S-carboxylate, monohydrochloride

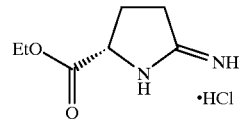

The product of EXAMPLE 222 in MeOH is reacted with ammonium chloride by the method of EXAMPLE 27 to generate the title material.

EXAMPLE 224

5S-(bromomethyl)pyrrolidin-2-one

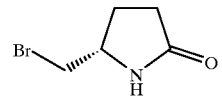

A solution of S-(+)-5-(hydroxymethyl)-2-pyrrolidinone (2 g, 17.4 mmol) in CH$_2$Cl$_2$ (160 mL) was treated with triphenylphosphine (10.5 g, 40 mmol) and carbontetrabromide (13.25 g, 40 mmol). The resulting solution was stirred for 18 h followed by concentration and chromatography (40:1 EtOAc/hexane, silica gel) to yield 1.32 g of the title compound as a white solid.

EXAMPLE 225

3-[[(5-oxopyrrolidin-2S-yl)methyl]oxy]-2S-[[(phenylmethoxy)carbonyl]amino]propanoic acid

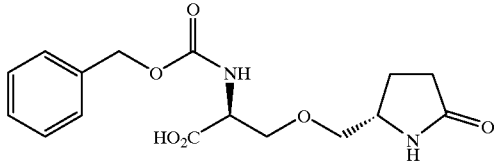

A solution of N-α-Cbz-serine in DMF is treated with 2 equivalents of NaH at 0° C., followed by the addition of the title compound of EXAMPLE 224. The resulting solution is stirred for 5 h at RT, water is added and the mixture extracted with EtOAc. The solution is acidified to pH 3.5 with citric acid and extracted with EtOAc, dried and concentrated to yield the title compound.

EXAMPLE 226 methyl 3-[[(5-oxopyrrolidin-2S-yl)methyl]oxy]-2S-[[(phenylmethoxy)carbonyl]amino]propanoate

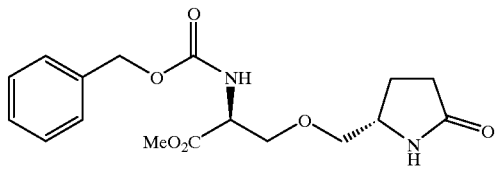

The product of EXAMPLE 225 in DMF is treated with cesium carbonate followed by methyl iodide. The resulting mixture is filtered then partioned between EtOAc and water. The organic phase is washed with brine, dried and concentrated to yield the title compound.

EXAMPLE 227 methyl 3-[[(3,4-dihydro-5-methoxy-2H-pyrrolidin-2S-yl)methyl]oxy]-2S-[[(phenylmethoxy)carbonyl]amino]propanoate

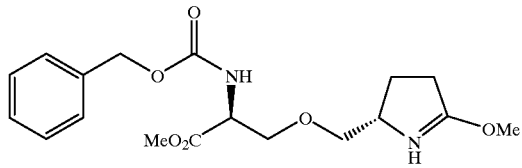

The product of EXAMPLE 226 is reacted with trimethyloxonium tetrafluoroborate by the method of EXAMPLE 26 to produce the title material.

EXAMPLE 228 methyl 3-[[(5-iminopyrrolidin-2S-yl)methyl]oxy]-2S-[[(phenylmethoxy)carbonyl]amino]propanoate, monohydrochloride

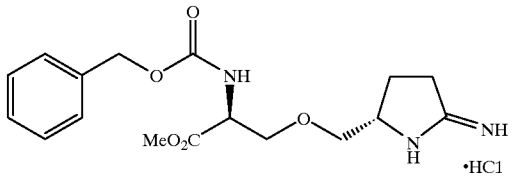

The product of EXAMPLE 227 in MeOH is reacted with ammonium chloride by the method of EXAMPLE 27 to generate the title material.

EXAMPLE 229 methyl 2S-amino-3-[[(5-iminopyrrolidin-2S-yl)methyl]oxy]propanoate, dihydrochloride

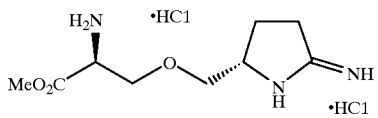

The product of EXAMPLE 228 in MeOH/HCl is reacted with $H_2$ over Pd/C 10% to generate the title material.

EXAMPLE 230

3-(7-iminoazepin-2-yl)-1,2-propanediol, monohydrochloride

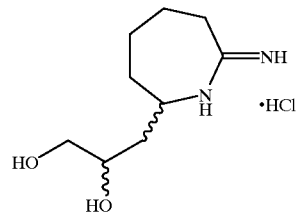

To the product of EXAMPLE 108 in a mixture of acetone and THF is added osmium tetroxide. An aqueous solution of morpholine N-oxide is then added to the reaction and the mixture is stirred at room temperature over night. Sodium bisulfite is then added and this mixture is evaporated in vacuo to a solid. The solid is extracted with methanol thrice, and the combined extracts are evaporated in vacuo to a solid. This solid is dissolved in water and applied to a Dowex-50 ion exchange column (H⁺), which is eluted with water and then 0.2 N HCl to yield the title compound.

EXAMPLE 231

6-[(tetrahydropyran-2-yl)oxy]hex-2-en-1-ol

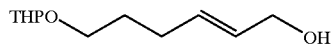

The title compound was prepared from the mono THP ether of 1,4-butanediol as reported in V. S. Martin, et. al., *Tet. Lett.* vol. 31, No. 5, pp 763–766 1990.

EXAMPLE 232

2,2,2-trichloro-N-[1-ethenyl-4-[(tetrahydropyran-2-yl)oxy]butyl]acetamide

The product of EXAMPLE 231 is treated with NaH and trichloroacetonitrile followed by work up and treatment in refluxing xylene by the method of EXAMPLE 208 to produce the material.

EXAMPLE 233

3,3-dichloro-4-(chloromethyl)-5-[3-[(tetrahydropyran-2-yl)oxy]propyl]pyrrolidin-2-one

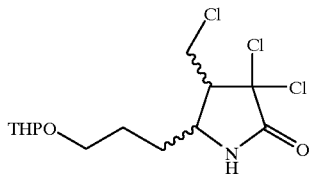

A mixture of the title compound in EXAMPLE 232 is treated with RuCl$_2$(PPh$_3$)$_3$ in refluxing xylene by the method of EXAMPLE 179 to produce the material.

EXAMPLE 234

4-methyl-5-[3-[(tetrahydropyran-2-yl)oxy]propyl]pyrrolidin-2-one

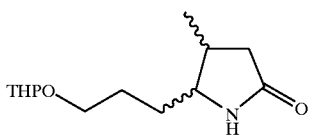

A mixture of the title compound in EXAMPLE 233 is treated with tributyltin hydride and AIBN by the method of EXAMPLE 180 to produce the title product.

EXAMPLE 235

5-(3-hydroxypropyl)-4-methylpyrrolidin-2-one

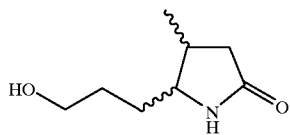

A mixture of the title compound of EXAMPLE 234 is treated with acetic acid:THF:water (4:2:1), and concentrated. The resulting material is purified by column chromatography to yield the title material.

EXAMPLE 236

5-(3-bromopropyl)-4-methylpyrrolidin-2-one

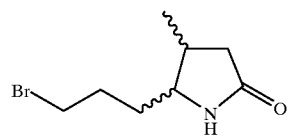

A mixture of the title compound of EXAMPLE 235 is treated with triphenylphosphine and carbon tetrabromide by the method of EXAMPLE 224 to generate the title material.

EXAMPLE 237 ethyl α-amino-3-methyl-5-oxopyrrolidine-2-pentanoate

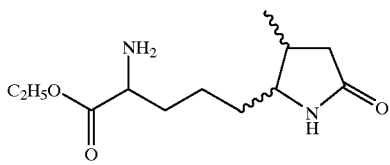

A solution of N-(diphenylmethylene)glycine ethyl ester (Aldrich, 37 mmol) in THF (20 mL) is added to −72° C. solution of sodium bis (trimethylsilylamide) (35 mmol, 0.5 M in THF), while the solution is kept below −65° C. The resulting solution is then stirred at −72° C. for 30 min.; followed by the rapid addition of a cooled solution (−72° C.) of the product from EXAMPLE 236 (24 mmol) in THF via canula. The cooling bath is removed immediately and the mixture allowed to warm to 0° C. for 4 h. The reaction mixture is partitioned between ether and 10% aqueous sodium bisulfate, then-dried and concentrated. The product is purified by column chromatography. This intermediate is then treated with 0.1 N aqueous hydrochloric acid for 3 h, followed by extraction with ether and lyophilization of the aqueous solution, to yield the title material.

EXAMPLE 238 ethyl α-[[(1,1-dimethylethoxy)carbonyl]amino]-3-methyl-5-oxopyrrolidine-2-pentanoate

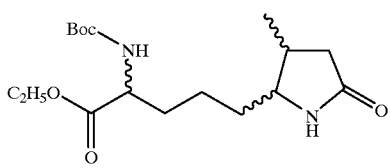

A solution of compound in EXAMPLE 237 is treated with di-t-butyldicarbonate in dichloromethane with triethylamine present. The reaction mixture is extracted with water, dried (MgSO$_4$), filtered and stripped to afford the title compound.

EXAMPLE 239 ethyl α-[[(1,1-dimethylethoxy)carbonyl]amino]-3,4-dihydro-5-methoxy-3-methylpyrrolidine-2-pentanoate

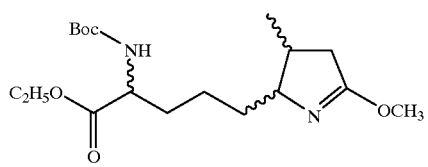

The product of EXAMPLE 238 is reacted with trimethyloxonium tetrafluoroborate by the method of EXAMPLE 26 to produce the title material.

EXAMPLE 240 ethyl α-amino-5-imino-3-methylpyrrolidine-2-pentanoate, dihydrochloride

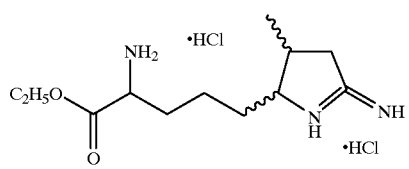

The product of EXAMPLE 239 in MeOH is reacted with ammonium chloride by the method of EXAMPLE 27. This material is then treated with 3M HCl/ethyl acetate to generate the title material.

EXAMPLE 241 hexahydro-7-[(oxiran-2-yl)methyl]-1H-azepin-2-one

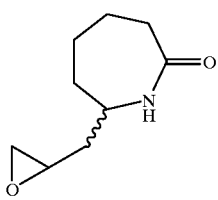

The title product isomer B of EXAMPLE 104 (2.99 g, 19.5 mmol) in 150 mL of $CH_2Cl_2$ was refluxed with meta-chloroperbenzoic acid (MCPBA, 5.05 g, 29.3 mmol) for 3 hr. After stirring at room temperature overnight, an additional 1.0 g (5.8 mmol) of MCPBA was added and the reaction re-heated to reflux for an additional 6 hr. Solvent removal, followed by dissolution in EtOAc (150 mL) and washing 3×50 mL with saturated $NaHCO_3$ provided crude desired product. Purification via flash column chromatography using 100% EtOAc and deactivated silica gel yielded 2.25 g (68%) of the title compound.

EXAMPLE 242 ethyl α-[(diphenylmethylene)amino]hexahydro-7-oxo-1H-azepine-2-pentanoate

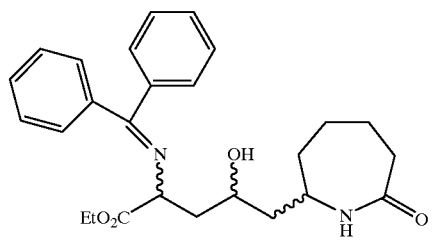

Under an argon atmosphere, the anion of title product isomer B of EXAMPLE 241 (1.0 g, 5.91 mmol) is formed in tetrahydrofuran (THF, 30 mL) at −78° C. with lithium bis(trimethylsilyl)amide in THF (5.91 mmol). The solution in warmed to −60° C., then cooled back to −78° C. To this is added the anion of N-(diphenylmethylene)glycine ethyl ester (formed by its reaction with lithium bis(trimethylsilyl) amide in THF (5.91 mmol) at −78° C. The solution is allowed to warm to room temperature overnight. Quenching with saturated $NH_4Cl$, followed by extraction into EtOAc (3×100 mL) provides crude title material and its lactone derivative. Purification via flash column chromatography yields clean title compound.

EXAMPLE 243 ethyl α-[(diphenylmethylene)amino]-3,4,5,6-tetrahydro-,γ7-dimethoxy-2H-azepine-2-pentanoate

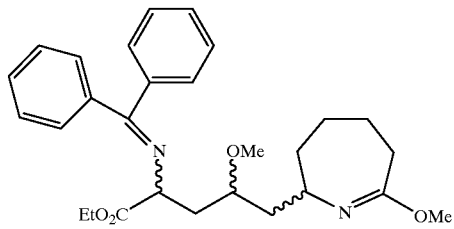

The title product of EXAMPLE 242 is treated with trimethyloxonium tetraflouroborate (two equivalents) in $CH_2Cl_2$ by the method of EXAMPLE 26 to yield title material.

EXAMPLE 244 ethyl α-amino-7-imino-γ-methoxy-1H-azepine-2-pentanoate, dihydrochloride

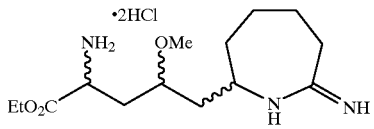

The product of EXAMPLE 243 in MeOH is reacted with ammonium chloride by the method of EXAMPLE 27. This material is then lyophilized from aqueous HCl to generate the title material.

EXAMPLE 245 ethyl 2-amino-5-(hexahydro-7-oxo-1H-azepin-2-yl)-3pentenoate, monohydrochloride

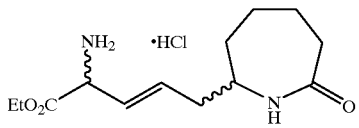

The product of EXAMPLE 242 is stirred with aqueous HCl to yield the title product.

EXAMPLE 246 ethyl α-aminohexahydro-7-oxo-1H-azepine-2-pentanoate, monohydrochloride

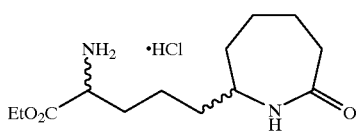

The product of EXAMPLE 245 is reduced via hydrogenation using palladium on carbon as catalyst to produce the title material.

EXAMPLE 247 ethyl hexahydro-7-oxo-α-[[(phenylmethoxy)carbonyl]amino]-1H-azepine-2-pentanoate

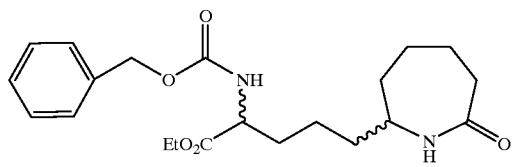

The product of EXAMPLE 246 is treated with benzyl chloroformate under standard conditions to yield title product.

EXAMPLE 248 ethyl 3,4,5, 6-tetrahydro-7-methoxy-α[[(phenylmethoxy)carbonyl]amino]-2H-azepine-2-pentanoate

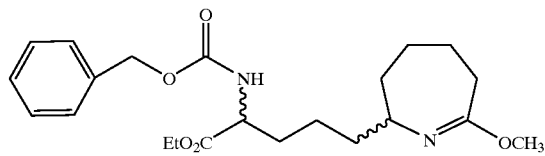

The product of EXAMPLE 247 is treated with trimethyloxonium tetraflouroborate in CH$_2$Cl$_2$ by the method of EXAMPLE 26 to yield title material.

EXAMPLE 249 ethyl hexahydro-7-imino-[[(phenylmethoxy)carbonyl]amino]-1H-azepine-2-pentanoate, monohydrochloride

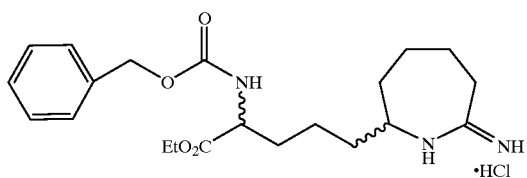

The product of EXAMPLE 248 in MeOH is reacted with ammonium chloride by the method of EXAMPLE 27 to generate the title material.

EXAMPLE 250 ethyl α-aminohexahydro-7-imino-1H-azepine-2-pentanoate, dihydrochloride

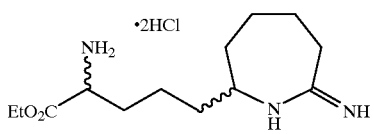

The product of EXAMPLE 249 is reduced using hydrogen and Pd/C as catalyst to yield the title product after lyophilization from aqueous HCl.

EXAMPLE 251

2-(cyclohexen-1-yl)cyclohexanone, oxime

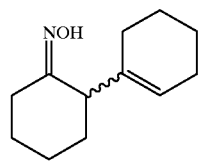

A sample of the 2-(1-cyclohexenyl)cyclohexanone (Lancaster) is converted to the title compound by the method of EXAMPLE 24 using hydroxylamine hydrochloride and NaOAc in a mixture of EtOH and water.

EXAMPLE 252

7-(cyclohexen-1-yl)hexahydro-1H-azepin-2-one

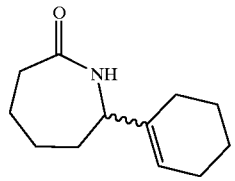

The product of EXAMPLE 251 is converted to the title compound by stirring it with the reagent trimethylsilyl polyphosphate in benzene (preformed by refluxing a mixture of phosphorous pentoxide and hexamethyldisiloxane in benzene until the mixture becomes homogeneous in appearance) at room temperature overnight followed by an aqueous quench and workup.

EXAMPLE 253

2-(cyclohexen-1-yl)-3,4,5,6-tetrahydro-7-methoxy-2H-azepine

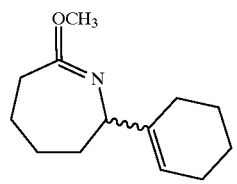

The product of EXAMPLE 252 is reacted with trimethyloxonium tetrafluoroborate by the method of EXAMPLE 26 to produce the title material.

EXAMPLE 254

7-(cyclohexen-1-yl)hexahydro-1H-azepin-2-imine, monohydrochloride

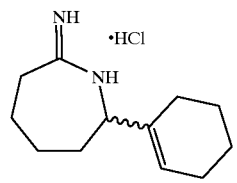

The product of EXAMPLE 253 in MeOH is reacted with ammonium chloride by the method of EXAMPLE 27 to generate the title material.

EXAMPLE 255

2-(2-butynyl)cyclohexanone, oxime

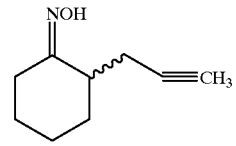

A sample of the 2-carboethoxycyclohexanone is reacted with 1-bromo-2-butyne by the method of EXAMPLE 202 using potassium carbonate in DMF at 60° C. followed decarboethoxylation in refluxing mixture of DMSO, lithium chloride, and water followed by conversion to its oxime using a mixture of hydroxylamine hydrochloride, NaOAc, EtOH and water.

EXAMPLE 256

7-(2-butynyl)hexahydro-1H-azepin-2-one

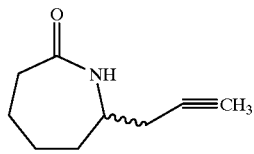

The product of EXAMPLE 255 is converted to the title compound by the method of EXAMPLE 29 using benzene sulfonylchloride.

EXAMPLE 257

2-(2-butynyl)-3,4,5,6-tetrahydro-7-methoxy-2H-azepine

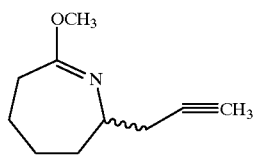

The product of EXAMPLE 256 is reacted with trimethyloxonium tetrafluoroborate by the method of EXAMPLE 26 to produce the title material.

EXAMPLE 258

7-(2-butynyl)hexahydro-1H-azepin-2-imine, monohydrochloride

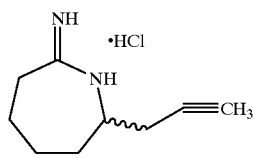

The product of EXAMPLE 257 in MeOH is reacted with ammonium chloride by the method of EXAMPLE 27 to generate the title material.

EXAMPLE 259

1,1-dimethylethyl N-[1-ethenyl-4-(3-methyl-5-oxopyrrolidin-2-yl)butyl]carbamate

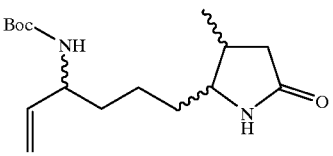

To a stirring solution of the product of EXAMPLE 238 (20 mmol) in dry toluene cooled to −70° C. is added dropwise 1M DIBAL-H in toluene (40 mL, 40 mmol). The solution is stirred for an additional 20 min, and the reaction is quenched with MeOH. Upon removal of the ice bath, 150 mL of saturated solution of Rochelle salt is added to the reaction. After stirring for 1 h, the layers are separated. The aqueous layer is extracted with EtOAc. The combined organic layers are washed with H₂O, dried, filtered, and concentrated. The residue is purified by chromatography to yield the aldehyde which is directly used in the next step. To a stirring suspension of methyltriphenylphosphonium bromide (2.18 g, 6.1 mmol) in Et₂O is added dropwise 0.5 M potassium hexamethyldisilazide in toluene (12.2 mL, 6.1 mmol). After stirring for 1.5 h, the aldehyde from above (6.1 mmol) in Et₂O is added. After 16 h, a white solid is filtered from the reaction and the filtrate is concentrated. The residue is purified by chromatography to yield the title compound.

EXAMPLE 260

1,1-dimethylethyl N-[1-(1,2-dihydroxyethyl)-4-(3-methyl-5-oxopyrrolidin-2-yl)butyl]carbamate

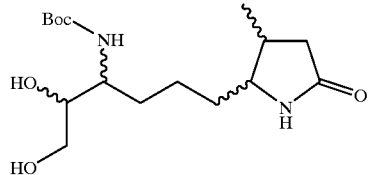

To a stirring solution of the compound from EXAMPLE 259 (3.3 mmol) in 80 mL of acetone:H₂O (3:1) is added N-methylmorpholine N-oxide (0.64 g, 4.8 mmol) and 2.5% OsO₄ in t-BuOH (3.4 mL, 3.4 mmol). After 18 h, 120 mL of H₂O, 8 g of celite, and 1.6 g Na₂S₂O₁ is added to the reaction. The reaction is filtered through a pad of wet celite. To the filtrate is added 200 mL of 1M KHSO₄. The filtrate is extracted with 3×200 mL EtOAc. The combined organic layers are dried, filtered, and stripped. The residue is purified by chromatography to yield the title compound.

EXAMPLE 261

1,1-dimethylethyl N-[4-(3-methyl-2-oxopyrrolidin-2-yl)-1-(2-oxo-1,3-dioxolan-4-yl)butyl]carbamate

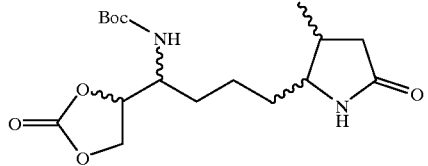

The product of EXAMPLE 260 in pyridine is treated with phosgene in toluene for 1 h, to produce the title material.

EXAMPLE 262

1,1-dimethylethyl N-[4-(3,4-dihydro-5-methoxy-3-methyl-2H-pyrrol-2-yl)-1-(2-oxo-1,3-dioxolan-4-yl)butyl]carbamate

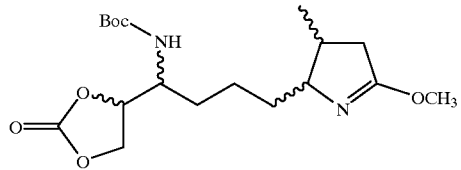

The product of EXAMPLE 261 is reacted with trimethyloxonium tetrafluoroborate by the method of EXAMPLE 26 to produce the title material.

EXAMPLE 263

4-[1-amino-4-(5-imino-3-methylpyrrolidin-2-yl)butyl]-1,3-dioxolan-2-one, dihydrochloride

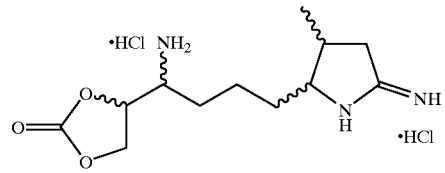

The product of EXAMPLE 262 in MeOH is reacted with ammonium chloride by the method of EXAMPLE 27, then treated with 3M HCl/EtOAc to generate the title material.

EXAMPLE 264

3-amino-6-(5-iminopyrrolidin-2-yl)-1,2-hexanediol

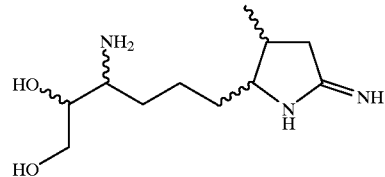

The product of EXAMPLE 263 is treated with aqueous barium hydroxide at 70° C. to yield the title material.

EXAMPLE 265

4-methyl-5-(2-propenyl)pyrrolidin-2-one

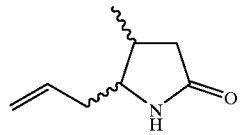

The product of EXAMPLE 235 is treated with PTSA in refluxing toluene, with a Dean-Stark trap to remove water. The solvent is removed to yield the title material.

EXAMPLE 266

3,4-dihydro-5-methoxy-3-methyl-2-(2-propenyl)-2H-pyrrole

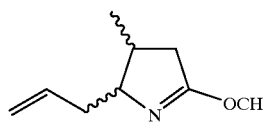

The product of EXAMPLE 265 is reacted with trimethyloxonium tetrafluoroborate by the method of EXAMPLE 26 to produce the title material.

EXAMPLE 267

4-methyl-5-(2-propenyl)pyrrolidin-2-imine, monohydrochloride

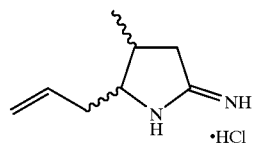

The product of EXAMPLE 266 in MeOH is reacted with ammonium chloride by the method of EXAMPLE 27 to generate the title material.

EXAMPLE 268

1,1-dimethylethyl N-[4-(hexahydro-7-oxo-1H-azepin-2-yl)-1-(2-propenyl)butyl]carbamate

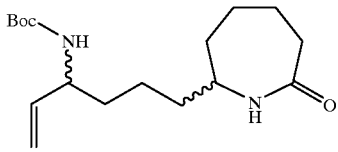

The product of EXAMPLE 246 is treated with di-t-butyldicarbonate by the method of EXAMPLE 238. The resulting Boc-protected product is then reacted with DIBAL and then methyltriphenyl-phosphonium bromide by the method of EXAMPLE 260 to generate the title material.

EXAMPLE 269

1,1-dimethylethyl N-[1-(1,2-dihydroxyethyl)-4-(hexahydro-7-oxo-1H-azepin-2-yl)butyl]carbamate

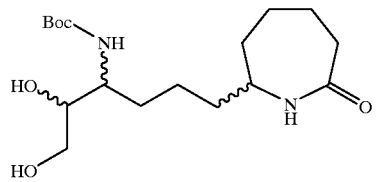

To the product of EXAMPLE 268 in a mixture of acetone and THF is added osmium tetroxide. An aqueous solution of morpholine N-oxide is then added to the reaction and the mixture is stirred at room temperature overnight. Sodium bisulfite is then added and this mixture after diluting with EtOAc is washed with brine, dried, filtered and stripped of all solvent under reduced pressure. The residue is purified by chromatography to yield the title compound.

EXAMPLE 270

1,1-dimethylethyl N-[4-(hexahydro-7-oxo-1H-azepin-2-yl)-1-(2-oxo-1,3-dioxolan-4-yl)butyl]carbamate

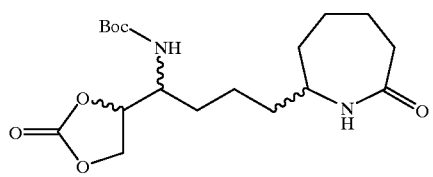

The product of EXAMPLE 269 is reacted with phosgene by the method of EXAMPLE 261, to generate the title material.

EXAMPLE 271

1,1-dimethylethyl N-[1-(2-oxo-1,3-dioxolan-4-yl)-4-(3,4,5,6-tetrahydro-7-methoxy-2H-azepin-2-yl)butyl]carbamate

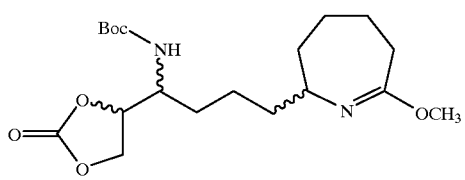

The product of EXAMPLE 270 is reacted with trimethyloxonium tetrafluoroborate by the method of EXAMPLE 26 to produce the title material.

EXAMPLE 272

4-[1-amino-4-(hexahydro-7-imino-1H-azepin-2-yl)butyl]-1,3-dioxolan-2-one, dihydrochloride

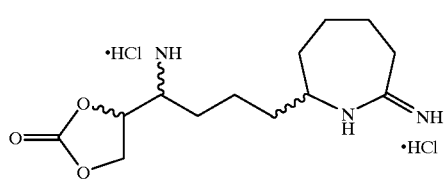

The product of EXAMPLE 271 in MeOH is reacted with ammonium chloride by the method of EXAMPLE 27. This product is then treated with 3M HCl/EtOAc to generate the title material.

EXAMPLE 273

3-amino-6-(hexahydro-7-imino-1H-azepin-2-yl)-1,2-hexanediol

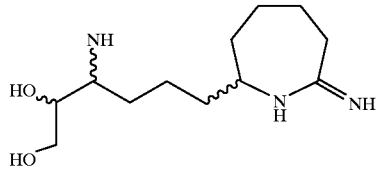

The product of EXAMPLE 272 is treated with aqueous barium hydroxide at 70° C., to yield the title material.

EXAMPLE 274

2S-amino-3-[[(5-iminopyrrolidin-2S-yl)methyl]oxy] propanoic acid, dihydrochloride

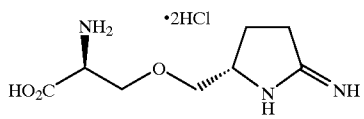

The product of EXAMPLE 229 in 2N HCl is refluxed for 1 h, followed by lyophilization to generate the title material.

EXAMPLE 275 hexahydro-7-(2-propenyl)-1H-azepin-2-one, oxime

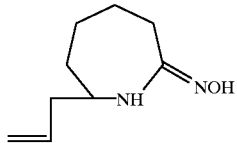

Into a 50 mL roundbottom flask under an argon atmosphere was placed hydroxylamine hydrochloride (0.14 g, 2.02 mmol) and sodium methoxide (0.107 g, 1.99 mmol) in methanol (15 mL). To this was added the product of EXAMPLE 106 (0.29 g, 1.73 mmol). The reaction was heated to reflux for 12.5 h. The reaction was cooled to room temperature and all solvent removed in vacuo. The product was purified via reverse phase chromatography using a YMC ODS2 (20×25 mm) column and a mobile phase of 30% acetonitrile/water.

$^1$H NMR (400 MHz, D$_2$O) δ5.9–5.8 (m, 1H), 5.3–5.15 (m, 2H), 3.8–3.7 (m, 1H), 2.75–2.65 (m, 1H), 2.6–2.4 (m, 3H), 2.0–1.85 (m, 3H,), 1.75–1.6 (m, 1H), 1.55–1.4 (m, 2H).

Elemental analysis: C$_9$H$_{16}$N$_2$O.1.3 HCl.1.1 H$_2$O (MW=235.46)

|  | C | H | N | Cl |
|---|---|---|---|---|
| Calculated: | 45.91 | 8.35 | 11.90 | 19.57 |
| Found: | 45.96 | 8.17 | 11.65 | 19.67 |

EXAMPLE 276 hexahydro-2-(2-propenyl)-1H-azepin-2-one, oxime

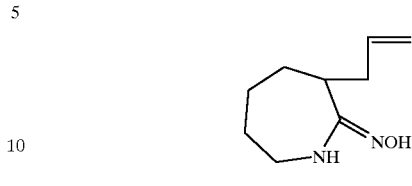

Following the method of EXAMPLE 275, the title compound was prepared from the title product of EXAMPLE 105.

$^1$H NMR (300 MHz, D$_2$O) δ5.9–5.7 (m, 1H), 5.3–5.1 (m, 2H), 3.6–3.5 (m, 2H), 2.85–2.75 (m, 1H), 2.65–2.55 (m, 1H), 2.45–2.35 (m, 1H,), 1.9–1.5 (m, 7H).

Elemental analysis: C$_9$H$_{16}$N$_2$O.1.05 HCl.0.5 H$_2$O (MW=217.33)

|  | C | H | N | Cl |
|---|---|---|---|---|
| Calculated: | 49.74 | 8.46 | 12.89 | 17.13 |
| Found: | 49.73 | 8.11 | 12.82 | 17.30 |

EXAMPLE 277

3-hydroxy-2-imino-6-methylpiperidine acetate

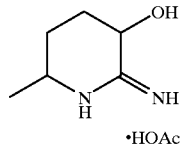

The method of preparation of 2-imino-4-methylpiperidine acetate was used to convert 3-hydroxy-6-methyl-2-nitropyridine to the title compound except the reaction was run at 55° C. Product was obtained as a dark solid which was recrystallized from EtOH/EtOAc to give light amber crystals. The analysis of the product was found to be consistent with the proposed structure. m.p. 158–160° C. MH+=129; $^1$H NMR (D$_2$O): δ4.40–4.30 (m, 1H); 3.60–3.40 (m, 1H); 2.00–1.40 (m, 4H); 1.72 (s, 3H); 1.10 (d, J=7 Hz, 3H).

Elemental analysis: C$_8$H$_{16}$N$_2$O$_3$.(0.15 H$_2$O )

|  | C | H | N |
|---|---|---|---|
| Calculated: | 50.33 | 8.61 | 14.67 |
| Found: | 50.33 | 8.54 | 14.66 |

EXAMPLE 278

3-ethoxy-2-imino-6-methylpiperidine hydrochloride

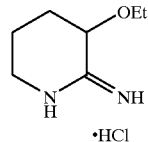

The method of preparation of 2-imino-4-methylpiperidine acetate was used to convert 3-ethoxy-2-nitropyridine to the title compound except the reaction was run at 55° C. Product was obtained as a dark oil which was purified by C-18-reverse phase chromatography, eluting with $H_2O/CH_3CN$. Fractions containing the product were lyophilized, redissolved in 1N HCl and lyophilized to give the product as a light yellow oil. The analysis of the product was found to be consistent with the proposed structure. MH+=143; $^1$H NMR ($D_2O$): δ4.35–4.20 (m, 1H); 3.8–3.5 (m, 2H); 3.30–3.10 (m, 2H); 2.25–2.10 (m, 1H); 2.0–1.5 (m, 3H); 1.07 (t, J=7 Hz, 3H).

EXAMPLE 279

2-imino-decahydroisoquinoline acetate

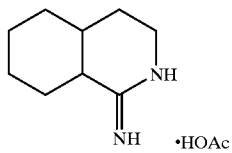

2-amino-isoquinoline (1 g), palladium black (0.5 g) and ammonium formate (1 g) were suspended in methanol (150 ml) with stirring. The reaction mixture was stirred over the weekend at 40° C. and the catalyst was removed by filtration. The filtrate was taken down to dryness and the residue was triturated with dried ether to give 3,4-benzo-2-iminopiperidine formate as a solid. ES-MS: MH+=147.

The method of preparation of 2-imino-4-methylpiperidine acetate was used to convert 3,4-benzo-2-iminopiperidine to the title compound except platinum oxide was used as the catalyst. The product was recrystallized from EtOAc/EtOH to give a light tan solid. The analysis of the product was found to be consistent with the proposed structure. MH+= 153; $^1$H NMR ($D_2O$): δ3.4–3.1 (m, 3H); 2.6–2.4 (m, 1H); 2.20–1.00 (m, 10H); 1.75 (s, 3H).

EXAMPLE 280

2-amino-5,6,7,8-tetrahydroisoquinoline acetate

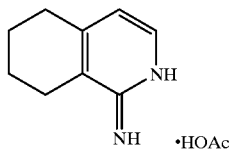

The method of preparation of 2-imino-4-methylpiperidine acetate was used to convert 2-aminoisoquinoline to the title compound except platinum oxide was used as the catalyst.

The product was triturated with EtOH to give a white solid. The analysis of the product was found to be consistent with the proposed structure. $^1$H NMR ($D_2O$): δ 7.35 (d, J=6 Hz, 1H); 6.55 (d, J=6 Hz, 1H); 2.6–2.5 (m, 2H); 2.20–2.10 (m, 2H); 1.75 (s, 3H); 1.70–1.50 (m, 4H).

Elemental analysis: $C_{11}H_{16}N_2O_2$

|  | C | H | N |
|---|---|---|---|
| Calculated: | 63.44 | 7.74 | 13.45 |
| Found: | 63.22 | 7.89 | 13.47 |

EXAMPLE 281

5-amino-2-iminopiperidine hydrochloride

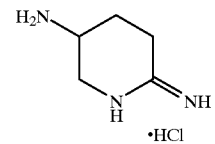

2,5-diaminopyridine dihydrochloride (1.2 g) and platinum oxide (500 mg) in ethanol (20 mL) and conc HCl (2 mL) were shaken on a Parr hydrogenation apparatus at 55 psi of hydrogen overnight. Product was obtained as a dark solid which was purified by C-18-reverse phase chromatography, eluting with $H_2O/CH_3CN$. Fractions containing the product were lyophilized, redissolved in 1N HCl and lyophilized to give the product as a yellow solid. The analysis of the product was found to be consistent with the proposed structure. MH+=114; $^1$H NMR ($D_2O$): δ3.8–3.6 (m, 2H); 3.4–3.25 (m, 1H); 2.75–2.65 (m, 2H); 2.25–2.15 (m, 1H); 2.15–1.85 (m, 1H).

Elemental analysis: $C_5H_{13}C_{12}N_3$

|  | C | H | N |
|---|---|---|---|
| Calculated: | 32.27 | 7.04 | 22.58 |
| Found: | 32.43 | 7.00 | 22.48 |

EXAMPLE 282

2-imino-4-piperidine carboxylic acid hydrochloride

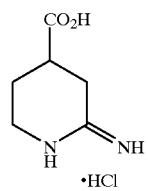

The method of preparation of 2-imino-4-methylpiperidine acetate was used to convert 2-aminopyridine-4-carboxylic acid to the title compound except platinum oxide was used as the catalyst. Product dissolved in 3N HCl and lyophilized to give white solid, which was recrystallized from EtOH to give product as a white solid. The analysis of the product was found to be consistent with the proposed structure. m.p.

230–234° C. ¹H NMR (D₂O): δ3.40–3.20 (m, 2H); 3.0–2.8 (m, 2H); 2.80–2.70 (m, 2H); 2.20–2.00 (m, 1H); 2.00–1.80 (m, 1H).

Elemental analysis: $C_6H_{11}ClN_2O_2$

|  | C | H | N |
|---|---|---|---|
| Calculated: | 40.35 | 6.21 | 15.68 |
| Found: | 40.43 | 6.20 | 15.29 |

EXAMPLE 283

5-amino-2-imino-4-methylpiperidine dihydrochloride (cis and trans isomers)

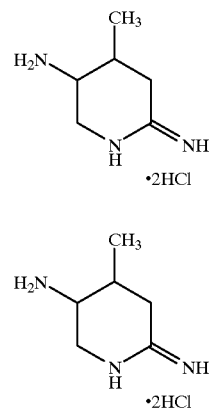

The method of preparation of 5-amino-2-iminopiperidine hydrochloride was used to convert 2-amino-4-methyl-5-nitropyridine to the title compound. Product was obtained as a white solid, shown to be two isomers by ¹H NMR analysis. Recrystallization from EtOH/H₂O gave a white solid, shown to be one isomer (A) by ¹H NMR and tentatively assigned the trans configuration. The mother liquor was concentrated in vacuo and redissolved in warm EtOH. Upon cooling, the first crop was obtained which contains more (A). The second crop contains a mixture of (A) and (B). The third crop is pure (B), which was tentatively assigned the cis configuration. The analysis of the product was found to be consistent with the proposed structure. ¹H NMR (D₂O) of (A): δ3.8–3.7 (m, 1H); 3.68–3.58 (m, 1H); 3.50–3.40 (m, 1H); 2.90–2.75 (m, 1H); 2.45–2.35 (m, 2H); 1.00 (d, J=7 Hz, 3H). ¹H NMR (D₂O) of (B): 3.75–3.65 (m, 1H); 3.45–3.25 (m, 2H); 2.85–2.70 (m, 1H); 2.50–2.35 (m, 1H); 2.20–2.15 (m, 1H); 1.05 (d, J=7 Hz, 3H).

Elemental analysis of (A): $C_6H_{15}Cl_2N_3.(H_2O)$

|  | C | H | N |
|---|---|---|---|
| Calculated: | 33.04 | 7.86 | 19.26 |
| Found: | 33.01 | 7.39 | 19.20 |

Elemental analysis of (B): $C_6H_{15}C_{12}N_3.(0.4\ H_2O)$

|  | C | H | N |
|---|---|---|---|
| Calculated: | 34.76 | 7.68 | 20.27 |
| Found: | 34.53 | 7.54 | 20.67 |

EXAMPLE 284

Ethyl(2'-imino)-2-(3'-piperidineoxy)acetate hydrochloride

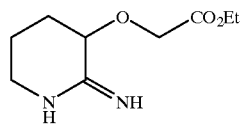

3-hydroxy-2-nitropyridine (5 g) and anhydrous potassium carbonate (5 g) were mixed in anhydrous DMF (75 mL) for 15 minutes. Ethyl bromoacetate was added and contents were stirred overnight. The contents were poured into ice water and extracted with EtOAc (2×200 mL). The EtOAc extracts were combined, dried (MgSO₄) and concentrated in vacuo to give 2'-nitro-2-(3'-pyridineoxy)acetate as a light yellow solid (6.6 g).

The method of preparation of 5-amino-2-iminopiperidine hydrochloride was used to convert 2'-nitro-2-(3'-pyridineoxy)acetate to the title compound. Purification by C-18-reverse phase chromatography and recrystallization from EtOH/EtOAc gave the product as a white solid.

The analysis of the product was found to be consistent with the proposed structure. MH+=201;

Elemental analysis: $C_9H_{17}ClN_2O_3.(0.25\ H_2O)$

|  | C | H | N |
|---|---|---|---|
| Calculated | 44.82 | 7.31 | 11.61 |
| Found: | 44.92 | 7.62 | 11.75 |

EXAMPLE 285

2-imino-5-(n-butyl)piperidine acetate

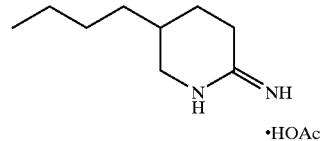

Fusaric acid (2 g), diphenylphosphoryl azide (2.4 mL) and triethylamine (1.6 mL) in t-butanol (70 mL) were refluxed overnight. The contents were concentrated in vacuo and treated with 25% aqueous HBr (20 mL) for 24 hours. After neutralizing with 50% NaOH, contents were extracted with CH₂Cl₂, dried (MgSO₄) and concentrated in vacuo to give 2-amino-5-(n-butyl)pyridine as an oil (1.1 g).

The method of preparation of 2-imino-4-methylpiperidine acetate was used to convert 2-amino-5-(n-butyl)pyridine to the title compound except platinum oxide was used as the catalyst. Product was triturated with ether to give a white solid. The analysis of the product was found to be consistent with the proposed structure. MH+=155; $^1$H NMR (D$_2$O): δ3.35–3.25 (m, 1H); 2.85–2.75 (m, 1H); 2.60–2.35 (m, 2H); 1.85–1.55 (m, 2H); 1.75 (s, 3H); 1.35–1.05 (m, 7H); 0.75–0.65 (m, 3H).

EXAMPLE 286

2-imino-5-(trifluoromethyl)piperidine hydrochloride

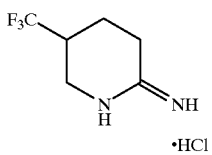

The method of preparation of 2-imino-4-methylpiperidine acetate was used to convert 2-amino-3-chloro-5-(trifluoromethyl)pyridine to the title compound except platinum oxide was used as the catalyst. Product was triterated with ether to give a white solid. The analysis of the product was found to be consistent with the proposed structure. MH+=167; $^1$H NMR (D$_2$O): δ3.65–3.50 (m, 1H); 3.40–3.20 (m, 1H); 2.85–2.45 (m, 3H); 2.15–2.00 (m, 1H); 1.80–1.60 (m, 1H).

Elemental analysis: C$_6$H$_{10}$ClF$_3$N$_2$.(0.1 H$_2$O)

|  | C | H | N |
|---|---|---|---|
| Calculated: | 35.26 | 5.03 | 13.70 |
| Found: | 34.91 | 4.97 | 13.64 |

EXAMPLE 287

O-[3-(2-iminopiperidinyl)]-4-amino-1-butanol

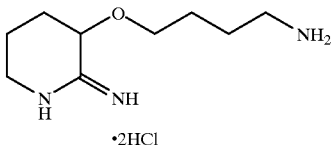

3-hydroxy-2-nitropyridine (5 g) and anhydrous potassium carbonate (5 g) were mixed in anhydrous DMF (75 mL) for 15 minutes. 4-Bromo-butyronitrile (3.6 mL) was added and contents were stirred overnight. Contents were poured into ice water and 4-[2'-nitro-(3'-pyridineoxy)]butyronitrile, as a white solid, was filtered.

The method of preparation of 2-imino-4-methylpiperidine acetate was used to convert 4-[2'-nitro-(3'-pyridineoxy)] butyronitrile to the title compound except platinum oxide was used as the catalyst. Purification by C-18 reverse phase chromatography and crystallization from EtOAc/EtOH gave the product as a white solid. The analysis of the product was found to be consistent with the proposed structure. MH+= 185; $^1$H NMR (D$_2$O): δ3.75–3.65 (m, 1H); 3.50–3.40 (m, 2H); 3.30–2.85 (m, 6H); 1.80–1.45 (m, 8H).

Elemental analysis: C$_9$H$_{21}$Cl$_2$N$_3$O

|  | C | H | N |
|---|---|---|---|
| Calculated | 41.87 | 8.20 | 16.28 |
| Found: | 41.83 | 8.33 | 15.98 |

EXAMPLE 288

4-amino-2-iminopiperidine dihydrobromide

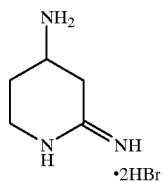

4-Amino-3,5,6-trichloropicolinic acid (1.0 g), diphenylphosphorylazide (1.0 mL) and triethylamine (0.6 mL) in t-butanol (35 mL) were refluxed overnight. Contents were concentrated in vacuo leaving a white solid, which was treated with 25% aqueous HBr (20 mL) for 24 hours. 2,4-diamino-3,5,6-trichloropyridine dihydrobromide was filtered as a light yellow solid (1.2 g).

2,4-Diamino-3,5,6-trichloropyridine dihydrobromide (1.1 g) and platinum oxide (520 mg) in ethanol (50 mL) were shaken on a Parr hydrogenation apparatus at 55 psi of hydrogen for 48 hours. The contents were filtered and the filtrate was concentrated in vacuo leaving a waxy solid. The solid was triturated with ether/EtOH to give 4-amino-2-iminopiperidine dihydrobromide as a white solid. The analysis of the product was found to be consistent with the proposed structure. MH+=114; $^1$H NMR (D$_2$O): δ3.80–3.60 (m, 1H); 3.55–3.25 (m, 1H); 3.08–2.95 (m, 1H); 2.76–2.62 (m, 1H); 2.25–2.13 (m, 1H); 1.95–1.80 (m, 1H).

EXAMPLE 289

5-aminomethyl-2-imino-4,6-dimethylpiperidine dihydrochloride

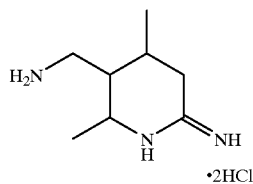

The method of preparation of 2-imino-4-methylpiperidine acetate was used to convert 2-amino-5-cyano-4,6-dimethylpyridine to the title compound except platinum oxide was used as the catalyst. Product was treated with EtOH to give a white solid. The analysis of the product was found to be consistent with the proposed structure. MH+= 156; $^1$H NMR (D$_2$O): δ3.63–3.40 (m, 2H); 3.20–3.05 (m, 1H); 2.70–2.58 (m, 1H); 2.40–2.20 (m, 1H); 2.05–1.80 (m, 2H); 1.22 (d, J=7 Hz, 3H); 0.95 (d,J=7 Hz, 3H).

EXAMPLE 290

2-imino-6-methyl-4-(trifluoromethyl)piperidine hydrochloride

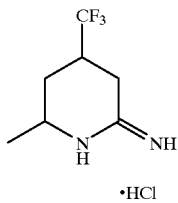

•HCl 2-chloro-6-methyl-4-(trifluoromethyl)pyridine (5.0 g) and conc ammonium hydroxide (150 mL) were heated at 180° C. in a steel reaction vessel with mechanical stirring overnight. The contents were allowed to cool and partitioned between $CH_2Cl_2$ and water. The $CH_2Cl_2$ layer was dried ($MgSO_4$) and concentrated in vacuo leaving 2-amino-6-methyl-4-(trifluoromethyl)pyridine as a white solid.

The method of preparation of 2-imino-4-methylpiperidine acetate was used to convert 2-amino-6-methyl-4-(trifluoromethyl)pyridine to the title compound. Product was triturated with EtOAc/EtOH to give a white solid. The analysis of the product was found to be consistent with the proposed structure. MH+=181; $^1$H NMR ($D_2O$): δ3.60–3.40 (m, 1H); 2.80–2.50 (m, 3H); 2.20–2.05 (m, 1H); 1.42–1.25 (m, 1H); 1.15 (d, J=7 Hz, 3H).

Elemental analysis: $C_7H_{12}ClF_3N_2 \cdot (0.25\ H_2O)$

|  | C | H | N |
|---|---|---|---|
| Calculated | 38.02 | 5.70 | 12.67 |
| Found: | 37.98 | 5.54 | 12.84 |

EXAMPLE 291

2-imino-4-(trifluoromethyl)piperidine hydrochloride

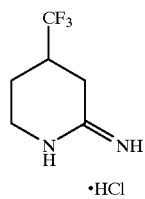

•HCl

The method of preparation of 2-amino-6-methyl-4-(trifluoromethyl)pyridine was used to convert 2-chloro-4-(trifluoromethyl)pyridine to 2-amino-4-(trifluoromethyl)pyridine.

The method of preparation of 2-imino-4-methylpiperidine acetate was used to convert 2-amino-4-(trifluoromethyl)pyridine to the title compound. The product was triturated with EtOAc to give a white solid. The analysis of the product was found to be consistent with the proposed structure. MH+=167; $^1$H NMR ($D_2O$): δ3.45–3.35 (m, 1H); 3.30–3.20 (m, 1H); 2.85–2.55 (m, 3H); 2.10–2.00 (m, 1H); 1.80–1.60 (m, 1H).

Elemental analysis: $C_6H_{10}ClF_3N_2$

|  | C | H | N |
|---|---|---|---|
| Calculated: | 35.57 | 4.98 | 13.83 |
| Found: | 35.17 | 4.76 | 13.70 |

EXAMPLE 292

2-imino-3-(trifluoromethyl)piperidine trifluoroacetate

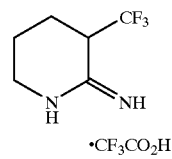

•$CF_3CO_2H$

The method of preparation of 2-amino-6-methyl-4-(trifluoromethyl)pyridine was used to convert 2-chloro-3-(trifluoromethyl)pyridine to 2-amino-3-(trifluoromethyl)pyridine.

The method of preparation of 2-imino-4-methylpiperidine acetate was used to convert 2-amino-3-(trifluoromethyl)pyridine to the title compound. Product was crystallized from EtOAc/hexanes to give a white solid. The analysis of the product was found to be consistent with the proposed structure. MH+=167; $^1$H NMR ($D_2O$): δ3.70–3.50 (m, 1H); 3.35–3.20 (m, 2H); 2.10–1.60 (m, 4H).

Elemental analysis: $C_8H_{10}F_6N_2O_2$

|  | C | H | N |
|---|---|---|---|
| Calculated: | 34.30 | 3.60 | 10.00 |
| Found: | 34.55 | 3.65 | 10.01 |

EXAMPLE 293

2-imino-6-(trifluoromethyl)piperidine acetate

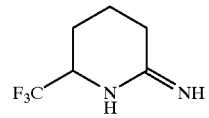

The method of preparation of 2-amino-6-methyl-4-(trifluoromethyl)pyridine was used to convert 2-chloro-6-(trifluoromethyl)pyridine to 2-amino-6-(trifluoromethyl)pyridine.

The method of preparation of 2-imino-4-methylpiperidine acetate was used to convert 2-amino-6-(trifluoromethyl)pyridine to the title compound. Product was crystallized from EtOAc to give a white solid. The analysis of the product was found to be consistent with the proposed structure. MH+=167; $^1$H NMR ($D_2O$): δ4.20–4.00 (m, 1H); 2.60–2.50 (m, 2H); 2.05–1.50 (m, 4H); 1.80 (s, 3H).

EXAMPLE 294

2-imino-4-(n-propyl)piperidine acetate

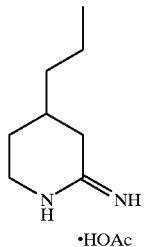

·HOAc

The method of preparation of 2-imino-4-methylpiperidine acetate was used to convert 2-amino-4-(n-propyl)pyridine to the title compound except platinum oxide was used as the catalyst. Product was triturated with EtOAc to give a white solid. The analysis of the product was found to be consistent with the proposed structure. MH+=141; $^1$H NMR (D$_2$O): δ3.35–3.05 (m, 2H); 2.60–2.40 (m, 1H); 2.15–2.00 (m, 1H); 1.80–1.60 (m, 2H); 1.78 (s, 3H); 1.35–1.05 (m, 5H); 0.75–0.65 (m, 3H).

EXAMPLE 295

2-imino-4-(n-ethyl)piperidine acetate

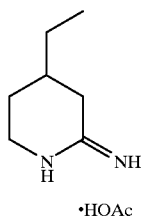

·HOAc

The method of preparation of 2-imino-4-methylpiperidine acetate was used to convert 2-amino-4-(n-ethyl)pyridine to the title compound except platinum oxide was used as the catalyst. The product was crystallized from cold EtOAc to give a white solid. The analysis of the product was found to be consistent with the proposed structure. MH+=127; $^1$H NMR (D$_2$O): δ3.40–325 (m, 1H); 3.22–3.10 (m, 1H); 2.60–2.50 (m, 1H); 2.15–2.00 (m, 1H); 1.85–1.75 (m, 1H); 1.78 (s, 3H); 1.70–1.60 (m, 1H); 1.35–1.15 (m, 3H); 0.75 (t, J=7 Hz, 3H)

EXAMPLE 296

2-Iminododecamethylenimine Hydrochloride salt

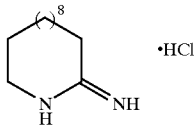

To a solution of 1 g (0.0067 mol) of trimethyloxonium tetrafluoroborate in 10 mL of anhydrous chloroform was added 1.33 g (0.0067 mol) of 2-azacyclotridecanone. This mixture was stirred at reflux for four hours, then for 18 hours at 25° C. This mixture was then diluted with ethyl acetate, washed with dilute potassium carbonate, dried (MgSO$_4$), filtered and concentrated to afford 1.3 g of a pink oil. This oil was dissolved in 25 mL of methanol and 0.33 g (0.006 mol) of ammonium chloride was added. After stirring at 25° C. for 72 hours, the mixture was concentrated to afford 0.6 g of a white solid. It was extracted with water, filtered and the filter was lyophilized to afford 2-iminododecamethylenimine hydrochloride salt as a white fluffy solid. $^1$H-NMR(D$_2$O) 1.1–1.3 (m, 14H), 1.45–1.65 (m, 4H), 2.35 (m, 2H), 3.2 (m, 2H); Mass Spectra, M+H=197; Elemental analysis Calcd. for C$_{12}$H$_{25}$N$_2$Cl$_1$+2/3 N$_1$H$_4$Cl$_1$: C, 53.65; H, 10.39; N,13.92. Found C, 53.42, H, 10.32, N, 13.58.

EXAMPLE 297

2-Imino-6-Cyclopentylpiperidine Trifluoroacetic acid salt

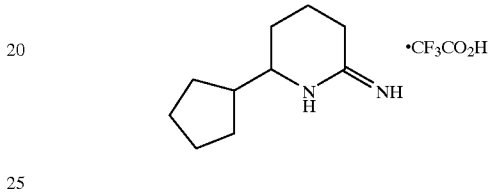

·CF$_3$CO$_2$H

To a solution of 1 g (0.0067 mol) of trimethyloxonium tetrafluoroborate in 20 mL of anhydrous chloroform was added 0.5 g (0.003 mol) of 6-cyclopentylvalerolactam. This mixture was stirred at reflux for three hours. This mixture was allowed to cool to 25° C., washed with dilute sodium bicarbonate, dried (MgSO$_4$), filtered and concentrated to afford a yellow oil. This oil was dissolved in 25 mL of methanol and 0.16 g of ammonium chloride was added. After stirring at 25° C. for 18 hours, the mixture was concentrated to afford a white semisolid. Chromatography (C-18) afforded the pure 2-imino-6-cyclopentylpiperidine trifluoroacetic acid salt as a white solid. $^1$H-NMR(D$_2$O) 1.05–1.2 (m, 2H), 1.35–1.95 (m, 11H), 2.3–2.55 (m, 2H), 3.15–3.25 (m, 1H); Mass Spectra, M+H=167.

EXAMPLE 298

(2-Ethylimino)-4-methylpiperidine acetate

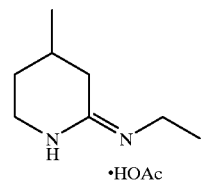

·HOAc

Hydrobromic acid (48%, 39.5 mL) was cooled to 0° C. and 2-amino-4-picoline (Aldrich, 8.6 g, 0.08 mole) was added in portions. At 0° C., bromine (12 mL, 0.234 mole) was added slowly dropwise, followed by dropwise addition of a solution of sodium nitrite (14.0 g) in water (20 mL) at 0° C. The contents were stirred 1½ hours at 0° C. before adding 50% aqueous sodium hydroxide (60 g), keeping the temperature less than 20° C. during the addition. Contents were stirred 1 hour and extracted with ether (2×200 mL). The ether layers were combined and dried over potassium hydroxide pellets for 1 hour, filtered and concentrated in vacuo leaving an orange oil (12.4 g). The oil was distilled on a kugelrohr apparatus at 40° C. (0.25 mm) to give 2-bromo-4-methylpyridine as a yellow oil (10.3 g).

2-Bromo-4-methylpyridine (1.5 g, 0.02 mole) and aqueous ethylamine (70%, 100 mL) were heated at 150° C. overnight in a steel pressure reactor. Contents were allowed to cool and concentrated in vacuo. The residue was triturated with $CH_2Cl_2$ and a white solid was filtered and discarded. The filtrate was concentrated in vacuo leaving an oil (950 mg). The oil was distilled on a kugelrohr apparatus at 90° C. (0.35 mm) to give 2-(ethylamino)-4-methylpyridine as a white solid (670 mg).

The method of preparation of 2-imino-4-methylpiperidine acetate was used to convert 2-(ethylamino)-4-methylpyridine to the title compound except platinum oxide was used as the catalyst. The analysis of the product, obtained as an oil, was found to be consistent with the proposed structure. MH+=141; $^1$H NMR ($D_2O$): δ3.40–3.10 (m, 2H); 3.00 (q, J=6 Hz, 2H); 2.50–2.40 (m, 1H); 2.10–1.90 (m, 1H); 1.83 (s, 3H); 1.80–1.65 (m, 4H); 1.40–1.20 (m, 1H); 1.02 (t, J=6 Hz, 3H); 0.83 (d, J=6 Hz, 3H).

EXAMPLE 299

2-(N,N-dimethylamino)-4-methyl-3,4,5,6-tetrahydropyridine hydrochloride

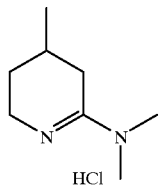

The method of preparation of 2-(ethylamino)-4-methylpyridine was used to convert 2-bromo-4-methylpyridine to 2-(N,N-dimethylamino)-4-methylpyridine.

The method of preparation of 2-imino-4-methylpiperidine acetate was used to convert 2-(N,N-dimethylamino)-4-methylpyridine to the title compound except platinum oxide was used as the catalyst. The product was obtained as a clear colorless oil which was dissolved in 3N HCl and lyophilized to give the desired product as a waxy colorless solid. The analysis of the product was found to be consistent with the proposed structure. MH+=141; $^1$H NMR ($D_2O$): 3.44–3.32 (m, 1H); 3.28–3.16 (m, 1H); 3.00 (s, 3H); 2.90 (s, 3H); 2.76–2.64 (m, 1H); 2.08–1.94 (m, 1H); 1.88–1.68 (m, 2H); 1.35–1.18 (m, 1H); 0.52 (d, J=6 Hz, 3H).

EXAMPLE 300

2'-(2-aminoethylimino)-5'-(trifluoromethyl) piperidine dihydrochloride

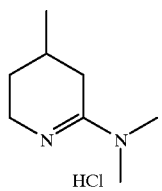

The method of preparation of 2-imino-4-methylpiperidine acetate was used to convert 2'-(2-aminoethylamino)-3'-chloro-5'-(trifluoromethyl)pyridine to the title compound. The analysis of the product, obtained as an oil, was found to be consistent with the proposed structure. MH+=210; $^1$H NMR (D2O): 3.70–3.35 (m, 4H); 3.18 (t, J=6 Hz, 2H); 2.95–2.60 (m, 3H); 2.20–2.00 (m, 1H); 1.90–1.70 (m, 1H).

EXAMPLE 301

6-Benzyl-2-iminopiperidine hydrochloride

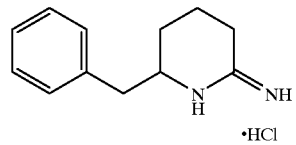

2-benzylpyridine (Aldrich, 2.5 g, 0.015 mole), sodium amide (780 mg, 0.02 mole) and N,N-dimethylaniline (25 mL) were refluxed overnight. The contents were allowed to cool and were partitioned between ether and water. The ether layer was dried ($MgSO_4$) and concentrated in vacuo leaving an oil. The oil was purified by chromatography. The purified material was dissolved in 1N HCl, lyophilized, and triturated with EtOAc to give 2-amino-6-benzylpyridine as a white solid.

The method of preparation of 2-imino-4-methylpiperidine acetate was used to convert 2-amino-6-benzylpyridine to the title compound. The product was obtained as an oil which was purified by C-18 reverse phase chromatography to give a white solid. The solid was dissolved in 1 N HCl, lyophilized, and recrystallized from EtOH/EtOAc to give the desired product as a white solid. The analysis of the product was found to be consistent with the proposed structure. MH+=189; $^1$H NMR ($CDCl_3$): 9.85 (s, 1H); 8.95 (s, 1H); 8.62 (s, 1H); 7.40–7.10 (m, 5H); 3.80–3.60 (m, 1H); 3.20–3.00 (m, 1H); 2.90–2.70 (m, 2H); 2.65–2.45 (m, 1H); 2.42–2.25 (m, 2H); 1.92 (m, 2H); 1.75 (m, 1H); 1.50–1.35 (m, 1H).

EXAMPLE 302

2-(cyclohexylmethyl)-6-iminopiperidine hydrochloride

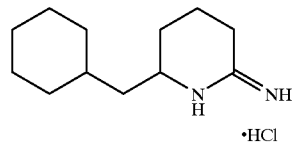

The method of preparation of 2-imino-4-methylpiperidine acetate was used to convert 2-amino-6-benzylpyridine to the title compound except platinum oxide was used as the catalyst. The product was obtained as an oil which was dissolved in 1 N HCl and lyophilized to give a white solid. The solid was recrystallized from EtOAc to give the desired product as white crystals. The analysis of the product was found to be consistent with the proposed structure. MH+= 195; $^1$H NMR ($CDCl_3$): 9.60 (s, 1H); 8.90 (s, 1H); 8.70 (s, 1H); 3.60–3.40 (m, 1H); 2.90–2.70 (m, 1H); 2.70–2.50 (m, 1H); 2.10–1.80 (m, 2H); 1.80–1.00 (m, 13H); 1.00–0.80 (m, 2H).

EXAMPLE 303

2-cyclohexyl-6-iminopiperidine hydrochloride

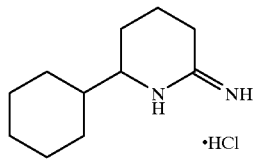

The method of preparation of 2-amino-6-benzylpyridine was used to convert 2-phenylpyridine (Aldrich) to 2-amino-6-phenylpyridine.

The method of preparation of 2-imino-4-methylpiperidine acetate was used to convert 2-amino-6-phenylpyridine to the title compound except the reaction was run at 55° C. The product was obtained as an oil which was crystallized from EtOH/EtOAc to give the desired product as a white solid.

MH+=181; $^1$H NMR (CDCl$_3$): 3.30–3.15 (m, 1H); 2.50–2.30 (m, 2H); 1.85–1.68 (m, 2H); 1.65–1.20 (m, 8H); 1.20–0.80 (m, 5H).

EXAMPLE 304

4-Methylpiperidine-2-hydrazone acetate

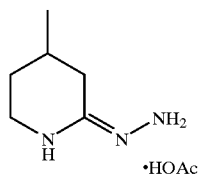

The method of preparation of 2-imino-4-methylpiperidine acetate was used to convert 2-hydrazinopyridine (Aldrich) to the title compound except the reaction was run in glacial acetic acid/water (2:1) for solubility and platinum oxide was used for the catalyst. The product was obtained as a clear colorless oil which crystallized under EtOAc and was recrystallized from ethanol to give the desired as white crystals. The analysis of the product was found to be consistent with the proposed structure. MH+=114; $^1$H NMR (D$_2$O): 3.15–3.10 (m, 2H); 2.60–2.50 (m, 2H); 1.98 (s, 3H); 1.80–1.60 (m, 4H).

EXAMPLE 305

4-Methyl-2-(propylimino)piperidine hydrochloride

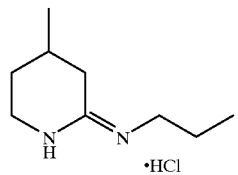

The method of preparation of 2-(ethylimino)-4-methylpiperidine acetate was used to convert 4-methyl-2-(propylamino)pyridine hydrochloride to the title compound. The product was obtained as a clear colorless oil which crystallized under EtOAc. The analysis of the product was found to be consistent with the proposed structure. MH+=155; $^1$H NMR (D$_2$O): 3.45–3.20 (m, 2H); 3.05 (t, J=6 Hz, 2H); 2.60–2.45 (m, 1H); 2.20–2.00 (m, 1.95–1.70 (m, 2H); 1.60–1.40 (m, 2H); 1.40–1.25 (m, 1H); 0.90 (d, J=6 Hz, 3H); 0.80 (t, J=6 Hz, 3H).

EXAMPLE 306

2-Iminohexamethylenimine Hydroiodide salt J. Med. Chem. 21(10), 1044–54 (1978)

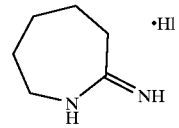

To a solution of 5 g (0.039 mol) of thiocaprolactam in 100 mL of acetone was added 6.4 g (0.045 mol) of iodomethane. This mixture was stirred two days at 25° C. Filtration afforded 9.5 g of the thio-iminoether hydroiodide salt as a white solid, mp 177–181° C. Three grams of this iminoether was dissolved in 80 mL of ethanol saturated with anhydrous ammonia. This mixture was sealed and stirred at 25° C. for three days. Concentration to a reduced volume followed by ether trituration afforded 2.2 g of the title product as a white solid, mp 135–141° C. $^1$H-NMR(D$_2$O) 1.45–1.55 (m, 2H), 1.55–1.7 (m, 4H), 2.5 (m, 2H), 3.28 (m, 2H); Mass Spectra, M+H=113; Elemental analysis Calcd. for C$_6$H$_{13}$N$_2$I$_1$: C, 30.02; H, 5.46; N, 11.67. Found C, 29.99, H, 5.49, N, 11.61.

EXAMPLE 307

2-(Methylimino)hexaethylenimine Hydroiodide salt

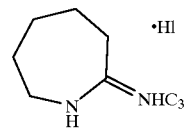

To a solution of 1 g (0.0037 mol) of the thio-iminoether from EXAMPLE 306 was added 40 mL of ethanol saturated with anhydrous methylamine. This mixture was sealed and stirred at 25° C. for three days. Concentration to a reduced volume followed by ether trituration afforded 0.9 g of the title product as a white solid, mp 169–171° C. $^1$H-NMR (D$_2$O) 1.45–1.65 (m, 6H), 2.48 (m, 2H), 2.68 (s, 3H), 3.3 (m, 2H); Mass Spectra, M+H=127; Elemental analysis Calcd. for C$_7$H$_{15}$N$_2$I$_1$: C, 33.09; H, 5.95; N, 11.02. Found C, 33.31, H, 5.94, N, 10.97.

EXAMPLE 308

1-Methyl-2-iminopentamethylenimine Hydroiodide salt

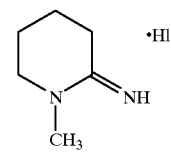

To a solution of 2 g (0.0155 mol) of N-methylthiovalerolactam in 40 mL of acetone was added 2.4 g (0.017 mol) of iodomethane. This mixture was stirred three days at 25° C. Filtration and trituration with ether afforded 4 g of the thio-iminoether hydroiodide salt as a white solid, mp 153–155° C. One gram of this iminoether was dissolved in 50 mL of ethanol saturated with anhydrous ammonia. This mixture was sealed and stirred at 25° C. for eighteen hours. Concentration to a reduced volume followed by ether trituration afforded 0.8 g of the title product as a white solid, mp 157–158° C. $^1$H-NMR(D2O) 1.6–1.7 (m, 2H), 1.7–1.8 (m, 2H), 2.5 (t, 2H), 2.95 (s, 3H), 3.38 (t, 2H); Mass Spectra, M+H=113; Elemental analysis Calcd. for $C_6H_{13}N_2I_1$: C, 30.02; H, 5.46; N, 11.67. Found C, 30.16, H, 5.49, N, 11.63.

EXAMPLE 309

1-Methyl-2-iminohexamethylenimine Hydroiodide salt

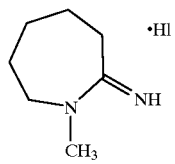

To a solution of 2 g (0.014 mol) of N-methylthiocaprolactam in 40 mL of acetone was added 2.18 g (0.0154 mol) of iodomethane. This mixture was stirred three days at 25° C.

Filtration and trituration with ether afforded 3.8 g of the thio-iminoether hydroiodide salt as a white solid, mp 138–142° C. One gram of this iminoether was dissolved in 50 mL of ethanol saturated with anhydrous ammonia. This mixture was sealed and stirred at 25° C. for eighteen hours. Concentration to a reduced volume followed by ether trituration afforded 0.8 g of the title product as a white solid, mp 137–139° C. $^1$H-NMR(D$_2$O) 1.55–1.7 (m, 6H), 2.58 (m, 2H), 3.02 (s, 3H), 3.55 (m, 2H); Mass Spectra, M+H=127; Elemental analysis Calcd. for C7H15N2I1: C, 33.09; H, 5.95; N, 11.02. Found C, 33.12, H, 6.01, N, 11.07.

EXAMPLE 310

2-(Trifluoroethylimino)pentamethylenimine Hydroiodide salt

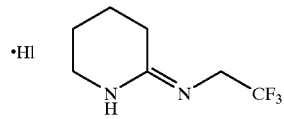

A mixture of 100 g (0.23 mol) of $P_4S_{10}$ and 24 g (0.23 mol) of $Na_2CO_3$ in 1.5 L of anhydrous THF was stirred vigorously with a mechanical stirrer for thirty minutes. To this stirred mixture was added 19 g (0.19 mol) of valerolactam. After stirring for three hours, the solution was diluted with 1 L of 10% aqueous $Na_3PO_4$, 750 mL of ethyl acetate and 750 mL of hexanes. Organic layer was separated and the aqueous layer was extracted with 500 mL of ethyl acetate. The organic extracts were combined, dried (MgSO$_4$), filtered through silica gel and concentrated to afford a white semi-solid. Trituration with hexanes-ether afforded 9.7 g of thiovalerolactam as a white solid, mp 85–88° C. To a solution of 9 g (0.078 mol) of thiovalerolactam in 100 mL of acetone was added 11.8 g (0.083 mol) of iodomethane. This mixture was stirred for eighteen hours at 25° C.

Filtration and ether trituration afforded 18.5 g of the thio-iminoether hydroiodide salt as a white solid. To a solution of 0.2 g (0.00077 mol) of the thio-iminoether in 3 mL of ethanol was added 0.2 g (0.002 mol) of trifluoroethylamine. This mixture was sealed and stirred at 25° C. for eighteen hours. Evaporation of the solvent afforded the title product as a white solid. $^1$H-NMR(D$_2$O) 1.65–1.7 (m, 4H), 2.58 (m, 2H), 3.32 (m, 2H), 3.95 (q, 2H); Mass Spectra, M+H=181.

EXAMPLE 311

2-(Cyclohexylimino)pentamethylenimine Hydroiodide salt

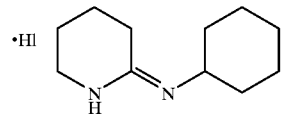

To a solution of 0.2 g (0.00077 mol) of the thio-iminoether from example RKW-E in 3 mL of ethanol was added 0.08 g (0.0008 mol) of cyclohexylamine. This mixture was sealed and stirred at 25° C. for eighteen hours. Evaporation of the solvent afforded the title product as a white solid. $^1$H-NMR(D$_2$O) 1.1–1.3 (m, 6H), 1.45–1.9 (m, 10H), 2.42 (t, 2H), 3.25 (t, 3H), 3.95 (q, 2H); Mass Spectra, M+H=181.

EXAMPLE 312

2-(Dimethylaminopropylimino)pentamethylenimine Hydroiodide salt

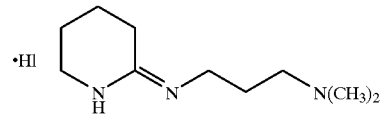

To a solution of 0.2 g (0.00077 mol) of the thio-iminoether from example RKW-E in 3 mL of ethanol was added 0.08 g (0.0008 mol) of N,N-dimethylaminopropylamine. This mixture was sealed and stirred at 25° C. for eighteen hours. Evaporation of the solvent afforded the title product as a white solid. $^1$H-NMR (D$_2$O) 1.6–1.75 (m, 6H), 2.1 (s, 6H), 2.3 (dd, 2H), 2.48 (t, 2H), 3.1 (t, 2H), 3.28 (t, 2H); Mass Spectra, M+H=184.

EXAMPLE 313

2-(Methylimino)pentamethylenimine Hydroiodide salt

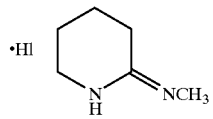

To a solution of 0.2 g (0.00077 mol) of the thio-iminoether from example RKW-E in 3 mL of ethanol was added 2 mL of ethanol saturated with anhydrous methylamine. This mixture was sealed and stirred at 25° C. for eighteen hours. Evaporation of the solvent afforded the title product as a white solid. $^1$H-NMR(D$_2$O) 1.6–1.7 (m, 4H), 2.45 (t, 2H), 2.7 (s, 3H) 3.3 (t, 2H); Mass Spectra, M+H= 113.

EXAMPLE 314

2-(Benzylimino)pentamethylenimine Hydroiodide salt

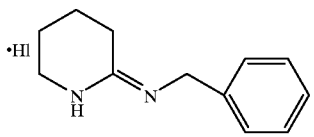

To a solution of 0.2 g (0.00077 mol) of the thio-iminoether from example RKW-E in 3 mL of ethanol was added 0.08 g (0.0008 mol) of benzylamine. This mixture was sealed and stirred at 25° C. for eighteen hours. Evaporation of the solvent afforded the title product as a white solid. Mass Spectra, M+H=189.

EXAMPLE 315

2-(Phenethylaminopropylimino)pentamethylenimine Hydroiodide salt

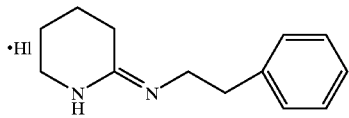

To a solution of 0.2 g (0.00077 mol) of the thio-iminoether from example RKW-E in 3 mL of ethanol was added 0.09 g (0.0008 mol) of phenethylamine. This mixture was sealed and stirred at 25° C. for eighteen hours. Evaporation of the solvent afforded the title product as a white solid. $^1$H-NMR(D$_2$O) 1.6 (m, 4H), 2.4 (m, 2H), 2.8 (t, 2H), 3.1 (m, 2H), 3.4 (t, 2H), 7.18–7.3 (m, 5H); Mass Spectra, M+H=203.

EXAMPLE 316

2-(p-Methoxyphenethylimino)pentamethylenimine Hydroiodide salt

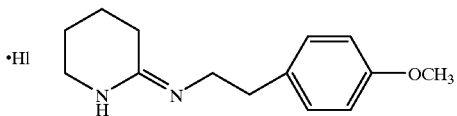

To a solution of 0.2 g (0.00077 mol) of the thio-iminoether from example RKW-E in 3 mL of ethanol was added 0.12 g (0.0008 mol) of p-methoxyphenethylamine. This mixture was sealed and stirred at 25° C. for eighteen hours. Evaporation of the solvent afforded the title product as a white solid. $^1$H-NMR(D$_2$O) 1.6 (m, 4H), 2.18 (m, 2H), 2.75 (t, 2H), 3.05 (m, 2H), 3.25 (t, 2H), 3.7 (s, 3H), 6.85 (d, 2H), 7.1 (d, 2H); Mass Spectra, M+H=233.

EXAMPLE 317

2-(3-hydroxypropylimino)pentamethylenimine Hydroiodide salt

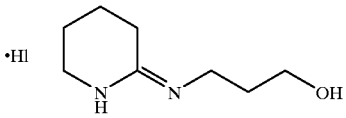

To a solution of 0.2 g (0.00077 mol) of the thio-iminoether from example RKW-E in 3 mL of ethanol was added 0.06 g (0.0008 mol) of 3-hydroxypropylamine. This mixture was sealed and stirred at 25° C. for eighteen hours. Evaporation of the solvent afforded the title product as a white solid. $^1$H-NMR(D$_2$O) 1.6–1.8 (m, 6H), 2.45 (t, 2H), 3.15 (t, 2H), 3.28 (t, 2H), 3.55 (t, 2H)); Mass Spectra, M+H=157.

EXAMPLE 318

(5:3) 2-Imino-6-hexyl-pentamethylenimine Hydrochloride salt:
2-Imino-3-hexyl-pentamethylenimine Hydrochloride salt

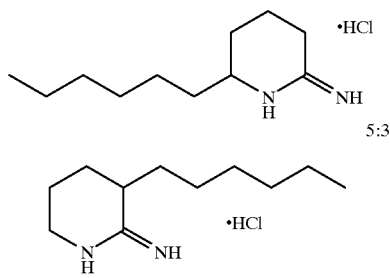

To a solution of 10 g (0.06 mol) of 2-hexylcyclopentanone in 80 mL of ethanol and 60 mL of water was added 6.3 g (0.09 mol) of hydroxylamine hydrochloride and 9 g (0.11 mol) of sodium acetate. This mixture was stirred for four hours at reflux, then for eighteen hours at 25° C. The reaction mixture was concentrated to a reduced volume, diluted with ethyl acetate, washed with three 200 mL portions of aqueous NaCl, dried (MgSO$_4$) filtered and concentrated to afford 10.2 g of the 2-hexylcyclopentanoneoxime as a colorless oil. A solution of 8 g (0.044 mol) of the oxime in 50 mL of acetone was treated with 48.4 mL (0.0484 mol) of 1N NaOH at 0° C. To this stirred mixture was added 8.1 g (0.046 mol) of benzenesulfonyl chloride dropwise. The resulting mixture was stirred for eighteen hours at 25° C. The reaction mixture was poured into water and extracted with ethyl acetate. The organic layer was separated, washed with aqueous NaCl, dried (MgSO$_4$), filtered and concentrated to afford 8 g of a yellow oil. Chromatography (C-18, 10% acetonitrile/water to 70% acetonitrile/water) on 2 g of the yellow oil afforded 1.5 g of a 2:1 ratio of the 6-hexylvalerolactam to the 3-hexylvalerolactam. To a solution of 1.5 g (0.01 mol) of trimethyloxonium tetrafluoroborate in 35 mL of methylene chloride was added 1.5 g (0.0082 mol) of the above valerolactam mixture. This mixture was stirred for 18 hours at 25° C. The reaction mixture was then diluted with ethyl acetate, washed with dilute potassium carbonate, dried (MgSO$_4$), filtered through a patty of silica gel and concentrated to afford 0.6 g of the iminoether as a yellow oil. This oil was dissolved in 40 mL of methanol and 0.18 g (0.0034 mol) of ammonium chloride was added. After stirring at reflux for 4 hours the mixture was stirred at 25° C. for 18 hours. The reaction mixture was then concentrated to remove solvents. The residue was dissolved in water and extracted with ethyl acetate. The aqueous layer was lyophilized to afford 0.16 g of a 5:3 mixture of 2-Imino-6-hexyl-pentamethylenimine Hydrochloride salt to 2-Imino-3-hexyl-pentamethylenimine Hydrochloride salt as a white solid. $^1$H-NMR(D$_2$O) 0.72 (t, 3H), 1.1–1.9 (m, 14H), 2.3–2.62 (m, 2H), 3.2 (t, 3-isomer), 3.38 (p, 6-isomer); Mass Spectra, M+H=183; Elemental analysis Calcd. for $C_{11}H_{23}N_2Cl_1$+3 $N_1H_4Cl_1$+3/4 $H_2O$: C, 33.64; H, 9.34; N, 17.83. Found C, 33.82, H, 9.20, N, 17.97.

EXAMPLE 319

(3:1) 2-Imino-6-heptyl-pentamethylenimine Hydrochloride salt:
2-Imino-3-heptyl-pentamethylenimine Hydrochloride salt

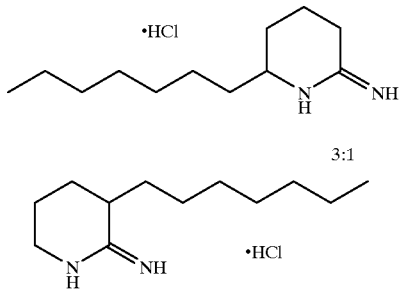

To a solution of 10 g (0.055 mol) of 2-heptylcyclopentanone in 75 mL of ethanol and 50 mL of water was added 5.8 g (0.083 mol) of hydroxylamine hydrochloride and 8.2 g (0.1 mol) of sodium acetate. This mixture was stirred for four hours at reflux, then for eighteen hours at 25° C. The reaction mixture was concentrated to a reduced volume, diluted with ethyl acetate, washed with three 200 mL portions of aqueous NaCl, dried (MgSO4) filtered and concentrated to afford 10 g of the 2-heptylcyclopentanoneoxime as a colorless oil. A solution of 8 g (0.04 mol) the oxime in 50 mL of acetone was treated with 44 mL (0.044 mol) of 1N NaOH at 0° C. To this stirred mixture was added 7.4 g (0.042 mol) of benzenesulfonyl chloride dropwise. The resulting mixture was stirred for eighteen hours at 25° C. The reaction mixture was poured into water and extracted with ethyl acetate. The organic layer was separated, washed with aqueous NaCl, dried (MgSO$_4$), filtered and concentrated to afford 8 g of a yellow oil. Chromatography (C-18, 10% acetonitrile/water to 70% acetonitrile/water) on 2 g of the yellow oil, afforded 1.1 g of a mixture of the 6-heptylvalerolactam to the 3-heptylvalerolactam. To a solution of 1 g (0.007 mol) of trimethyloxonium tetrafluoroborate in 25 mL of methylene chloride was added 1.1 g (0.0056 mol) of the above valerolactam mixture. This mixture was stirred for 18 hours at 25° C. The reaction mixture was then diluted with ethyl acetate, washed with dilute potassium carbonate, dried (MgSO$_4$), filtered through a patty of silica gel and concentrated to afford 0.6 g of the iminoether as a yellow oil. This oil was dissolved in 40 mL of methanol and 0.17 g (0.0032 mol) of ammonium chloride was added. After stirring at reflux for 4 hours the mixture was stirred at 25° C. for 18 hours. The reaction mixture was then concentrated to remove solvents. The residue was dissolved in water and extracted with ethyl acetate. The aqueous layer was lyophilized to afford 0.31 g of a 3:1 mixture of 2-Imino-6-heptyl-pentamethylenimine Hydrochloride salt to 2-Imino-3-heptyl-pentamethylenimine Hydrochloride salt as a white solid. $^1$H-NMR(D2O) 0.7 (t, 3H), 1.05–1.9 (m, 16H), 2.3–2.6 (m, 2H), 3.2 (t, 3-isomer), 3.35 (p, 6-isomer); Mass Spectra, M+H=197; Elemental analysis Calcd. for $C_{12}H_{25}N_2Cl_1$+0.6 $N_1H_4Cl_1$+1/3 $H_2O$: C, 53.22; H, 10.44; N,13.45. Found C,53.29, H, 10.53, N, 13.26.

EXAMPLE MVT-A

2-Imino-4-methyl-6-butyl-pentamethylenimine Trifluoroacetic acid salt

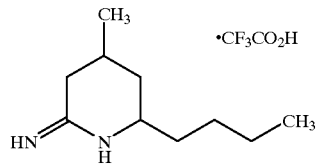

The title compound was prepared as in Example 319 from 3.4 g of 2-butyl-4-methylcyclopentanone. A final purification by C-18 HPLC (0–40% acetonitrile/H2O, 30 min.) afforded 0.2 g of the title compound as an oily solid. 1H-NMR(D2O) 0.68–0.76 (m, 3H), 0.86 (d, J=6 Hz, 3H), 1.12–1.24 (m, 4H), 1.28–1.76 (m, 4H), 1.92–2.16 (m, 2H), 2.46–2.58 (m, 1H), 3.40–3.50 (m, 1H); Mass Spectra, M+H=169.

EXAMPLE MVT-B

2-Imino-4-methyl-6-allyl-pentamethylenimine Trifluoroacetic acid salt

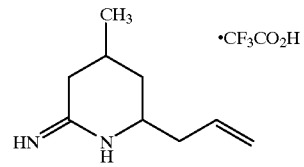

The title compound was prepared as in EXAMPLE 319, from 5.3 g of 2-allyl-4-methylcyclopentanone. A final purification by C-18 HPLC (0–40% acetonitrile/H2O, 30 min.) afforded 1.2 g of the title compound as an oily solid. 1H-NMR(D2O) 0.80–0.92 (m, 3H), 1.40–2.88 (m, 7H), 3.20–3.65 (m, 1H), 4.96–5.16 (m, 2H), 5.60–5.78 (m, 1H); Mass Spectra, M+H=153.

EXAMPLE 320

Methyl 2-(1-propyl)cyclopentanone 2-carboxylate

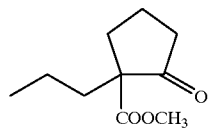

Methyl cyclopentanone 2-carboxylate (Fluka) (14.2 g, 0.1 mol), 1-iodopropane (Aldrich) (17 g, 0.1 mol), and potassium carbonate (10 g) were stirred in 100 ml of N,N-dimethylformamide (DMF) under nitrogen gas at 50° C. for

EXAMPLE 321

2-(1-Propyl)cyclopentanone

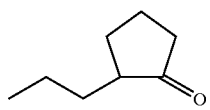

Methyl 2-(1-propyl)cyclopentanone 2-carboxylate (10 g, 0.054 mol), sodium cyanide (2.9 g, 0.06 mol) and dimethylsulfoxide (100 ml) was stirred at 1600° C. for 3 hr under nitrogen gas. After cooling, the reaction mixture was poured into ice-cooled water and extracted with 300 ml of a mixture of ethyl ether/hexanes (1/1). The ethyl ether/hexanes layer was separated, and was washed with saturated NaCl solution twice. After drying over MgSO4, the solvent was removed by rotary evaporation. The crude product was purified by silica gel column chromatography with a mixture of hexanes and ethyl acetate (7/3) as eluate. The product weighed 5.5 g (83%) yield). Mass Spectra: M+H=123.

EXAMPLE 322

2-Imino-6-(1-propyl)-pentamethylenimine trifluoroacetate salt

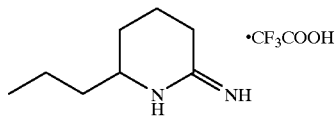

2-Imino-6-(1-propyl)-pentamethylenimine was prepared as in example 322 from 2-propylcyclopentanone. A final purification by revere-phased C18 HPLC (0–50% acetonitrile/H2O, 30 min,) afforded 0.3 g of the title compound as a white semisolid. 1H-NMR (D2O) 0.70–0.78 (t, 3H), 1.15–1.88 (m, 8H), 2.38–2.50 (m, 2H), 3.3–3.4 (m, 1H) Mass Spectra. M+H=255.

EXAMPLE 323

2-(1-butenyl)-2-carboethoxycyclohexanone

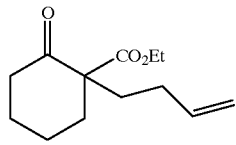

Sodium hydride, 60% in mineral oil (8.3 g, 200 mmol) was washed with 2 portions of hexane and then dried under an $N_2$ flow. This was suspended in dimethylformamide and ethyl 2-cyclohexanonecarboxylate (34.1 g, 200 mmol) was added slowly under $N_2$ (note the foaming and exotherm), with cooling with a 25° C. water bath. After complete addition, the mixture was stirred at 25° C. for ~1 hour and the treagents added. The stirring mixture was heated to 50° C. for 18 hours (overnight). The reaction was then cooled to room temperature. The entire mixture was poured into water, neutralized with dilute HCl and extracted with two portions of 1:1 ether-hexane The combined organics were then washed with two portions of water followed by saturated brine, then dried over $MgSO_4$, filtered and stripped giving 41.8 g of an impure mixture of products. Purification of the product by chromatography (silica gel,: 5% methyl t-butyl ether/90% hexane) gave 28.4 g of the title compound.

EXAMPLE 324

2-(1-butenyl)cyclohexanone

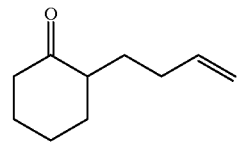

The reagents (1-butenyl)-2-carboethoxy cyclohexanone (11.2 g, 50 mmol), lithium chloride (10.6 g, 250 mmol), water (0.99 g, 55mmol), and dimethyl sulfoxide, (250 ml) were combined under $N_2$ and refluxed for 2 hours. The reaction was then cooled to 25° C. The reaction mixture was poured into water and extracted with two portions of 1:1 ether—hexane. The organic phases were combined and washed with two portions water followed by saturated brine and then dried over MgSO4. After filtering and stripping, the product was purified by fractional distillation at 1.5 mm Hg. (The product boils at 65 to 70° C. at 1 to 2 mm Hg.), giving 5.5 g of the desired title ketone.

EXAMPLE 325

2-(1-butenyl)cyclohexanone, oxime

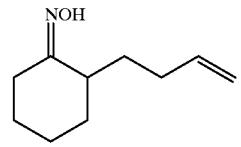

2-(1-butenyl)cyclohexanone from example 324 (7.70 g, 51 mmol) was converted to the title compound by the method of Example 24 using 5.3 g (76 mmol) of hydroxylamine hydrochloride and 7.0 g (85 mmol) of NaOAc in a mixture of 70 mL of EtOH and 70 mL of water. The procedure produced 8.48 g of the title material as a white solid.

EXAMPLE 326 hexahydro-7-(1-butenyl)-1H-azepin-2-one

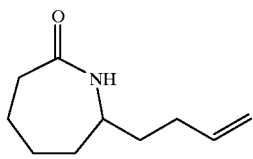

The title compound of EXAMPLE 325 was converted to the present title compound by the method of EXAMPLE 29.

EXAMPLE 327

4,5,6,7-tetrahydro-2-methoxy-7-(1-butenyl)-3H-azepine

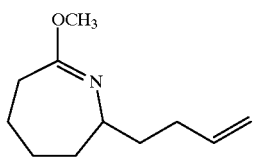

The product of Example 326 (1.34 g, 8 mmol) was reacted with trimethyloxonium tetrafluoroborate (1.63 g, 11 mmol) by the method of Example 26 to yield 1.5 g (100%) of the title material.

EXAMPLE 328 hexahydro-7-(1-butenyl)-1H-azepin-2-imine, monohydrochloride

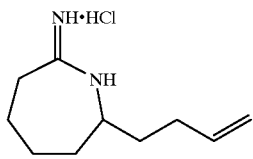

The product of Example 327 (1.5 g, 8 mmol) in 85 mL of MeOH was reacted with ammonium chloride (0.36 g, 6.8 mmol) by the method of Example 27 to yield 1.4 g (83%) of the title material.

Elemental analysis: $C_{10}H_{17}N_2 \cdot HCl \cdot 0.45\ H_2O$ (MW=210.83)

|  | C | H | N | Cl |
|---|---|---|---|---|
| Calculated: | 56.97 | 9.51 | 13.39 | 16.82 |
| Found: | 57.02 | 9.34 | 13.16 | 16.86 |

$^1$H NMR (D2O): δ5.75–5.95 (m, 1H), 5.1 (m, 2H), 3.65 (tt, 1H) 2.75 –2.5 (m, 2H), 2.3 (m, 2H), 2.05 –1.3 (m, 8H).

BIOLOGICAL DATA

The activity of the above listed compounds as NO synthase inhibitors has been determined in the following assays:

Citrulline Assay for Nitric Oxide Synthase

Nitric oxide synthase activity was measured by monitoring the conversion of [3H]-arginine to [3H]-citrulline. Mouse inducible nitric oxide synthase (miNOS) was prepared from an extract of LPS-treated RAW 264.7 cells and partially purified by DEAE-Sepharose chromatography. Rat brain constitutive nitric oxide synthase (rnNOS) was prepared from an extract of rat cerebellum and partially purified by DEAE-Sepharose chromatography. Enzyme and inhibitors were incubated at 37° C. for 15 minutes in a reaction volume of 100 mL with the following components added to start the reaction: 50 mM Tris (pH 7.6), 1 mg/ml bovine serum albumin, 1 mM DTT, 2 mM $CaCl_2$, 10 mM FAD, 10 mM tetrahydrobiopterin, 30 mM L-arginine containing L-[2, 3-3H]-arginine at 300 cpm/pmole and 1 mM NADPH. For constitutive NOS, 50 nM calmodulin was also added. The reaction was terminated by addition of cold stop buffer containing 10 mM EGTA, 100 mM HEPES, pH 5.5 and 1 mM citrulline. [3H]-Citrulline was separated by chromatography on Dowex 50W X-8 cation exchange resin and radioactivity determined with a liquid scintillation counter.

RAW CELL NITRITE ASSAY

RAW 264.7 cells are plated to confluency on a 96-well tissue culture plate grown overnight (17 h) in the presence of LPS to induce NOS. A row of 3–6 wells were left untreated and served as controls for subtraction of nonspecific background. The media was removed from each well and the cells are washed twice with Krebs-Ringers-Hepes (25 mM, pH 7.4) with 2 mg/ml glucose. The cells are then placed on ice and incubated with 50 mL of buffer containing L-arginine (30 mM)±inhibitors for 1 h. The assay is initiated by warming the plate to 37° C. in a water bath for 1 h. Production of nitrite by intracellular iNOS is linear with time. To terminate the cellular assay, the plate of cells is placed on ice and the nitrite-containing buffer removed and analyzed for nitrite using a previously published fluorescent determination for nitrite. T. P. Misko et al, *Analytical Biochemistry*, 214, 11–16 (1993). All values are the average of triplicate wells and are compared to a background-subtracted induced set of cells (100% value).

TABLE I

| Compound | iNOS $IC_{50}$ [μM] | cNOS $IC_{50}$ [μM] | Raw Cell $IC_{50}$ [μM] |
|---|---|---|---|
| Example 1 | 2.1 | 13.3 | 60 |
| Example 2 | 2.2 | 9.9 | >1000 |
| Example 3 | 43% * 10 μM | | |
| Example 4 | 4.6 | 2.4 | 14 |
| Example 5 | 3.2 | 9.4 | 18 |
| Example 6 | 0.055 | 0.285 | |
| Example 7 | 2.0 | 13.3 | |
| Example 8 | 0.16 | 0.99 | |
| Example 9 | 1.496 | 2.01 | |
| Example 10 | 0.043 | 0.127 | |
| Example 11 | 0.92 | 2.768 | |
| Example 12 | 5.1 | 32 | 1.8 |
| Example 13 | 0.6 | 2.0 | 14 |
| Example 14 | 5.0 | 23 | >1000 |
| Example 15 | 8% @ 10 μM | | |
| Example 16 | 0.8 | 4.0 | 4.3 |
| Example 17 | 0.8 | 2.7 | 28 |
| Example 18 | 0.8 | 6.0 | 6.0 |
| Example 19 | 42% @ 10 μM | | |

TABLE I-continued

| Compound | iNOS IC$_{50}$ [$\mu$M] | cNOS IC$_{50}$ [$\mu$M] | Raw Cell IC$_{50}$ [$\mu$M] |
|---|---|---|---|
| Example 20 | 1.0 | 50 | 160 |
| Example 21 | 40 | 500 | >1000 |
| Example 22 | 30 | 1300 | >1000 |
| Example 23 | 41% @ 10 $\mu$M | | |
| Example 60 | 1.1 | 32 | 3.5 |
| Example 70 | 5.9 | 32 | 24 |
| Example 90 | 7.0 | 46 | |
| Example 96 | 9.3 | 1405 | |
| Example 107 | 3.8 | 342 | 15 |
| Example 108 | 0.14 | 19 | 0.57 |
| Example 114 | 0.081 | 7.8 | 0.55 |
| Example 173 | 42% @ 10 $\mu$M | 49% @ 10 $\mu$M | |
| Example 164 | 60% @ 100 $\mu$M | 74% @ 100 $\mu$M | |
| Example 170 | 3.4 | 53 | |
| Example 182 | 1.4 | 14 | |
| Example 188 | 0.55 | 106 | 0.65 |
| Example 192 | 12 | 179 | 31 |
| Example 198 | 2.1 | 652 | 3.3 |
| Example 217 | 0.17 | 1.6 | 0.25 |

IN VIVO ASSAY

Rats were treated with an intraperitoneal injection of 10 mg/kg of endotoxin (LPS) with or without oral administration of the nitric oxice synthase inhibitors. Plasma nitrites were measured 5 hours post-treatment. The results show that the administration of the nitric oxide synthase inhibitor decreases the rise in plasma nitrites, a reliable indicator of the production of nitric oxide, induced by endotoxin.

IP is the abbreviation for 2-iminopiperidine. LPS is the abbreviation for endotoxin

| Compound | ED50 (mg/kg) |
|---|---|
| 96 | 3.8 |
| 108 | 3.7 |
| 114 | 3.4 |
| 188 | 3.7 |
| 198 | 5.0* (determined using iv infusion) |

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula:

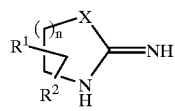

wherein
R1 and R2 form an alicyclic radical;
n is 2; and
X is a lower alkylene of one carbon optionally substituted with lower alkyl, lower alkoxy, amino, hydroxy, or haloalkyl.

2. A compound as recited in claim 1 wherein the compound is:

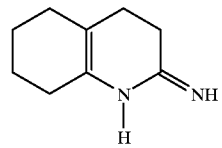

HCl.

3. A compound as recited in claim 1 wherein the compound is:

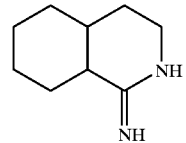

HOAc.

4. A pharmaceutical composition of the formula:

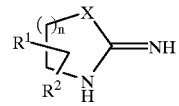

wherein
R1 and R2 form an alicyclic radical;
n is 2; and
X is a lower alkylene of one carbon optionally substituted with lower alkyl, lower alkoxy, amino, hydroxy, or haloalkyl.

5. The pharmaceutical composition as recited in claim 4 wherein the compound is:

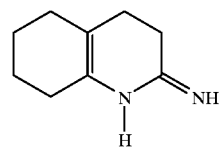

HCl.

6. The pharmaceutical composition as recited in claim 4 wherein the compound is:

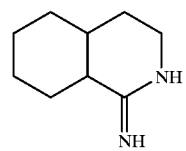

HOAc.

7. A method of inhibiting the activity of nitric oxide synthases comprising administering to a subject suffering from a nitric oxide synthase mediated disease, a non-toxic therapeutically effective amount of the compound of claim 1.

8. A method of inhibiting the activity of nitric oxide synthases comprising administering to a subject suffering from a nitric oxide synthase mediated disease, a non-toxic therapeutically effective amount of the compound of claim 2.

9. A method of inhibiting the activity of nitric oxide synthases comprising administering to a subject suffering from a nitric oxide synthase mediated disease, a non-toxic therapeutically effective amount of the compound of claim 3.

* * * * *